(12) United States Patent
Zhang et al.

(10) Patent No.: US 9,040,493 B2
(45) Date of Patent: May 26, 2015

(54) RNA ANTAGONISTS TARGETING GLI2 FOR THE TREATMENT OF LEUKEMIA

(75) Inventors: Yixian Zhang, Piscataway, NY (US); Zhengxing Qu, Warren, NY (US)

(73) Assignee: Santaris Pharma A/S, Hoersholm (DK)

( * ) Notice: Subject to any disclaimer, the term of this patent is extended or adjusted under 35 U.S.C. 154(b) by 0 days.

(21) Appl. No.: 13/384,163

(22) PCT Filed: Jan. 15, 2010

(86) PCT No.: PCT/US2010/021121
§ 371 (c)(1),
(2), (4) Date: May 29, 2012

(87) PCT Pub. No.: WO2011/008305
PCT Pub. Date: Jan. 20, 2011

(65) Prior Publication Data
US 2012/0232132 A1    Sep. 13, 2012

(30) Foreign Application Priority Data

Jul. 15, 2009  (WO) .................. PCT/IB2009/006407

(51) Int. Cl.
*A61K 48/00* (2006.01)
*C07H 21/02* (2006.01)
*C07H 21/04* (2006.01)
*A61K 31/7088* (2006.01)

(52) U.S. Cl.
CPC .................................. *A61K 31/7088* (2013.01)

(58) Field of Classification Search
None
See application file for complete search history.

(56) References Cited

U.S. PATENT DOCUMENTS

| | | | |
|---|---|---|---|
| 2001/0011681 A1* | 8/2001 | Edens et al. .................. 235/454 |
| 2001/0041681 A1* | 11/2001 | Phillips et al. .................. 514/44 |
| 2003/0092009 A1 | 5/2003 | Palm | |
| 2005/0112707 A1 | 5/2005 | Altaba et al. | |
| 2009/0005335 A1 | 1/2009 | Worm | |
| 2011/0124709 A1* | 5/2011 | Hedtjarn ..................... 514/44 A |

FOREIGN PATENT DOCUMENTS

| WO | WO03008545 | 1/2003 |
|---|---|---|
| WO | WO2010007522 | 1/2010 |

OTHER PUBLICATIONS

Kurreck et al. (Nucleic Acids Research, 2002, vol. 30, No. 9, 1911-1918).*
Schmidt et al., Nucleic Acids Research, 2004, vol. 32, No. 19, pp. 5757-2765.*
Bertrand et al., Biochemical and Biophysical Research Communications, 296, 2002, pp. 1000-1004.*

* cited by examiner

*Primary Examiner* — Amy Bowman
(74) *Attorney, Agent, or Firm* — Fish & Richardson P.C.

(57) ABSTRACT

The present invention relates to oligomer compounds (oligomers) for the treatment and prevention of acute myeloid leukemia, which target GLI2 mRNA in a cell, leading to reduced expression of GLI2.

13 Claims, 25 Drawing Sheets

FIGURE 1 – GLI2 mRNA - NM_005270  (SEQ ID NO 1).

```
   1 gattgccacc caggacgatg agcggctgag atggagacgt ctgcctcagc cactgcctcc
  61 gagaagcaag aagccaaaag tgggatcctg gaggccgctg gcttcccga ccogggtaaa
 121 aaggcctctc ctttggtggt ggctgcagcg gcagcagcag cggtagctgc ccaaggagtg
 181 ccgcagcatc tcttgccacc attccatgcg ccctaccga ttgacatgcg acaccaggaa
 241 ggaaggtacc attacgagcc tcattctgtc cacggtgtgc acgggcccc tgccctcagc
 301 ggcagccctg tcatctctga catctccttg atccggcttt ccccgcaccc ggctggcccct
 361 ggggagtccc ccttcaacgc ccccacccg tacgtgaacc cccacatgga gcactaccctc
 421 cgttctgtgc acagcagccc cacgctctcc atgatctctg cagccagggg cctcagcccc
 481 gctgatgtgg cccaggagca ccttaaggag aggggactgt ttggccttcc tgctccaggc
 541 accacccct cagactatta ccaccagatg accctcgtgg caggccaccc cgcgccctac
 601 ggggacctgc tgatgcacag cgggggcgct gccagcgcac cccatctcca cgactaccctc
 661 aacccgtgg acgtgtcccg tttctccagc ccgcgggtga cgcccgcct gagccgcaag
 721 cgggcgctgt ccatctcccc actctcagac gccagcctgg acctgcagcg gatgatccgc
 781 acctcaccca actcgctagt ggcctacatc aacaactccc gaagcagctc ggcggccagc
 841 ggttcctacg gcatctgtc agcgggtgcc ctcagccag ccttcacctt ccccaccccc
 901 atcaacccg tggcctacca gcagattctg agccagcaga ggggtctggg gtcagcctt
 961 ggacacacac caccctgat ccagccctca cccaccttcc tggccccagca gccccatggcc
1021 ctcaactcca tcaatgccac gccacccag ctcagcagca gcagcaactg tctgagtgac
1081 accaaccaga acaagcagag cagtgagtcg gccgtcagca gcaccgtcaa ccctgtcgcc
1141 attcacaagc gcagcaaggt caagaccgag cctgagggcc tgcggccggc ctcccctctg
1201 gcgctgacgc agggccaggt gtctggacac ggctcatgtg ggtgtgccct tccctctcc
1261 caggagcagc tggctgacct caaggaagat ctggacaggg atgactgtaa gcaggaggct
1321 gaggtggtca tctatgagac caactgccac tgggaagact gcaccaagga gtacgacacc
1381 caggagcagc tggtgcatca catcaacaac gagcacatcc acgggagaa gaaggagttt
1441 gtgtgccgct ggcaggcctg cacgcgggag cagaagccct tcaaggcgca gtacatgctg
1501 gtgctgcaca tgcggcgaca cacgggcgag aagcccaca agtgcacgtt cgagggctgc
1561 tcgaaggcct actcccgcct ggagaacctg aagacacacc tgcggtccca caccggggag
1621 aagccatatg tgtgtgagca cgagggctgc aacaaagcct tctccaacgc ctcggaccgc
1681 gccaagcacc agaatcgcac ccactccaac gagaaaccct acatctgcaa gatcccagge
1741 tgcaccaaga gatacacaga cccagctct ctccggaagc atgtgaaaac ggtccacggc
1801 ccagatgccc acgtcaccaa gaagcagcgc aatgacgtgc acctccgcac accgctgctc
1861 aaagagaatg gggacagtga ggccggcacg gagcctggcg gcccagagag caccgaggcc
1921 agcagcacca gccaggccgt ggaggactgc ctgcacgtca gagccatcaa gaccgagagc
1981 tccgggctgt gtcagtccag ccccagggcc cagtcgtcct gcagcagcga gccctctcct
2041 ctgggcagtg ccccaacaa tgacagtggc gtggagatgc cggggacggg gccggtggagc
2101 ctgggagacc tgacggcact ggatgacaca cccccagggg ccgacacctc agcctggct
2161 gccccctccg ctggtggcct ccagctgcgc aaacacatga ccaccatgca ccggttcgag
2221 cagctcaaga aggagaagct caagtcactc aaggattcct gtcatgggc cgggccgact
2281 ccacacacg ggaacaccaa gctgcctccc ctcccgggaa gtggctccat cctggaaaac
2341 ttcagtggca gtggggcgg cgggcccgcg gggctgctgc cgaaccccgc gctgtcggag
2401 ctgtccgcga gcgaggtgac catgctgagc cagctgcagg agcgcgcga cagctccacc
2461 agcacggtca gctcggccta cacgtgagc cgccgctcct cggcatct cccctacttc
2521 tccagccgcc gctccagcga ggcctcgccc ctgggcgccg ccgccgca caacgcgagc
2581 tccgctgact cctacgaccc catctccacg gacgtgtgc ggcgctcgag cgaggccagc
2641 cagtgcagcg gcggctccgg gctgctcaac ctcacgcccg gcagcagta cgcagctgcgg
2701 gccaagtacg cggcagcac tggcggcccc ccgcccactc cgctgcccgg cctggagcgc
2761 atgagcctgc ggaccaggct ggcgctgctg gacgcgcccg agcgcacgct gcccgccggc
2821 tgcccacgcc cactgggcc gcgggtgcc agcgacggg cgacctatgg ccacggccac
2881 gcgggggctg cgcccgcctt ccccacgag gctccaggcg gcggagcag cggggccagc
2941 gaccctgtgc ggcggcccga tgcctgtcc ctgcgcgggg tgcagcgctt ccacagcacc
3001 cacaacgtga ccccggcc gctgccgcc tgtgccgaca ggcgaggcct ccgcctgcag
3061 agccaacccga gcaccgacgg cacctggcc cgggcgcct actcgcccg gccgctagc
3121 atcagcgaga acgtggcgat ggaggccgtg gcggcaggag tggacggcgc ggggccgag
3181 gccgacctgg ggctgccgga ggacgacctg gtgcttccag acgacgtggt gcagtacatc
3241 aaggcgcacg ccagtggcgc tctggacgag ggcacggggc aggtgtatcc cacggaaagc
3301 actggcttct ctgacaaccc cagactaccc agcccgggc tgcacggcca gcgcaggatg
3361 gtggctgcgg actccaacgt gggccctcc gccctatgc tgggaggatg ccagttaggc
```

FIGURE 1 CONTINUED

```
3421 tttgggcgc cctccagcct gaacaaaaat aacatgcctg tgcagtggaa tgaggtgagc
3481 tccggcaccg tagacgccct ggccagccag gtgaagcctc cacccttcc tcagggcaac
3541 ctggcggtgg tgcagcagaa gcctgccttt ggccagtacc cgggctacag tccgcaaggc
3601 ctacaggcta gccctggggg cctggacagc acgcagccac acctgcagcc ccgcagcgga
3661 gccccctccc agggcatccc cagggtaaac tacatgcagc agctgcgaca gccagtggca
3721 ggcagccagt gtcctggcat gactaccact atgagccccc atgcctgcta tggccaagtc
3781 cacccccagc tgagcccag caccatcagt ggggccctca accagttccc ccaatcctgc
3841 agcaacatgc cagccaagcc agggcatctg gggcaccctc agcagacaga agtggcacct
3901 gacccacca cgatgggcaa tcgccacagg gaacttgggg tcccgattc agccctggct
3961 ggagtgccac cacctcaccc agtccagagc tacccacagc agagccatca cctggcagcc
4021 tccatgagcc aggagggcta ccaccaggtc cccagccttc tgcctgcccg ccagcctggc
4081 ttcatggagc cccaaacagg cccgatgggg gtggctacag caggctttgg cctagtgcag
4141 cccggcctc ccctcgagcc cagcccact ggccgccacc gtggggtacg tgctgtgcag
4201 cagcagctgg cctacgccag ggccacaggc catgccatgg ctgccatgcc gtccagtcag
4261 gaaacagcag aggctgtgcc caagggagcg atgggcaaca tggggtcggt gcctcccag
4321 ccgcctccgc aggacgcagg tgggccccg gaccacagca tgctctacta ctacggccag
4381 atccacatgt acgaacagga tggaggcctg gagaacctcg ggagctgcca ggtcatgcgg
4441 tcccagccac cacagccaca ggcctgtcag gacagcatcc agcccagcc cttgccctca
4501 ccaggggtca accaggtgtc cagcactgtg gactccagc tcctggaggc ccccagatt
4561 gacttcgatg ccatcatgga tgatggcgat cactcgagtt tgttctcggg tgctctgagc
4621 cccagcctcc tccacagcct ctccagaac tcctcccgcc tcaccacccc ccgaaactcc
4681 ttgaccctgc cctccatccc cgcaggcatc agcaacatcg ctgtcgggga catgagctcc
4741 atgctcacca gcctcgccga ggagagcaag ttcctgaaca tgatgaccta gaggccgag
4801 cgcctggtgc tgagtgcacc cggagggggtc atcgtgcc agagcctggg gattccagct
4861 gtcttgtctt tttccaaaaa agtgttaaat aggcttgagg ggttgttgcg caatggccgc
4921 ttcagatgac agatgttgta agagaaggtt tatgggcatc ctctctggtc ttttggatta
4981 ttcctcagaa caatgaaaaa agtctccata ggacaggaag gaatgcaaaa ctcatttaca
5041 cagtgcttc cagcctttgg tgcttacagg acgcgctgt tccggcttct tcacggctga
5101 cattcggcta acgagggatt actttggcca aaacctttca aaggatatgc agaaagatgg
5161 tagggagcat ttgggtttga atctgaatgc tatactggat actctgctcc ggaaagatga
5221 gcttttatt ctactacttg gaaggaaaag gaattcctgg tccacctgaa ttcctctatg
5281 aagcctaact cttgaggtct ctaacatacc ttgtcataga ggaaaagcac agattatacc
5341 tggatgattc aggagcacat tctgattcca ggtttggtag agctggctct tctactccgt
5401 aaagccgagt ctgggactgg cagcccatcc aagtgtatat gaatgaataa agcatccaag
5461 tatatatgaa tgaataaagt atgtaagtat caccagaaaa aggaaagaaa aaatgtactc
5521 cttggggcaa gcccagaagc tgccctggcc tctccagacc gtgtttacag tgtttgcatg
5581 tagaatgtag cccttcctga aaagaagact tgtttctaaa tacctcgggg ctgctggagc
5641 cgctgtgggt tagggatgga ctgaggcctc gaggagtgag ggtgcacccg gggcccagcc
5701 tcaggctgcc ctagggatct ctcagtagga agaggaagtt gcgtgtttac ccaatcctgt
5761 ttctccaatg caacgtccac ccactttacc accaaaaact ccaggcctg acggcagccc
5821 ggtccccag cactcaccag cagcccagtg ttctccacca agccacagtg tgcatgcctg
5881 gtatcctccg gattccttc cttctgcccg ctgagtcact gggcagagaa tgatgacatg
5941 tgtaggtggt gtggttgggg gtggaaaggg gaagggg-tg atcctcagga ctctgaggga
6001 gcatcgttga atttctgtgt tcagtgtgac caagacccac ctggaaatgg aatttggaac
6061 tggcttcagg agacatcatt cctgaacaca ctgtagggtg aattggtgca tcttcccac
6121 catacacaca cacacacaca cacacacaca cacacacaca cacacacccc aaacctttc
6181 atggggaatg tgtggcaacc ttgccaaaca gcaccactca gagtgtgact ctgactgtga
6241 ccttggcctt aatgaggaac ttcttaggag agtttgagga caaggccaac atcgtcatct
6301 gggctcgctg cgtccagca catcaaaactc tgtccagaga caaggccaac tgcaaatgaa
6361 agccagggaa cattgctaag ggtctgtggc tctgtggtgg tgttcatcgc cttcctgaga
6421 taggatttcc cttgccagtc ccaacctgta tatattctgt acagaagaca tccctgaata
6481 tactgtaggt gagtcgtcca gccaaattta tatctccaaa acatttttag ctttttctac
6541 atgctatgaa ttgagatgac atgctcaact tgtaaataag tctttttgta cattaaaaaa
6601 gtaatttttt cataatttat cttgtctatc tgcttcccc ttgacagtag ttaatgagaa
6661 cctgggcagt aaatttggtg cattcgagca gaaattaggc tgtattttt cttaacagtg
6721 tcaaaattga ctatcccgcc tttgccaaga aatgtttaat gctgaggcaa aaaaaaaaa
```

FIGURE 2 – Human GLI1mRNA - NM_005269 (SEQ ID NO 2).

```
   1 cccagactcc agccctggac cgcgcatccc gagcccagcg cccagacaga gtgtccccac
  61 accctcctct gagacgccat gttcaactcg atgaccccac caccaatcag tagctatggc
 121 gagccctgct gtctccggcc cctcccagt caggggccc ccagtgtggg gacagaagga
 181 ctgtctggcc cgccttctg ccaccaagct aacctcatgt ccggccccca cagttatggg
 241 ccagccagag agaccaacag ctgcaccgag ggccactct tttcttctcc ccggagtgca
 301 gtcaagttga ccaagaagcg ggcactgtcc atctcacctc tgtcggatgc cagcctgcac
 361 ctgcagacgg ttatccgcac ctcacccagc tccctcgtag ctttcatcaa ctcgcgatgc
 421 acatctccag gaggctccta cggtcatctc tccattggca ccatgagccc atctctggga
 481 ttcccagccc agatgaatca ccaaaaaggg ccctcgcctt cctttggggt ccagccttgt
 541 ggtccccatg actctgcccg gggtgggatg atcccacatc ctcagtcccg gggacccttc
 601 ccaacttgcc agctgaagtc tgagctggac atgctggttg gcaagtgccg ggaggaaccc
 661 ttggaaggtg atatgtccag ccccaactcc acaggcatac aggatcccct gttggggatg
 721 ctggatgggc gggaggacct cgagagagag gagaagcgtg agcctgaatc tgtgtatgaa
 781 actgactgcc gttgggatgg ctgcagccag gaatttgact cccaagagca gctggtgcac
 841 cacatcaaca gcgagcacat ccacgggag cggaaggagt tcgtgtgcca ctgggggggc
 901 tgctccaggg agctgaggcc cttcaaagcc cagtacatgc tggtggttca catgcgcaga
 961 cacactggcg agaagccaca caagtgcacg tttgaagggt gccggaagtc atactcacgc
1021 ctcgaaaacc tgaagacgca cctgcggtca cacacgggtg agaagccata catgtgtgag
1081 cacgagggct gcagtaaagc cttcagcaat gccagtgacc gagccaagca ccagaatcgg
1141 acccattcca atgagaagcc gtatgtatgt aagctccctg ctgcaccaa acgctataca
1201 gatcctagct cgctgcgaaa acatgtcaag acagtgcatg gtcctgacgc gtccacccct gttggggatg
1261 aaaacggcac gtggggatgg ccccctgcct cgggcaccat ccatttctac agtggagccc
1321 aagagggagc gggaaggagg tccatcagg gaggaaagca gactgactgt gccagagggt
1381 gccatgaagc cacagccaag ccctgggcc cagtcatcct gcagcagtga ccactccccg
1441 gcagggagtg cagccaatac agacagtggt gtggaaatga ctggcaatgc aggggggcagc
1501 actgaagacc tctccagctt ggacgaggga ccttgcattg ctggcactgg tctgtccact
1561 cttcgccgcc ttgagaacct caggctggac cagctacatc aactccggcc aatacggacc
1621 cggggtctca aactgccag cttgtcccac accggtacca ctgtgtcccg ccgcgtgggc
1681 ccccagtct ctcttgaacg ccgcagcagc agctccagca gcatcagctc tgcctatact
1741 gtcagccgcc gctcctcct ggcctctcct ttcccccctg gctcccacc agagaatgga
1801 gcatcctccc tgcctggcct tatgcctgcc cagcactacc tgcttcgggc aagatatgct
1861 tcagccagag ggggtggtac ttcgcccact gcagcatcca gcctggatcg gataggtggt
1921 cttcccatgc ctccttggag aagccgagcc gagtatccag gatacaaccc caatgcaggg
1981 gtcacccgga gggccagtga cccagcccag gctgctgacc gtcctgctcc agctagagtc
2041 cagaggttca agagcctggg ctgtgtccat ggggcacccg ctgtggcagg gggaggacag
2101 aactttgatc cttacctccc aacctctgtc tactcaccac agccccccag catcactgag
2161 aatgctgcca tggatgctag agggctacag gaagagccag aagttgggac ctccatggtg
2221 ggcagtggtc tgaaccccta tatggacttc ccacctactg atactctggg atatgggga
2281 cctgaagggg cagcagctga gccttatgga gcgagggtc caggctctcc gcctcttggg
2341 cctggtccac ccaccaacta tggccccaac ccctgtccc agcaggcctc atatcctgac
2401 cccacccaag aaacatgggg tgagttccct tcccactctg gctgtaccc aggccccaag
2461 gctctaggtg gaacctacag ccagtgtcct cgacttgaac attatgggaca agtgcaagtc
2521 aagccagaac aggggtgccc agtgggggtct gactccacag gactggcacc ctgcctcaat
2581 gccccacccca gtgagggggcc cccacattca cagcctctct ttcccatta cccccagccc
2641 tctcctcccc aatatctcca gtcaggcccc tatacccagc caccccctga ttatcttcct
2701 tcagaaccca ggccttgcct ggactttgat tcccccaccc attcacagg gcagctcaag
2761 gctcagcttg tgtgtaatta tgttcaatct caacaggagc tactgtggga gggtggggc
2821 agggaagatg ccccccgccca ggaaccttct taccagagtc ccaagttcct ggggggttcc
2881 caggttagcc caagccgtgc taaagctcca gtgaacacat atggacctgg ctttggaccc
2941 aacttgccca atcacaagtc aggttcctat cccacccctt caccatgcca tgaaaatttt
3001 gtagtggggg caaatagggc ttcacatagg gcagcagcac cacctcgact tctgccccca
3061 ttgcccactt gctatgggcc tctcaaagtg ggaggcacaa accccagctg tggtcatcct
3121 gaggtgggca ggctaggagg gggtcctgcc ttgtaccctc ctcccgaagg acaggtatgt
3181 aacccctgg actctcttga tcttgacaac actcagctgg actttgtggc tattctggat
3241 gagccccagg ggctgagtcc tctccttcc catgatcagc ggggcagctc tggacatacc
3301 ccacctccct ctgggccccc caacatggct gtgggcaaca tgagtgtctt actgagatcc
3361 ctacctgggg aaacagaatt cctcaactct agtgcctaaa gagtagggaa tctcatccat
3421 cacagatcgc atttcctaag gggtttctat ccttccagaa aaattggggg agctgcagtc
3481 ccctgcacaa gatgccccag ggatgggagg tatgggctgg gggctatgta tagtctgtat
3541 acgttttgag gagaaatttg ataatgacac tgtttcctga taataaagga actgcatcag
```

FIGURE 3 –Human Gli3 mRNA sequence - NM_000168 (SEQ ID NO 134).

```
   1 gcgcacacco gccgctccca ctcacccgcg ccgtctccc gcttcccog cgcgcccgc
  61 ggccgccgc gggtctatgg gaagttcggg gacttgacag ccgctgccgc cgcagggcat
 121 ttttggtcga agagagctga agtaatgaga agacatcatg gaggcccagt cccacagctc
 181 cacgaccact gaaaagaaaa aagttgagaa ttccatagtg aagtgctcca ctcgaacaga
 241 tgtgagcgag aaagccgttg cctccagcac cacttctaat gaggatgaaa gtcctggaca
 301 gacttatcac agagagagaa gaaacgcaat cactatgcag ccacagaatg tccaggggct
 361 cagcaaagtc agtgaggaac cttcaacatc gagtgacgag agggcctcat tgatcaagaa
 421 agagatccat gggtccctgc cacacgtggc ggagccctct gtgccgtacc gcgggacggt
 481 gtttgccatg gacccccagga atggttacat ggagcccccac taccacctc ctcatcttt
 541 ccctgccttc catcctcctg taccaattga tgccagacat catgagggcc gttaccatta
 601 cgatccatct ccgattcctc cattgcatat gacttccgcc ttatctagta gccctacgta
 661 tccggacctg cccttcatta ggatctcccc acaccggaac cccactgctg cttccgagtc
 721 tccccttcagc cctccacatc cctacattaa tccctacatg gactatatcc gctccttgca
 781 cagcagccca tcgctctcca tgatctcagc aacccgtggg ctgagcccta cagatgcgcc
 841 ccatgcagga gtcagcccag cagaatacta tcatcagatg gccctgctaa ctggccagcg
 901 cagccctat gcagacatta ttccctcagc tgccaccgcc ggcacggggg ccatccacat
 961 ggaatatctt catgctatgg atagcaccag attctccagc cccagcctgt cagccaggcc
1021 gagccgaaaa cgtacactgt ccatatcacc actctccgat catagctttg accttcagac
1081 catgataagg acgtctccca actccttggt cacgattctc aataattccc gtagcagctc
1141 ttcagcaagt ggctcctatg gtcacttatc tgcaagtgca atcagccctg ccttgagctt
1201 cacctactct tccgcgcccg tctctctcca catgcatcag cagatcctaa gccgacaaca
1261 gagcttaggt tcagcctttg gacacagccc tccactcatc caccctgccc caacttttcc
1321 aacacagagg cctattccag ggatccctac ggttctgaac cccgtccagg tcagctccgg
1381 cccttctgag tcctcacaga acaagcccac gagtgagtct gcagtgagca gcactggtga
1441 cccgatgcac aacaagaggt ccaagatcaa acccgatgaa gacctcccca gcccagggcc
1501 tcggggggcag caggaacagc ccgaaggaac aaccccttgtc aaggaggaag gggacaaaga
1561 tgaaagcaaa caggagcctg aagtcatcta tgagacaaac tgccactggg aaggctgcgc
1621 gagggagttc gacacccaag agcagcttgt gcaccatata aataacgacc atattcatgg
1681 agagaagaag gagttcgtgt gcaggtggct ggactgctca agagagcaga aaccctttcaa
1741 agcccagtat atgttggtag tgcatatgag aagacacacg ggcgagaagc ctcacaaatg
1801 cacttttgaa ggttgcaaa aggcctactc gagactagaa aacttgaaaa cacacttgag
1861 atctcacact ggagagaaac catacgtctg tgagcacgaa ggttgcaaca aggctttctc
1921 aaatgcctct gatcgcgcca aacaccaaaa cagaacgcat tccaatgaga aaccatatgt
1981 gtgcaaaatc ccaggctgca ctaagcgtta cacagaccca agctccctcc ggaaacatgt
2041 gaagacagtg catggcccag aggctcatgt caccaagaag cagcgagggg acatccatcc
2101 tcggcogcca ccccgagag attccggcag ccattcacag tccaggtcgc ctggccgacc
2161 gactcaggga gcccttggtg agcagcagga cctcagcaac actacctcaa agcgggaaga
2221 atgcctccag gtgaaaaccg tcaaggcaga gaagccaatg acatctcagc caagccctgg
2281 tgtcagtct tcatgcagca gccaacagtc cccatcagc aactattcca acagtgggct
2341 cgagcttcct ctgaccgatg gaggtagtat aggagacctc agtgccatcg atgaaacccc
2401 aatcatggac tcaaccattt ccactgcaac cacagccctt gctttgcaag ccaggagaaa
2461 cccgccaggg accaaatgga tggagcaacgt aaaactagaa aggctaaaac aagtgaatgg
2521 aatgtttcog cgactgaacc ccattctacc ccctaaagcc cctgcggtct ctcctctcat
2581 aggaaatggc acacagtcca caaacacctg cagcttgggt gggcccatga cgcttctccc
2641 gggcagaagc gacctctctg gggtggacgt cactatgctg aacatgctca cagaaggga
2701 cagcagcgca agcaccatca gctcggccta cctgagcagc cgccgctcct cagggatctc
2761 gccctgcttc tccagccgcc gtccagcga ggcgtcacag gccgagggcc ggccgcagaa
2821 cgtgcgcgtg gccgactcct acgacccccat ctccaccgac gcctcgcgcc gctccagcga
2881 agccagccag agcgacggcc tgcccagcct gctcagcctc acgccgcc agcagtaccg
2941 cctcaaggcc aagtacgcgg ctgccacagg agggcgccg ccgacgcccc tgcccaacat
3001 ggagaggat agcctgaaga cgcgcctggc gctgctcggg gatgcctcg agcctggcgt
3061 ggccctgcct ccagttcatg cccgaggag gtgcagcgac gggggagccc acggctacgg
3121 gcggcgcca ctgcagccgc acgatgcgcc gggccacgggc gtgaggaggg ccagcgaccc
3181 ggtgcggaca ggctccgagg gctggcctca gcctgtgtg ccgccttca gcagcctcag
3241 cagctgcaac ccccggcga tggccacgtc cgcggagaag cgcagtctgt gcttcagaa
3301 ttacacgcgg cccgagggcg gccagtcccg aaacttcac tcgtccccct gtcctcccag
3361 catcaccgag aacgtcaccc tggagtccct gaccatggac gctgatgcca acctgaacga
```

FIGURE 3 CONTINUED

```
3421 tgaggatttc ctgccggacg acgtggtgca gtatttaaat tcccagaacc aagcagggta
3481 cgagcagcac ttcccagcg ccctccgga cgacagcaaa gtgccccacg ggcccgtga
3541 ctttgacgcg cccgggctgc cagacagcca cgctggccag cagttccatg ccctcgagca
3601 gccctgcccc gagggcagca aaaccgacct gccccattcag tggaacgaag tcagctccgg
3661 aagcgccgac ctgtcctcct ccaagctcaa gtgtggccg cggcccgctg tgccgcagac
3721 tcgcgccttt gggttctgca acggcatggt cgtccacccg cagaacccct tgaggagcgg
3781 gcctgctggg ggctatcaga ccctcgggga gaacagcaac ccctacggtg gcccagagca
3841 cttgatgctc cacaacagcc ccggaagtgg caccagtgga aacgccttcc atgaacagcc
3901 ctgtaaggcc ccgcagtatg ggaactgtct caacaggcag ccagtggccc ctggtgcact
3961 cgacggtgcc tgtggtgccg ggattcaagc ctcaaagctg aagagcaccc ccatgcaagg
4021 gagcggggc cagctgaatt tcggcctgcc ggtagcgcca aatgagtcag ctggcagcat
4081 ggtgaatggc atgcagaacc aggaccagt gggacagggg tacctggctc accagctcct
4141 cggcgacagc atgcagcacc cggggcagg ccgccccggt cagcagatgc ttgggcagat
4201 tagtgctacc tcacacatca acatctacca agggcagag agctgcctgc caggggctca
4261 cggcatgggc agccagccgt caagcttggc agttgtcagg ggctaccagc catgtgccag
4321 ctttggggc agcaggcgcc aggctatgcc gagggacagc cttgctctgc agtcaggaca
4381 gctcagtgac acaagtcaga cctgcaggg gaatggtatc aagatggaga tgaaagggca
4441 gccccatccg ctgtgctcta atctgcagaa ttactctggt cagttctatg accaaaccgt
4501 gggcttcagt cagcaagaca cgaaagctgg ttcattctct atttcagacg ccagctgcct
4561 gctacagggg accagcgcca aaaactctga gttactttcc ccaggtgcta atcaggtgac
4621 aagcacagtg gacagcctcg acagccatga cctggaaggg gtacagattg acttcgatgc
4681 catcatagac gatggggacc actccagcct gatgtcgggg gccctgagcc caagtatcat
4741 tcagaacctt tcccatagct cctcccgcct caccacgcct cgggcgtccc tcccattccc
4801 agcgctgtcc atgagcacca ccaacatggc tatcggggac atgagttctt tgctgacctc
4861 cctagcggaa gaaagcaaat tccttgcagt tatgcaatag gctttaggaa aaaagactg
4921 caaccaacgg aaatcaatag gagttgaaga gattaaactg actttgtttt ggctgttttt
4981 ttagttctgt atgtatttta gcaatctcat ctcacctaac tgagatgtgt ttcaattata
5041 ttccttttat ggaaaaggac tctgaaaaac cctaaagtat tctagggaga aactgtcttc
5101 catttcagtt ttgaatcagt attgttacac tcaaaccacc ctcttttaa aaaaaaaaa
5161 aaaaactgta agcccgccc cttttagt aaaccgatgt aaatttgtga tgtgcatatt
5221 cttctttctt ttagaagagc agtcaaatta aaggatttga catgttttgc tgttgctcaa
5281 aggaaatagg agttggtgtg cttgtgacca aggggttaca cttccagctt ttaaaattct
5341 cctttacatg tgctcagtgt tttgttttgt gtttggtttt ctgttttta tttttaattcc
5401 cacattggc acaagaatca gaatatggat agctagttta agaaacttttt gtgggtgcac
5461 tgtagcatag atgacagaat attgatgttc ccccatctc caattcagtt cagggcattc
5521 cacagttaaa cagaaatggg aacgtgggc tcttataaat gaaatgggcg ctcacagttt
5581 tggttttcag ctcttcatgt ctgtaagtgt gctttgggg aggctatgtc tgtatggtcg
5641 attctcagtt atcacatttg cctctcctcc cactaccttc atgaacattc agtgctgttt
5701 cgcactgcag ttagagagaa gggacggaca gttggtgaca ctcagccaca ttgctacttt
5761 tatctgttct ggtaagaagt tagatagatg gtagattgaa gcaattgggt agaattagtt
5821 ggggaatat ttatgagttg ctgtgtttgt tgattagttc catctctttc ccatttttaac
5881 tgagaattga ttatatatag ctctaagtat ataggtattt aaacaaccc acaagcggct
5941 gtatcagtaa catttattaa ttccactata gtgaggagg atttccattc taaatacctt
6001 attttgaggg atttataaaa cttagttgta aaagagaaag cccacatagt gggaataaat
6061 tgcttcagcc attttagta tttgagagca ctagggaaga tgtttagtag ctgtgtggat
6121 gcctttttc acaccctgtc tattgaatgc tgcatccatt cacgaagtta aatgttacat
6181 gcagttagtc cttaatgtgg actgatctg tactttgtt ttggattaaa acatttaaag
6241 attttttgaag tgcagctact ccccacgtgc atttgataca cataaaagtc atactgtgtg
6301 tgcacaaaga gtacatggat tttccagcat attgctttaa aaaattatat aaactgttaa
6361 aatattaaca cctcaggcta cctgctgtat tctgtcccat tgacccctgg aattggattt
6421 actgcaagtg attgataatt caattatgtg gcttttcccc tttaatcttg ccatttaaat
6481 tacagtagaa agacaaaatc aagtaaaata aagtgttaga taatagaaag agtgttaaga
6541 ccagcccact tttctcatgt ttatgttctt tcatttggac caagaatctc cgcatggagg
6601 ttgatttgcc actggggact ttggctaaga ctattaggtt tgctttcaac tagatgttcc
6661 tgagacaagc agaggacac tgcaattccc cttccatgcc tgctgttctc ccccatgtaa
6721 gtcttctttg aaattaacgg atgtgtgtcc tttggaacag cccoataaca aaagagaact
6781 actgatctga gcataggaaa gtagaggctc taccactttt cagttgaaaa agcaagactt
6841 tctctgtgtt tctgaaacaa ggcataatgt tgtcacagaa tcagagatcc agtctcactt
```

FIGURE 3 CONTINUED

```
6901 ttccacaaat ctccaaatct ccagtcttat cttgtgtgct ctaatggttt ggttcaatcc
6961 ctttccaact cttgttttca aagcatgggg cctgagtgtt ctccactcct cctaagaaag
7021 gagcttgggt ggaagggacc atgctgacct cctccatcag agggctcttc cagtagtatt
7081 ctcggatgca acctccattt ctcagttacc attatttcct gtatcagctt tgtcottcct
7141 ggagggatgc acagtgatcc ggcccaccac tgttgttgtc ttgtgcttct gctctttcct
7201 atggtttcag gttatttttct gggtttcccc tattcttctt ttatttcttt ttttttttat
7261 atttgcttc ctttctactg cttttagatt tgcaggagat gcaagtttca gctcaatgtt
7321 tggcttctct caatatggaa atttcagaag gacagaggag aggagggagg aagaagaaag
7381 tatactcctc cagaatttca gtgatctgtt gtggcagtcc agtggaagga aggtcttttg
7441 aggtcactta gaagcatctt tttgggacat cctttggga tctctgtagg ctaggcatct
7501 catatcttga gactcaccc cagcctccaa gcctctctcc atttctctaa cctatgcatt
7561 ttagagcgag aggaccgcct cactagtgtc accatcctgc cttttctaaa acatgcaggc
7621 tcacacattc tactcctgct taatgtctgt gttaaacgtt ttctaaccat ttttgtttta
7681 tttttctgaa aaagttaacc cctcccaact cctcacacat tggctcttcc tcttgagcca
7741 caaagttttg attcttgcga tgtatgtgcc ttattttatg ttaatcttgt caatgagagg
7801 gaccagttgg tgttgcccaa tcagcactcc aaggctgtgt gtgcaccagc cagagagcgc
7861 acggtggtag cagagtcgag gctgtcttgt atcctggttt catgtgttgt tttgaactga
7921 taggaggatg tcctcttctg acaagttacc cttgtgtatc ctgcagacat gtaaaataaa
7981 atacaagttc atttttttca cctttttag attttttaa aaaataaaat gtgtaatcct
8041 ttttttaaaa gaaacacatg taaatacatt taagtattgt aggcatacg ttcagatgtg
8101 actggcccag gcgttcctcg gacaagcctg cattcccgt gatcacgccc acctcaagcc
8161 caggggctgc agcccagcca cagatgaact ctacctttgc tttcagaacc acttagtcct
8221 tttgtaacaa agaaaaaaaa atgtttctta caatgtcaat aaaaaattct ttgtatggaa
8281 a
//
```

G1:Saline,KD 0±65.7%
G2: 3,3mg/kg, KD    -83.4±42.9%
G3: 3,30mg/kg, KD   -50.9±38.5%
G4: 19,3mg/kg,      -160.6±108.9%
G5: 19,30mg/kg,     ±27.4%
G6: 19,100mg/kg,    ±23.7%

G7:75,3mg/kg, KD    -34.0±32.7%
G8:75,30mg/kg, KD   ±33.9%
G9:75,100mg/kg, KD  -76.6±108.6%
C:518A, in vitro control,KD0%
T:518A in vitro, 10 nM 4478,KD

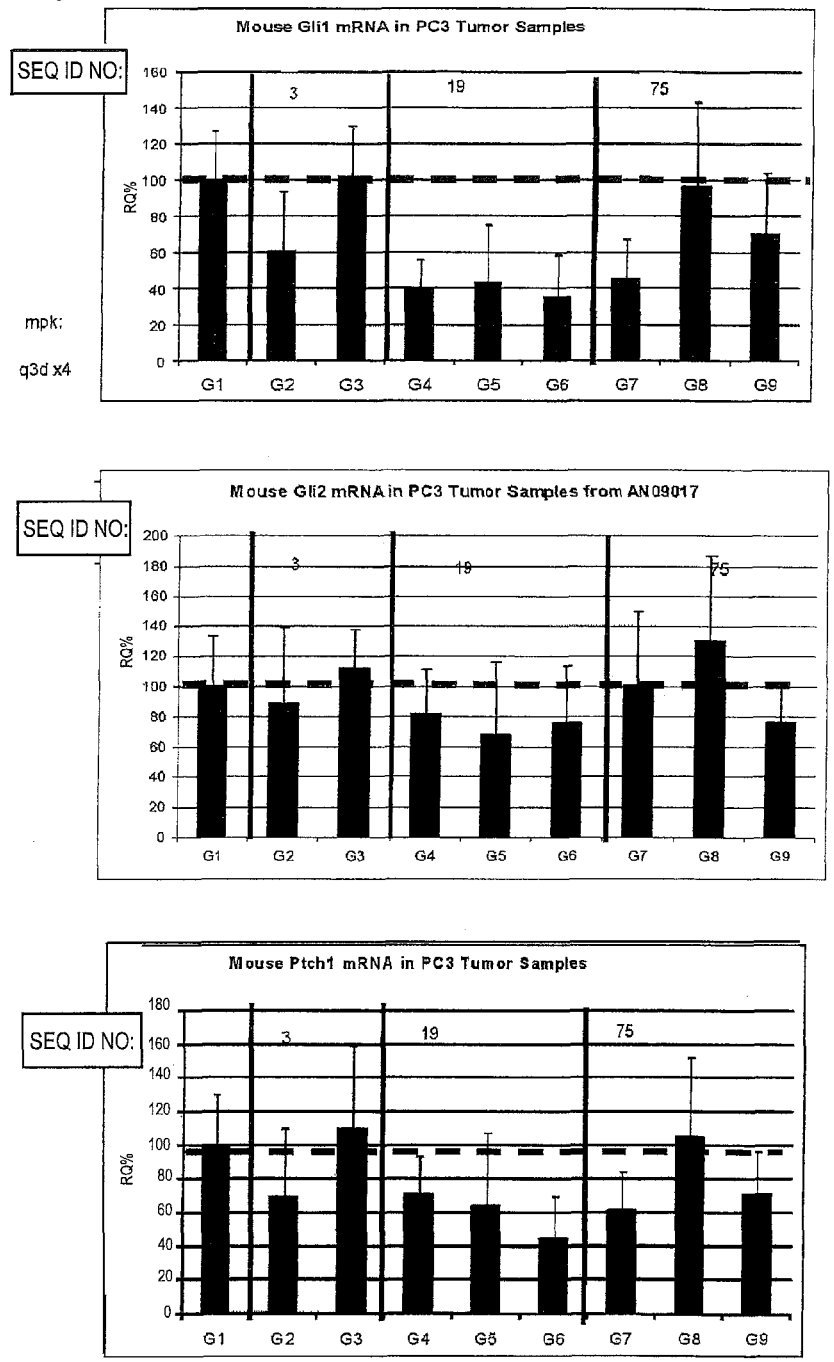

Figure 16
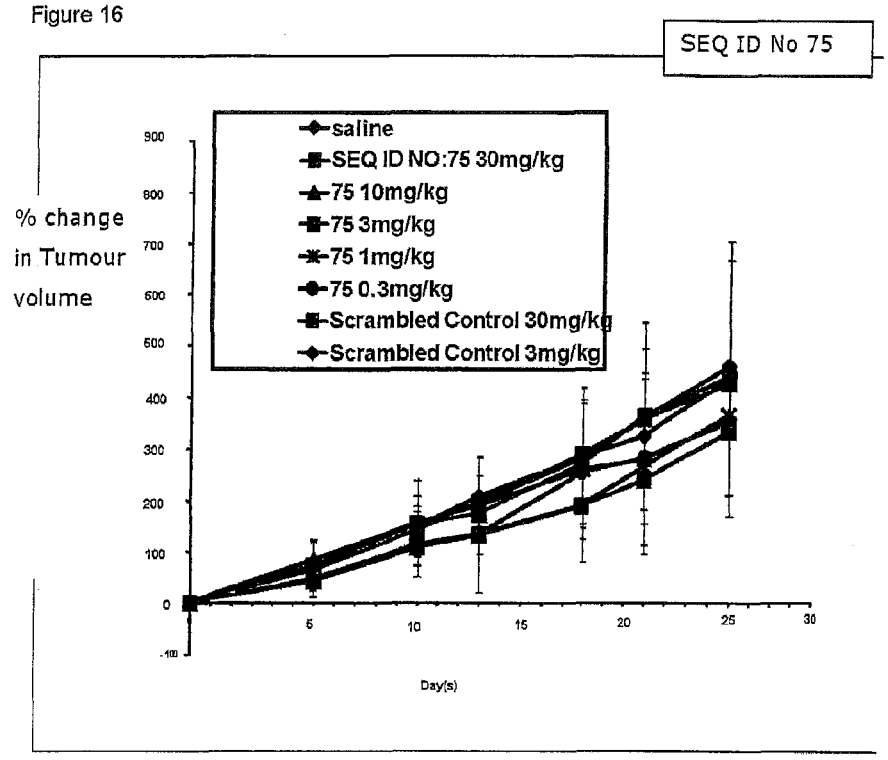
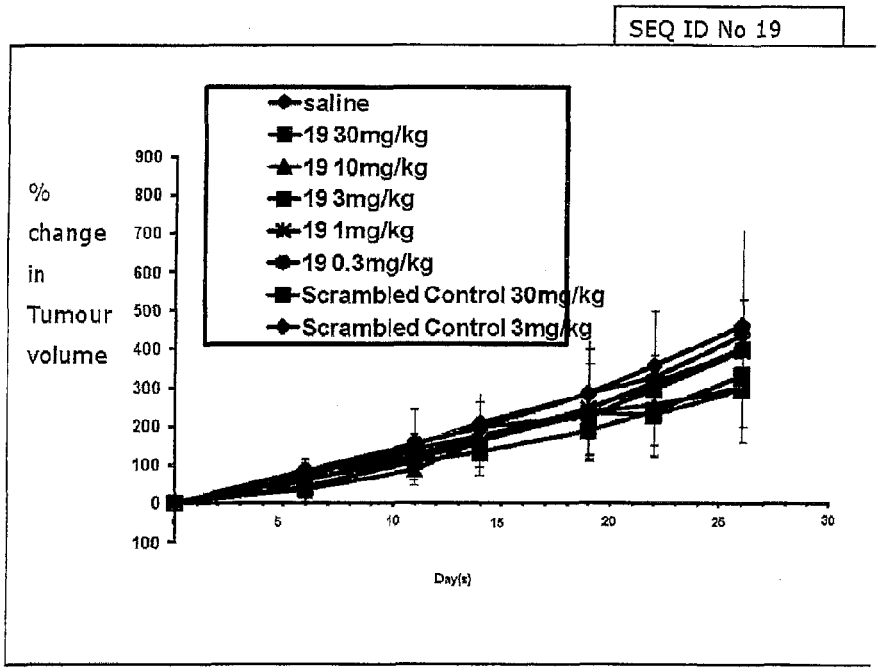

Figure 19
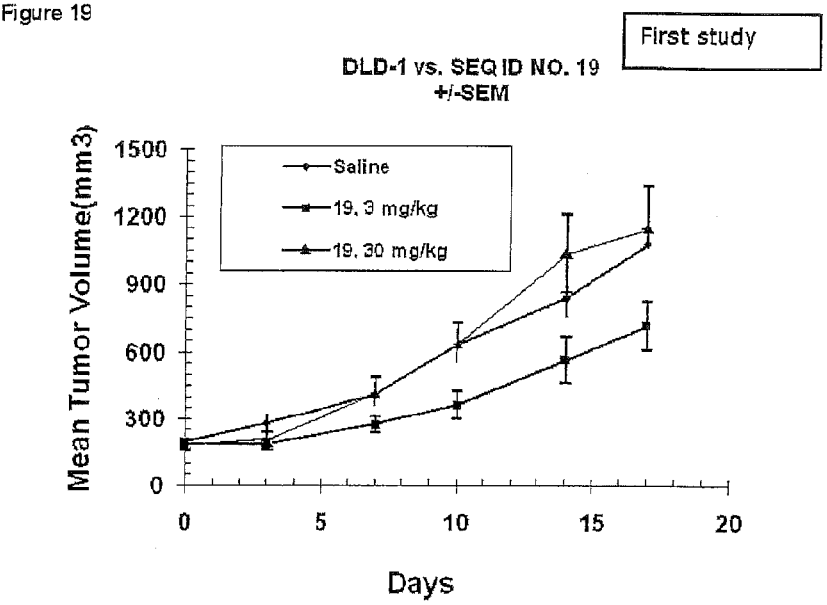
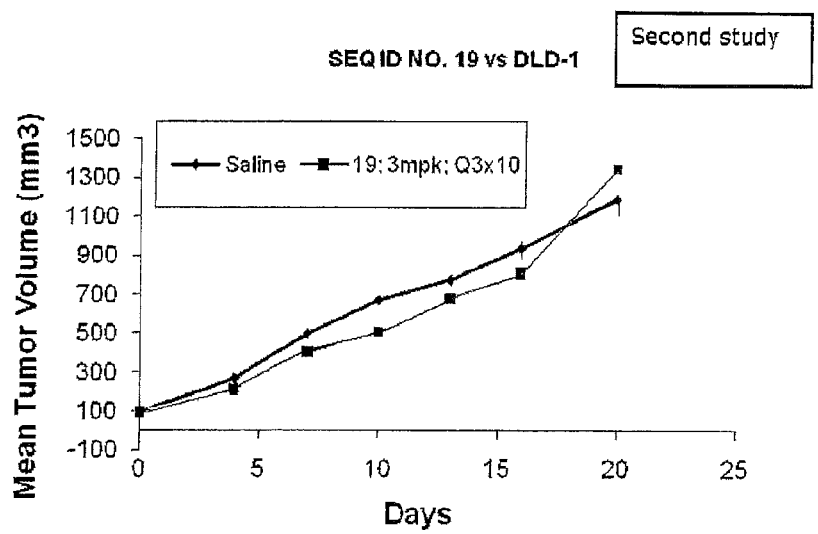

Figure 20b
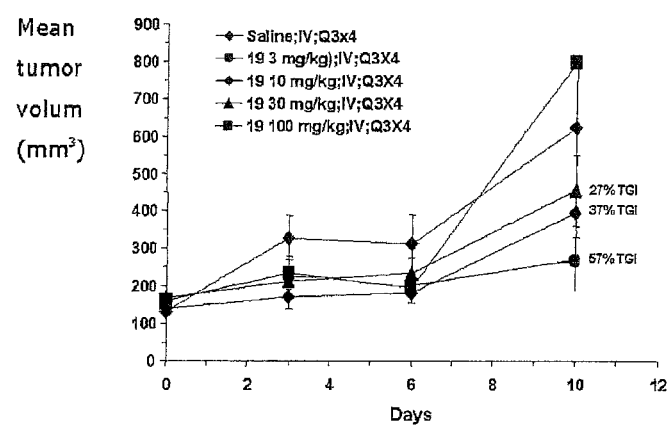
SEQ ID No 19
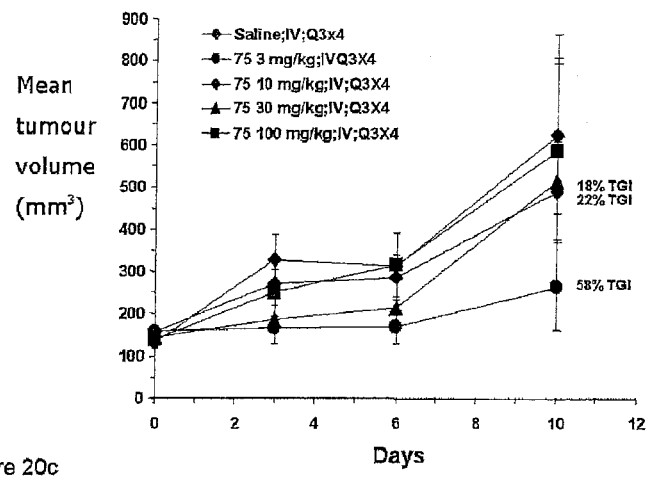
Figure 20c
SEQ ID No 75

RNA ANTAGONISTS TARGETING GLI2 FOR THE TREATMENT OF LEUKEMIA

This application is the U.S. national stage under 35 USC §371 of International Application Number PCT/US2010/021121, filed on Jan. 15, 2010, which claims priority to PCT Application No. PCT/IB2009/006407, filed on Jul. 15, 2009, the entire contents of which is hereby incorporated by reference.

FIELD OF INVENTION

The invention provides compounds, compositions and methods for modulating the expression of GLI2. In particular, this invention relates to oligomeric compounds (oligomers), which target GLI2 mRNA in a cell, leading to reduced expression of GLI2. Reduction of GLI2 expression is beneficial for a range of medical disorders, such as cancer.

BACKGROUND

Glioma-Associated Oncogene 2 (GLI2) is a member of the GLI zinc finger-containing transcription factors, which are involved in cell-fate determination, proliferation and patterning in many cell types and most organs. The human GLI2 mRNA is known to undergo alternative splicing to create alternative splice variants. Transgenic mice over-expressing GLI2 in cutaneous keratinocytes develop multiple basal cell carcinomas, indicating a GLI2 role in the development of these carcinomas.

U.S. Pat. No. 6,440,739 and WO03/008545 disclose a range of 2'-methoxyethyl-modified chimerical antisense oligonucleotides targeting GLI2, and indicate that these may be useful in the treatment of diseases associated with GLI2 expression. Kim et al., 2007, Cancer Res. 67(8) 3583-3593 reports on 2'-methoxyethyl-modified chimerical antisense oligonucleotides which were used to specifically down-regulate GLI2 and decrease proliferation of hepatocellular carcinoma cells in vitro.

There is a need for improved oligomers targeting GLI2. There is also a need for oligomers targeting both GLI1 and GLI2.

Furthermore, there is a continuing need for new and improved approaches for treating and preventing acute myeloid leukemia and preleukemic disorders which is addressed by the present invention.

SUMMARY OF INVENTION

The invention provides an oligomer of from 10-50 monomers, such as 10-30 monomers, which comprises a contiguous sequence (a first region) of 10-50 monomers, such as 10-30 monomers, wherein the contiguous sequence (the first region) is at least 80% (e.g., 85%, 90%, 95%, 98%, or 99%) identical (homologous) to a region corresponding to a mammalian GLI2 and/or GLI1 and/or GLI3 gene or mRNA or to the reverse complement of a target region of a nucleic acid which encodes a mammalian GLI2 and/or GLI1 and/or GLI3, such as a mammalian GLI2 and/or GLI1 and/or GLI3 gene or mRNA, such as a nucleic acid having the sequence set forth in SEQ ID NO: 1 and/or SEQ ID NO: 2 and/or SEQ ID NO: 134, or naturally occurring variants thereof. Thus, for example, the oligomer hybridizes to a region of a single-stranded nucleic acid molecule having the sequence shown in SEQ ID NO: 1.

The invention provides an oligomer of from 10-50 monomers, such as 10-30 monomers, which comprises a contiguous sequence (a first region) of 10-50 monomers, such as 10-30 monomers, wherein the contiguous sequence (the first region) is at least 80% (e.g., 85%, 90%, 95%, 98%, or 99%) identical (homologous) to a region corresponding to a mammalian GLI2 and/or GLI1 and/or GLI3 gene or mRNA, or to the reverse complement of a target region of a nucleic acid which encodes a mammalian GLI2 and/or GLI1 and/or GLI3, such as a mammalian GLI2 and/or GLI1 and/or GLI3 gene or mRNA, such as a nucleic acid having the sequence set forth in SEQ ID NO: 1 and/or SEQ ID NO: 2 and/or SEQ ID NO: 134, or naturally occurring variants thereof; and wherein at least one monomer in the first region is a nucleoside analogue wherein the nucleoside analogue is a Locked Nucleic Acid (LNA) monomer. Thus, for example, the oligomer hybridizes to a region of a single-stranded nucleic acid molecule having the sequence shown in SEQ ID NO: 1.

The invention provides for a conjugate comprising the oligomer according to the invention, and at least one non-nucleotide or non-polynucleotide moiety covalently attached to the oligomer.

The invention provides for a pharmaceutical composition comprising the oligomer or the conjugate according to the invention, and a pharmaceutically acceptable diluent, carrier, salt or adjuvant.

The invention provides for the oligomer or the conjugate according to the invention, for use as a medicament, such as for the treatment of a disease or a medical disorder as disclosed herein, such as a hyperproliferative disorder, such as cancer or other hyperproliferative disorder.

The invention provides for the use of an oligomer or the conjugate according to the invention, for the manufacture of a medicament for the treatment of a disease or disorder as disclosed herein, such as a hyperproliferative disorder, such as cancer.

The invention provides for a method of treating, preventing or delaying progression to a disease or disorder as disclosed herein, such as a hyperproliferative disorder, such as cancer, the method comprising administering, e.g. an effective amount of, an oligomer, a conjugate or a pharmaceutical composition according to the invention to an animal suffering from or susceptible to the disease or disorder (such as a patient suffering from or susceptible to the disease or disorder). In a preferred embodiment, the hyperproliferative disorder is acute myeloid leukemia or preleukemia such as myelodysplastic syndrome or myeloproliferative disease.

The invention provides for a method of inducing apoptosis in a cell, said method comprising contacting the cell with an oligomer, a conjugate or a pharmaceutical composition according to the invention in an amount sufficient to trigger apoptosis, wherein said cell is expressing a GLI2 and/or GLI1 and/or GLI3 gene or mRNA.

In one embodiment, the disease or disorder or condition is associated with overexpression of GLI2 and/or GLI1 and/or GLI3 gene or mRNA.

The invention provides for a method for the inhibition of GLI2 and/or GLI1 and/or GLI3 in a cell which is expressing GLI2 and/or GLI1 and/or GLI3, the method comprising contacting the cell with an oligomer, or a conjugate according to the invention so as to affect the inhibition of GLI2 and/or GLI1 and/or GLI3 expression (e.g. to cause an inhibitory effect on GLI2 expression) in said cell.

The invention also relates to oligomers which target both GLI1 and GLI2, and therefore the invention further provides for a method for the inhibition of both GLI1 and GLI2 in a cell which is expressing GLI1 and GLI2 said method comprising contacting the cell with an oligomer, or a conjugate according to the invention so as to affect the inhibition of both GLI1 and GLI2 expression (e.g. to cause an inhibitory effect on both GLI1 and GLI2 expression) in said cell.

The invention provides an oligomer of from 10-50 monomers, which comprises a first region of 10-50 contiguous monomers, wherein the sequence of the first region is at least 80% identical to a region corresponding to a mammalian GLI2 and/or GLI1 and/or GLI3 gene or to the reverse complement of a target region of a nucleic acid which encodes a mammalian GLI2 and/or GLI1 and/or GLI3.

The invention further provides a conjugate comprising the oligomer according to the invention, which comprises at least one non-nucleotide or non-polynucleotide moiety ("conjugated moiety") covalently attached to the oligomer of the invention.

The invention provides for pharmaceutical compositions comprising an oligomer or conjugate of the invention, and a pharmaceutically acceptable diluent, carrier, salt or adjuvant.

The invention further provides for an oligomer according to the invention, for use in medicine.

The invention further provides for the use of the oligomer of the invention for the manufacture of a medicament for the treatment of one or more of the diseases referred to herein, such as a disease selected from the group consisting of hyperproliferative disorders, such as cancer, such as prostate cancer, glioma, colorectal cancer, melanoma, breast cancer, lung cancer, hepatocellular carcinoma, acute myeloid leukemia and preleukemia such as myelodysplastic syndrome and myeloproliferative disease.

The invention further provides for an oligomer according to the invention, for use for the treatment of one or more of the diseases referred to herein, such as a disease selected from the group consisting of hyperproliferative disorders, such as cancer, such as prostate cancer, glioma, colorectal cancer, melanoma, breast cancer, lung cancer, hepatocellular carcinoma, acute myeloid leukemia and preleukemia such as myelodysplastic syndrome and myeloproliferative disease.

One embodiment of the invention provides an oligomer of between 10-30 monomers in length, or a conjugate thereof, wherein said oligomer comprises a first region of contiguous sequence of a total of between 10-30 monomers, wherein said contiguous sequence is at least 80% identical to a region corresponding to a mammalian GLI2 gene or the reverse complement of a target region of a nucleic acid which encodes a mammalian GLI2, such as a mammalian GLI2 gene or mRNA, such as a nucleic acid having the sequence set forth in SEQ ID NO: 1 and/or SEQ ID NO: 2 and/or SEQ ID NO: 134, or a naturally occurring variant thereof, for use in the treatment or prevention of a leukemia, such as acute myeloid leukemia, in mammals such as human patients in need thereof. In a variation of these embodiments, the oligomer consists of said first region of contiguous sequence.

Another embodiment of the invention provides the use of an oligomer of between 10-30 monomers in length which comprises a first region of contiguous sequence of a total of between 10-30 monomers, wherein said contiguous sequence is at least 80% identical to a region corresponding to a mammalian GLI2 gene or the reverse complement of a target region of a nucleic acid which encodes a mammalian GLI2, such as a mammalian GLI2 gene or mRNA, such as a nucleic acid having the sequence set forth in SEQ ID NO: 1 and/or SEQ ID NO: 2 and/or SEQ ID NO: 134, or a naturally occurring variant thereof, in the preparation of a medicament for the treatment or prevention of a leukemia, such as acute myeloid leukemia, in mammals such as human patients in need thereof. A related embodiment of the invention provides the use of a conjugate of said oligomer in the preparation of a medicament for the treatment or prevention of acute myeloid leukemia in human patients in need thereof. In a variation of these embodiments, the oligomer consists of said first region of contiguous sequence.

Pharmaceutical and other compositions comprising an oligomer of the invention are also provided. Further provided are methods of down-regulating the expression of GLI2 and/or GLI1 and/or GLI3 in cells or tissues comprising contacting said cells or tissues, in vitro or in viva, with an effective amount of one or more of the oligomers, conjugates or compositions of the invention. Further provided are methods of down-regulating the expression of GLI1 and GLI2 in cells or tissues comprising contacting said cells or tissues, in vitro or in vivo, with an effective amount of one or more of the oligomers, conjugates or compositions of the invention.

Also disclosed are methods of treating an animal (a non-human animal or a human) suspected of having, or susceptible to, a disease or condition, associated with expression, or over-expression of GLI2 and/or GLI1 and/or GLI3 by administering to the non-human animal or human a therapeutically or prophylactically effective amount of one or more of the oligomers, conjugates or pharmaceutical compositions of the invention. Further, methods of using oligomers for the inhibition of expression of GLI2 and/or GLI1 and/or GLI3, and for treatment of diseases associated with activity of GLI2 and/or GLI1 and/or GLI3 are provided.

The invention provides for a method for treating a disease selected from the group consisting of: hyperproliferative disorders, such as cancer, such as prostate cancer, glioma, colorectal cancer, melanoma, breast cancer, lung cancer, hepatocellular carcinoma, acute myeloid leukemia and preleukemia such as myelodysplastic syndrome and myeloproliferative disease, the method comprising administering an effective amount of one or more oligomers, conjugates, or pharmaceutical compositions thereof to an animal in need thereof (such as a patient in need thereof).

The invention provides for methods of inhibiting (e.g., by down-regulating) the expression of GLI2 and/or GLI1 and/or GLI3 in a cell or a tissue, the method comprising the step of contacting the cell or tissue, in vitro or in vivo, with an effective amount of one or more oligomers, conjugates, or pharmaceutical compositions thereof, to effect down-regulation of expression of GLI2 and/or GLI1 and/or GLI3.

The invention provides for methods of inhibiting (e.g., by down-regulating) the expression of GLI1 and GLI2 in a cell or a tissue, the method comprising the step of contacting the cell or tissue, in vitro or in vivo, with an effective amount of one or more oligomers, conjugates, or pharmaceutical compositions thereof, to effect down-regulation of expression of GLI1 and GLI2.

One embodiment of the invention provides methods of inhibiting (e.g., by down-regulating) the expression of GLI2 in a leukemia cell (or cells), such as acute myeloid leukemia cell(s), or preleukemia cell (or cells), the method comprising the step of contacting the cell(s), in vitro or in vivo, with an effective amount of one or more oligomers, conjugates, or pharmaceutical compositions thereof, to effect down-regulation of expression of GLI2 by the cell(s). The cells may, for example, be non-human mammal cells or human cells.

BRIEF DESCRIPTION OF FIGURES

FIG. 1: Human GLI2 mRNA (cDNA) sequence (SEQ ID NO 1). GenBank accession number NM_005270.

FIG. 2: Human GLI1 mRNA (cDNA) sequence (SEQ ID NO 2). GenBank accession number NM_005269.

FIG. 3: Human GLI3 mRNA (cDNA) sequence (SEQ ID NO 134). GenBank accession number NM_000168.

FIGS. 15a and 15b: Anti-tumor effects of the oligomer having the sequence set forth in SEQ ID NO: 3, 19 or 75 in PC3 prostate cancer model. The SEQ ID No of the oligomer used is indicated above the bars of the graph. In the Figure legend, the relevant SEQ ID NO: precedes (but separated by a comma) the respective amount. Thus, and by way of example, "3.3 mg/kg" for G2 represents 3 mg/kg of SEQ ID NO: 3.

FIG. 16: Tumor growth inhibition (TGI) of oligomers having the sequence set forth in SEQ ID NO: 19, or SEQ ID NO: 75 in a DU-145 prostate cancer model. In the key to the graphs, "Scrambled Control" refers to scrambled control oligomer for survivin; and "19" refers to SEQ ID No 19 (e.g. "19 30 mg/kg" refers to 30 mg/kg of SEQ ID No 19).

FIG. 19: Efficacy study (tumor growth inhibition) of the oligomer having the sequence set forth in SEQ ID NO: 19 in DLD-1 colorectal cancer model. In the key to the graph, "19" refers to SEQ ID No 19; "mpk" refers to mg/kg; "Q3×10" refers to 10 doses every third day; e.g. "19; 3 mpk; Q3×4" refers to 4 doses every third day of 3 mg/kg of SEQ ID No 19.

DETAILED DESCRIPTION OF INVENTION

The Oligomer

Figure 4:
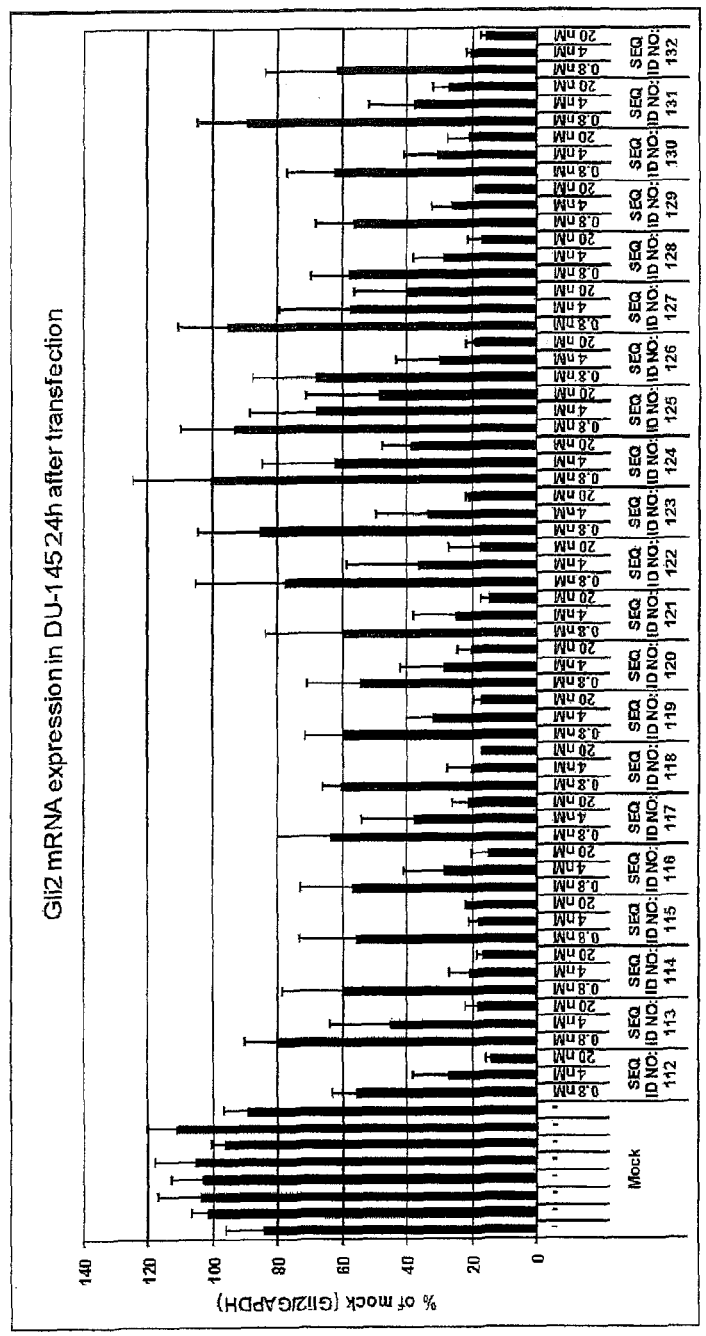
FIG. 4: GLI2 mRNA expression in DU-145 cells after transfection with GLI2 oligomers. The data have been normalised with GAPDH mRNA expression and are compared to target expression in mock (100%). Mock transfected cells are transfected with the transfection agent only (negative control).

The invention employs oligomeric compounds (referred herein as oligomers), for use in modulating the function of nucleic acid molecules encoding mammalian GLI2 and/or GLI1 and/or GLI3 (such as the GLI2 nucleic acid shown in SEQ ID NO: 1; or the GLI2 nucleic acid shown in SEQ ID NO: 2; or such as the GLI2 nucleic acid shown in SEQ ID NO: 134), and naturally occurring variants of such nucleic acid molecules. The term "oligomer" in the context of the invention, refers to a molecule formed by covalent linkage of two or more monomers (i.e. an oligonucleotide). In some embodiments, the oligomer comprises or consists of from 10-50 covalently linked monomers, such as from 10-30 covalently linked monomers, such as 10-24 covalently linked monomers, such as 10-18 covalently linked monomers, such as 10-16 covalently linked monomers.

In some embodiments, the terms "nucleoside", "nucleotide", "unit" and "monomer" are used interchangeably. It will be recognised that when referring to a sequence of nucleotides or monomers, what is referred to is the sequence of bases, such as A, T, G, C or U.

The term "nucleotide" as used herein, refers to a glycoside comprising a sugar moiety, a base moiety and a covalently linked group (linkage group) such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In the field of biochemistry, the term "nucleoside" is commonly used to refer to a glycoside comprising a sugar moiety and a base moiety, and may therefore be used when referring to the "nucleotide" units, which are covalently linked by the internucleotide linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refers to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

The person having ordinary skill in the art would understand that, in the context of the present invention, the 5' terminal nucleotide of an oligonucleotide (oligomer) does not comprise a 5' internucleotide linkage group, although it may or may not comprise a 5' terminal group.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified nucleobase (base) moiety (i.e., the purine and pyrimidine heterocycles adenine, guanine, cytosine, thymine or uracil) and "nucleoside analogues," which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer," "locked monomer," or "LNA monomer" is a nucleoside analogue having a bicyclic sugar, as further described herein below.

The terms "corresponding to" and "corresponds to" refer to the comparison between the nucleotide/nucleoside sequence (i.e. the nucleobase or base sequence) of the oligomer or contiguous nucleotide/nucleoside sequence (a first region) and the equivalent contiguous nucleotide/nucleoside sequence of a further sequence selected from either i) a subsequence of the reverse complement of the nucleic acid target, and/or ii) the sequence of nucleotides/nucleosides provided herein. Nucleotide/nucleoside analogues are compared directly to their equivalent or corresponding nucleotides/nucleosides. A first region which corresponds to a further sequence under i) or ii) typically is identical to that sequence over the length of the first region (such as the contiguous nucleotide/nucleoside sequence) or, as described herein may, in some embodiments, be at least 80% homologous to a corresponding sequence, such as at least 85%, at least 90%, at least 91%, at least 92%, at least 93%, at least 94%, at least 95%, at least 96% homologous, at least 97% homologous, at least 98% homologous, at least 99% homologous, such as 100% homologous (identical).

The terms "corresponding nucleoside analogue" and "corresponding nucleoside" indicate that the base moiety in the nucleoside analogue and the base moiety in the nucleoside are identical. For example, when the "nucleoside" contains a 2'-deoxyribose sugar linked to an adenine, the "corresponding nucleoside analogue" contains, for example, a modified sugar linked to an adenine base moiety.

The terms "oligomer", "oligomeric compound" and "oligonucleotide" are used interchangeably in the context of the invention, and refer to a molecule formed by covalent linkage of two or more monomers by, for example, a phosphate group (forming a phosphodiester linkage between nucleosides) or a phosphorothioate group (forming a phosphorothioate linkage between nucleosides). The oligomer consists of, or comprises, 10-50 monomers, such as 10-30 monomers, such as 10-24 monomers, such as 10-18 monomers, such as 10-16 monomers. The oligomer consists of or comprises a first region (a contiguous sequence) which, for example, consists of 9-30 contiguous monomers, such as 9-24 monomers, such as 9-18 monomers, such as 9-16 monomers.

In some embodiments, the terms "contiguous sequence", "contiguous monomers" and "region" are interchangeable.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases and high affinity and specificity for the nucleic acid target. LNA monomers are particularly preferred, for example, for conferring one or more of the above-mentioned properties.

In various embodiments, one or more nucleoside analogues present within the oligomer are "silent" or "equivalent" in function to the corresponding natural nucleoside, i.e., have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example, by producing increased binding affinity to the target region of the target nucleic acid and/or increased resistance to nucleases, such as intracellular nucleases, and/or increased ease of transport into the cell.

Thus, in various embodiments, oligomers according to the invention comprise nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the oligomers of the invention, the term "at least one" includes the terms "at least two" and "at least three" and "at least four." Likewise, in some embodiments, the term "at least two" comprises the terms "at least three" and "at least four."

In some embodiments, the oligomer comprises or consists of 9, 10, 11, 12, 13, 14, 15, 16, 17, 18, 19, 20, 21, 22, 23, 24, 25, 26, 27, 28, 29 or 30 contiguous monomers in the first region.

In some embodiments, the oligomer comprises or consists of 10-24 contiguous monomers, such as 10-22 contiguous monomers, such as 10-18 contiguous monomers, such as 10-16 contiguous monomers, such as 12-18 contiguous monomers, such as 13-17 or 12-16 contiguous monomers, such as 13, 14, 15, 16 or 24 contiguous monomers. It should be understood that when a range is given for an oligomer, or contiguous nucleotide sequence length it includes the lower and upper lengths provided in the range, for example from (or between) 10 30, includes both 10 and 30.

In certain embodiments, the oligomer comprises or consists of 10, 11, 12, 13, or 14 contiguous monomers.

In various embodiments, the oligomer according to the invention consists of no more than 24 monomers, such as no more than 22 monomers, such as no more than 20 monomers, such as no more than 18 monomers, such as 15, 16 or 17 monomers. In some embodiments, the oligomer of the invention comprises less than 20 monomers.

In various embodiments, the oligomers of the invention do not comprise RNA monomers.

In various embodiments, the oligomers according to the invention are linear molecules or are linear as synthesised. The oligomer, in such embodiments, is a single stranded molecule, and typically does not comprise short regions of, for example, at least 3, 4 or 5 contiguous monomers, which are complementary to another region within the same oligomer such that the oligomer forms an internal duplex. In some embodiments, the oligomer is essentially not double stranded, i.e., is not a siRNA.

In some embodiments, the oligomer of the invention consists of a contiguous stretch of monomers (a first region), the sequence of which is identified by a SEQ ID NO disclosed herein (see, e.g., Tables 1-3). In other embodiments, the oligomer comprises a first region, the region consisting of a contiguous stretch of monomers of the nucleic acid molecule encoding the target, and one or more additional regions which consist of at least one additional monomer. In some embodiments, the sequence of the first region is identified by a SEQ ID NO disclosed herein.

Gapmer Design

Typically, the oligomer of the invention is a gapmer.

A "gapmer" is an oligomer which comprises a contiguous stretch of monomers capable of recruiting an RNAse (e.g., such as RNAseH) as further described herein below, such as a region of at least 6 or 7 DNA monomers, referred to herein as region B. Region B is flanked both on its 5' and 3' ends by regions respectively referred to as regions A and C, each of regions A and C comprising or consisting of nucleoside analogues, such as affinity-enhancing nucleoside analogues, such as 1-6 nucleoside analogues. The RNase is preferably RNaseH, such as *E. coli* or human RNaseH. The capability of an oligomer to recruit RNaseH is determined when the oligomer is formed in a duplex with a complementary RNA molecule (such as a mRNA target).

In some embodiments, the monomers which are capable of recruiting RNAse are selected from the group consisting of DNA monomers, alpha-L-LNA monomers, C4' alkylated DNA monomers (see PCT/EP2009/050349 and Vester et al., Bioorg. Med. Chem. Lett. 18 (2008) 2296-2300, hereby incorporated by reference), and UNA (unlocked nucleic acid) nucleotides (see Fluiter et al., Mol. Biosyst., 2009, 10, 1039 hereby incorporated by reference). UNA is unlocked nucleic acid, typically where the C2'-C3' bond (i.e. the covalent carbon-carbon bond between the C2' and C3' carbons) of the sugar has been removed, forming an unlocked "sugar" residue.

Typically, the gapmer comprises regions, from 5' to 3', A-B-C, or optionally A-B-C-D or D-A-B-C, wherein: region A (A) consists of or comprises at least one nucleoside analogue, such as at least one LNA monomer, such as 1-6 contiguous nucleoside analogues, such as LNA monomers, and region B (B) consists of or comprises at least five contiguous monomers which are capable of recruiting RNAse (when formed in a duplex with a complementary target region of the target RNA molecule, such as the mRNA target), such as DNA monomers; region C (C) consists of or comprises at least one nucleoside analogue, such as at least one LNA monomer, such as 1-6 contiguous nucleoside analogues, such as LNA monomers; and region D (D), when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers (e.g. consecutive nucleotides) which are capable of recruiting RNAse, such as RNaseH, or 6-10, or 7-9 contiguous monomers, such as 10 or 9 or 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In various embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 monomers, such as DNA monomers.

Further gapmer designs are disclosed in WO2004/046160, which is hereby incorporated by reference.

WO2008/113832 (which claims priority from U.S. provisional application 60/977,409) hereby incorporated by reference, refers to 'shortmer' gapmer oligomers. In some embodiments, oligomers presented here may be such shortmer gapmers.

In certain embodiments, the oligomer consists of 10, 11, 12, 13, 14, 15 or 16 monomers, wherein the regions of the oligomer have the pattern (5'-3'), A-B-C, or optionally A-B-C-D or D-A-B-C, wherein: region A consists of 1, 2 or 3 nucleoside analogue monomers, such as LNA monomers; region B consists of 7, 8, 9 or 10 contiguous monomers which are capable of recruiting RNAse, such as RNaseH; and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers. In certain embodiments, region B consists of 8 nucleoside monomers. In certain embodiments, region B consists of 9 nucleoside monomers. In certain embodiments, region B consists of 10 nucleoside monomers. In certain embodiments, region B comprises 1-10 DNA monomers, such as 2, 3, 4, 5, 6, 7, 8 or 9 DNA monomers. In certain embodiments, region B comprises 1-9 DNA monomers, such as 2, 3, 4, 5, 6, 7 or 8 DNA monomers. In certain embodiments, region B consists of DNA monomers. In certain embodiments, region B comprises at least one LNA monomer which is in the alpha-L configuration, such as 2, 3, 4, 5, 6, 7, 8, 9 or 10 LNA monomers in the alpha-L-configuration. In certain embodiments, region B comprises at least one alpha-L-oxy LNA monomer. In certain embodiments, all the LNA monomers in region B that are in the alpha-L-configuration are alpha-L-oxy LNA units. In certain embodiments, the number of monomers present in the A-B-C regions, respectively, are selected from the group consisting of (nucleoside analogue monomers-region B-nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 3-9-3, 4-9-1, 1-9-4, or; 1-10-1, 1-10-2, 2-10-1, 2-10-2, 1-10-3, 3-10-1, 2-10-3, 3-10-2, or 3-10-3. In certain embodiments, the number of monomers present in the A-B-C regions of the oligomer of the invention respectively is selected from the group consisting of: 2-7-1, 1-7-2, 2-7-2, 3-7-3, 2-7-3, 3-7-2, 3-7-4, and 4-7-3. In certain embodiments, each of regions A and C consists of three LNA monomers, and region B consists of 8 or 9 or 10 nucleoside monomers, preferably DNA monomers. In certain embodiments, each of regions A and C consists of two LNA monomers, and region B consists of 8 or 9 nucleoside monomers, preferably DNA monomers.

In various embodiments, other gapmer designs include those where region A and/or C consists of 3, 4, 5 or 6 nucleoside analogues, such as monomers containing a 2'-O-methoxyethyl-ribose sugar (2'-MOE) or monomers containing a 2'-fluoro-deoxyribose sugar, and region B consists of 8, 9, 10, 11 or 12 nucleosides, such as DNA monomers, where regions A-B-C have 3-9-3, 3-10-3, 5-10-5 or 4-12-4 monomers. Further gapmer designs are disclosed in WO 2007/146511A2, hereby incorporated by reference.

Internucleoside Linkages

The monomers of the oligomers described herein are coupled together via linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" and "internucleoside linkage" mean a group capable of covalently coupling together two contiguous monomers. Specific and preferred examples include phosphate groups (forming a phosphodiester between adjacent nucleoside monomers) and phosphorothioate groups (forming a phosphorothioate linkage between adjacent nucleoside monomers).

Suitable linkage groups include those listed in WO2007/031091, for example in the first paragraph of page 34 of WO2007/031091 (hereby incorporated by reference).

It is, in various embodiments, preferred to modify the linkage group from its normal phosphodiester to one that is more resistant to nuclease attack, such as phosphorothioate or boranophosphate—these two being cleavable by RNase H, thereby permitting RNase-mediated antisense inhibition of expression of the target gene.

In some embodiments, suitable sulphur (S) containing linkage groups as provided herein are preferred. In various embodiments, phosphorothioate linkage groups are preferred, particularly for the gap region (B) of gapmers. In certain embodiments, phosphorothioate linkages are used to link together monomers in the flanking regions (A and C). In various embodiments, phosphorothioate linkages are used for linking regions A or C to region D, and for linking together monomers within region D.

In various embodiments, regions A, B and C comprise linkage groups other than phosphorothioate, such as phosphodiester linkages, particularly, for instance when the use of nucleoside analogues protects the linkage groups within regions A and C from endo-nuclease degradation—such as when regions A and C comprise LNA monomers.

In various embodiments, adjacent monomers of the oligomer are linked to each other by means of phosphorothioate groups.

It is recognised that the inclusion of phosphodiester linkages, such as one or two linkages, into an oligomer with a phosphorothioate backbone, particularly with phosphorothioate linkage groups between or adjacent to nucleoside analogue monomers (typically in region A and/or C), can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such as those provided herein, it will be understood that, in various embodiments, when the linkages are phosphorothioate linkages, alternative linkages, such as those disclosed herein may be used, for example phosphate (phosphodiester) linkages may be used, particularly for linkages between nucleoside analogues, such as LNA monomers. Likewise, in various embodiments, when referring to specific gapmer oligonucleotide sequences, such as those provided herein, when one or more monomers in region A or C, such as LNA monomers, comprises a 5-methylcytosine base, other monomers in that region may contain unmodified cytosine bases.

Target Nucleic Acid

The terms "nucleic acid" and "polynucleotide" are used interchangeably herein, and are defined as a molecule formed by covalent linkage of two or more monomers, as above-described. Including 2 or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

In some embodiments, the term "target nucleic acid", as used herein, refers to DNA or RNA (e.g., mRNA or pre-mRNA) encoding a mammalian GLI2 polypeptide, such as human GLI2, such as the nucleic acid having the sequence shown in SEQ ID NO: 1, and naturally occurring allelic variants of such nucleic acids. In certain embodiments, the mammalian GLI2 is a mouse GLI2.

In some embodiments, the term "target nucleic acid", as used herein, refers to DNA or RNA (e.g., mRNA or pre-mRNA) encoding a mammalian GLI1 polypeptide, such as human GLI1, such as the nucleic acid having the sequence shown in SEQ ID NO: 2, and naturally occurring allelic variants of such nucleic acids. In certain embodiments, the mammalian GLI1 is a mouse GLI1.

In some embodiments, the term "target nucleic acid", as used herein, refers to DNA or RNA (e.g., mRNA or pre-mRNA) encoding a mammalian GLI3 polypeptide, such as human GLI3, such as the nucleic acid having the sequence shown in SEQ ID NO: 134, and naturally occurring allelic variants of such nucleic acids. In certain embodiments, the mammalian GLI3 is a mouse GLI3.

In some embodiments, for example when used in research or diagnostics, the "target nucleic acid" is a cDNA or a synthetic oligonucleotide derived from the above DNA or RNA nucleic acid targets. The oligomers according to the invention are typically capable of hybridising to the target nucleic acid.

Exemplary target nucleic acids include mammalian GLI2-encoding nucleic acids having the GenBank Accession numbers shown in the table below, along with their corresponding protein sequences:

|  | GenBank Accession Number Nucleic acid (mRNA/cDNA sequence) | GenBank Accession Number Polypeptide (deduced) |
|---|---|---|
| Human | NM_005270 version 4 (SEQ ID No 1) | NP_005261 version 2 |
| Mouse | NM_001081125 version 1 | NP_001074594 version 1 |

Exemplary target nucleic acids include mammalian GLI1-encoding nucleic acids having the GenBank Accession numbers shown in the table below, along with their corresponding protein sequences:

|  | GenBank Accession Number Nucleic acid (mRNA/cDNA sequence) | GenBank Accession Number Polypeptide (deduced) |
|---|---|---|
| Human | NM_005269 version 1 (SEQ ID No 2) | NP_005260 version 1 |
| Mouse | NM_010296 version 2 | NP_034426 version 2 |
| Rhesus monkey | XM_001116072 version 1 | XP_001116072 version 1 |

Exemplary target nucleic acids include mammalian GLI3-encoding nucleic acids having the GenBank Accession numbers shown in the table below, along with their corresponding protein sequences:

|  | GenBank Accession Number Nucleic acid (mRNA/cDNA sequence) | GenBank Accession Number Polypeptide (deduced) |
|---|---|---|
| Human | NM_000168 version 4 (SEQ ID No 134) | NP_000159 version 3 |
| Mouse | NM_008130 version 2 | NP_032156 version 2 |
| Rhesus monkey | XM_001098108 version 1 | XP_001098108 version 1 |

It is recognised that the above-disclosed GenBank Accession numbers for nucleic acids refer to cDNA sequences and not to mRNA sequences per se. The sequence of a mature mRNA can be derived directly from the corresponding cDNA sequence with thymine bases (T) being replaced by uracil bases (U).

The term "naturally occurring variant thereof" refers to variants of the GLI2 and/or GLI1 and/or GLI3 polypeptide or nucleic acid sequence which exist naturally within the defined taxonomic group, such as mammals, such as mouse, monkey, and preferably human; preferably GLI2. Typically, when referring to "naturally occurring variants" of a GLI2 polynucleotide the term also encompasses any allelic variant of the GLI2 encoding genomic DNA which is found at human Chromosome 2; location 2q14 by chromosomal translocation or duplication, and the RNA, such as mRNA derived therefrom. Typically, when referring to "naturally occurring variants" of a GLI1 polynucleotide the term also encompasses any allelic variant of the GLI1 encoding genomic DNA which is found at human Chromosome 12; location 12q13.2-q13.3 by chromosomal translocation or duplication, and the RNA, such as mRNA derived there from. Typically, when referring to "naturally occurring variants" of a GLI3 polynucleotide the term also encompasses any allelic variant of the GLI 3 encoding genomic DNA which is found at human Chromosome 7; location 7p13 by chromosomal translocation or duplication, and the RNA, such as mRNA derived there from. "Naturally occurring variants" may also include variants derived from alternative splicing of the GLI2 and/or GLI1 and/or GLI3 mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

In certain embodiments, oligomers described herein bind to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Such binding is also referred to as "hybridisation." Unless otherwise indicated, binding is by Watson-Crick pairing of complementary bases (i.e., adenine with thymine (DNA) or uracil (RNA), and guanine with cytosine), and the oligomer binds to the target region because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" (homology) to the reverse complement of the sequence of the target region.

The terms "reverse complement", "reverse complementary" and "reverse complementarity" as used herein are interchangeable with the terms "complement", "complementary" and "complementarity".

Unless otherwise made clear by context, the "target region" herein will be the region of the target nucleic acid having the sequence that best aligns with the reverse complement of the sequence of the specified oligomer (or region thereof), using the alignment program and parameters described herein below.

In determining the degree of "complementarity" between oligomers of the invention (or regions thereof) and the target region of the nucleic acid which encodes mammalian GLI2 and/or GLI1 and/or GLI3, such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

As used herein, the terms "homologous" and "homology" are interchangeable with the terms "identity" and "identical".

Amino acid and polynucleotide alignments, percentage sequence identity, and degree of complementarity may be determined for purposes of the invention using the ClustalW algorithm using standard settings: see http://www.ebi.ac.uk/emboss/align/index.html, Method: EMBOSS::water (local): Gap Open=10.0, Gap extend=0.5, using Blosum 62 (protein), or DNAfull for nucleotide/nucleobase sequences.

As will be understood, depending on context, "mismatch" refers to a non-identity in sequence (as, for example, between the nucleobase sequence of an oligomer and the reverse complement of the target region to which it binds; as for example, between the base sequence of two aligned GLI2 encoding nucleic acids), or to noncomplementarity in sequence (as, for example, between an oligomer and the target region to which it binds).

In some embodiments, the oligomers according to the invention are capable of inhibiting (such as, by down-regulating) the expression of one or more GLI2 target genes in a cell which is expressing, or is capable of expressing (i.e. by alleviating GLI2 repression of the GLI2 target gene in a cell) a GLI2 target gene.

The oligomers which target GLI2 mRNA, may hybridize to any site along the target mRNA nucleic acid, such as the 5' untranslated leader, exons, introns and 3' untranslated tail. However, it is preferred that the oligomers which target GLI2 mRNA hybridise to the mature mRNA form of the target nucleic acid.

The oligomers which target GLI1 mRNA, may hybridize to any site along the target mRNA nucleic acid, such as the 5' untranslated leader, exons, introns and 3' untranslated tail. However, it is preferred that the oligomers which target GLI1 mRNA hybridise to the mature mRNA form of the target nucleic acid.

The oligomers which target GLI3 mRNA, may hybridize to any site along the target mRNA nucleic acid, such as the 5' untranslated leader, axons, introns and 3'untranslated tail. However, it is preferred that the oligomers which target GLI3 mRNA hybridise to the mature mRNA form of the target nucleic acid.

In some embodiments, the oligomers according of the invention do not target GLI3 mRNA.

Suitably, the oligomer of the invention or conjugate thereof is capable of down-regulating (e.g. reducing or removing) expression of the GLI2 gene. In various embodiments, the oligomer (or conjugate) of the invention can effect the inhibition of GLI2, typically in a mammalian cell, such as a human cell. In certain embodiments, the oligomers of the invention, or conjugates thereof, bind to the target nucleic acid and affect inhibition of GLI2 mRNA expression of at least 10% or 20% compared to the expression level in the absence of the oligomer(s) or conjugate(s), more preferably of at least 30%, 40%, 50%, 60%, 70%, 80%, 90% or 95% as compared to the GLI2 expression level in the absence of the oligomer(s) or conjugate(s).

Suitably, the oligomer of the invention or conjugate thereof is capable of down-regulating (e.g. reducing or removing) expression of the GLI1 gene. In various embodiments, the oligomer (or conjugate) of the invention can effect the inhibition of GLI1, typically in a mammalian cell, such as a human cell. In certain embodiments, the oligomers of the invention, or conjugates thereof, bind to the target nucleic acid and affect inhibition of GLI1 mRNA expression of at least 10% or 20% compared to the expression level in the absence of the oligomer(s) or conjugate(s), more preferably of at least 30%, 40%, 50%, 60%, 70%, 80%, 90% or 95% as compared to the GLI1 expression level in the absence of the oligomer(s) or conjugate(s).

Suitably, the oligomer of the invention or conjugate thereof is capable of down-regulating (e.g. reducing or removing) expression of the GLI3 gene. In various embodiments, the oligomer (or conjugate) of the invention can effect the inhibition of GLI3, typically in a mammalian cell, such as a human cell. In certain embodiments, the oligomers of the invention, or conjugates thereof, bind to the target nucleic acid and affect inhibition of GLI3 mRNA expression of at least 10% or 20% compared to the expression level in the absence of the oligomer(s) or conjugate(s), more preferably of at least 30%, 40%, 50%, 60%, 70%, 80%, 90% or 95% as compared to the GLI3 expression level in the absence of the oligomer(s) or conjugate(s).

In some embodiments, such inhibition is seen when using from about 0.04 nM to about 25 nM, such as from about 0.8 nM to about 20 nM of the oligomer or conjugate. As illustrated herein the cell type is, in some embodiments, a human cell, such as a cancer cell, such as a human colorectal cancer cell, a human glioma cell, a human hepatocellular carcinoma cell, a human melanoma cell, a human breast cancer cell, a human lung cancer cell or a human prostate cancer cell (e.g. in vitro—transfected cells). The oligomer concentration used is, in some embodiments, 5 nM. The oligomer concentration used is, in some embodiments 25 nM. The oligomer concentration used is, in some embodiments 1 nM. It should be noted that the concentration of oligomer used to treat the cell is in various typical embodiments performed in an in vitro cell assay, using transfection (Lipofecton), as illustrated in the Examples. In the absence of a transfection agent, the oligomer concentration required to obtain the down-regulation of the target is typically from 1 µM to 25 µM, such as 5 µM.

In various embodiments, the inhibition of mRNA expression is less than 100% (i.e., less than complete inhibition of expression), such as less than 98% inhibition, less than 95% inhibition, less than 90% inhibition, less than 80% inhibition, such as less than 70% inhibition. In various embodiments, modulation of gene expression can be determined by measuring protein levels, e.g. by methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from about 0.04 nM to about 25 nM, such as from about 0.8 nM to about 20 nM, is, in various embodiments, typically to a level of 10-20% of the normal levels in the absence of the oligomer, conjugate or composition of the invention.

The invention therefore provides a method of down-regulating or inhibiting the expression of GLI2 protein and/or mRNA in a cell which is expressing GLI2 protein and/or mRNA, the method comprising contacting the cell with an effective amount of the oligomer or conjugate according to the invention to down-regulate or inhibit the expression of the GLI2 protein and/or mRNA in the cell.

The invention provides a method of down-regulating or inhibiting the expression of GLI1 protein and/or mRNA in a cell which is expressing GLI1 protein and/or mRNA, the method comprising contacting the cell with an effective amount of the oligomer or conjugate according to the invention to down-regulate or inhibit the expression of the GLI1 protein and/or mRNA in the cell.

The invention provides a method of down-regulating or inhibiting the expression of GLI3 protein and/or mRNA in a cell which is expressing GLI3 protein and/or mRNA, the method comprising contacting the cell with an effective amount of the oligomer or conjugate according to the invention to down-regulate or inhibit the expression of the GLI3 protein and/or mRNA in the cell.

Suitably the cell is a mammalian cell, such as a human cell. The contacting may occur, in some embodiments, in vitro. The contacting may occur, in some embodiments, in vivo.

Oligomers with the nucleobase sequence shown in SEQ ID NO 3, 4, 5, 6, 7, 8, 9, 10, 11, 12, 13, 14, 15, 85, 86 (all sequence motifs) and SEQ ID NO 91, 92 and 93 (designs) and SEQ ID NO 112, 113 and 114 (compounds) target both GLI1 and GLI2.

The invention provides a method for the preparation of oligomers for the treatment of hyperproliferative disorders, such as cancer, or for the down-regulation of GLI1 and GLI2 (and optionally GLI3) in a cell which is expressing both GLI1 and GLI2 (and optionally GLI3), said method comprising selecting a region of homology between the human GLI1 and GLI2 mRNA sequences, providing an oligomer with a nucleobase sequence that is the reverse complement of said region of homology, and preparing an oligomer according to the invention, wherein the nucleobase sequence of the oligomer has no more than 1 or 2 mismatches to the corresponding region of either the GLI1 or GLI2 mRNA target. The region of homology may therefore comprise 1 or 2 mismatches to the corresponding region of the GLI1 and/or GLI2 mRNA sequences, preferably 1 or even no mismatches. The region of homology may be as long as the oligomer of the invention. In some aspects, said method may further comprise the selection of a region of homology, wherein said region has at least 2, such as at least three or at least four mismatches with the corresponding region of GLI3 mRNA. Alternatively, said method may further comprise the selection of a region of homology, wherein said region has no more than 2, such as 1 or even no mismatches with the corresponding region of GLI3 mRNA.

In certain embodiments, target regions of SEQ ID NO: 1 include those regions which have sequences that are a perfect match between human GLI1 and human GLI2—or a subsequence thereof—such as a target region selected from the group consisting of the following regions of the human GLI2 mRNA transcript, the sequence of which is set forth in SEQ ID NO 1: 1) nucleotides 909-926, 2) nucleotides 933-948, 3) nucleotides 1542-1555, 4) nucleotides 1568-1586, 5) nucleotides 1647-1663, 6) nucleotides 1695-1708, 7) nucleotides 1789-1809, and 8) nucleotides 1839-1855.

In some embodiments, target regions of SEQ ID NO: 1 include those regions which have sequences that are a perfect match between human GLI1 and human GLI2—or a subsequence thereof.

In various embodiments, target regions of SEQ ID NO: 1 include those regions which have sequences that are a perfect match between human GLI1, human GLI2 and human GLI3—or a subsequence thereof.

It is preferred that the oligomers of the invention do not target exons 1-5 (i.e. nucleotides 1-831 of SEQ ID NO: 1) due to alternative splice variants of GLI2, which occur in the first five exons. Therefore, in some embodiments, the target region is found within the region from nucleotide 832 to the 3' most nucleotide of SEQ ID NO: 1. Typically oligomers do not target the polyA tail of the mRNA targets.

In some embodiments the oligomers of the invention have a nucleobase sequence which is 100% complementary to the corresponding region of the GLI2 mRNA, and comprise no more than 2, such as 1 or no mismatches with the corresponding region of the GLI1 mRNA target.

In such embodiments, in some aspects, the nucleobase sequence of the oligomer comprises 0, 1 or 2 mismatches when compared to the nucleobase sequence of the best aligned target region of the GLI3 mRNA, or in other aspects may comprise at least 2, such as 3, 4 or 5 mismatches when compared to the nucleobase sequence of the best aligned target region of the GLI3 mRNA.

Suitably, it is considered that oligomers have a base sequence with no more than 2 mismatches, such as no more than 1 mismatch, or no mismatches, when compared with the base sequences of the best aligned target regions of SEQ ID NO: 1 (human GLI2) and SEQ ID NO: 2 (human GLI1).

In some embodiments the oligomer of the invention has a contiguous nucleobase sequence which has 0, 1 or 2 mismatches when compared with the sequence of the reverse complement of the best aligned target region of SEQ ID NO 1, such as 1 or no mismatches, and at least 1 or at least 2 or at least 3 mismatches when compared with the sequence of the reverse complement of the best aligned target region of SEQ ID NO 2.

In some embodiments the oligomer of the invention has a contiguous nucleobase sequence which has 0, 1 or 2 mismatches when compared with the sequence of the reverse complement of the best aligned target region of SEQ ID NO 134, such as 1 or no mismatches, and at least 1 or at least 2 or at least 3 mismatches when compared with the sequence of the reverse complement of the best aligned target region of SEQ ID NO 2.

Oligomer Sequences

In some embodiments, the oligomers of the invention have sequences that are identical to an oligomer having a sequence selected from the group consisting of SEQ ID NOs: 3 to 90.

Further provided are target nucleic acids (e.g., DNA or mRNA encoding GLI2) that contain target regions that are (fully or perfectly) complementary or partially-complementary to one or more of the oligomers of the invention. In certain embodiments, the oligomers bind to variants of GLI2 target regions, such as allelic variants (such as mRNA derived from the GLI2 gene present on human Chromosome 2; location 2q14). In certain embodiments, the oligomers bind to variants of GLI1 target regions, such as allelic variants (such as mRNA derived from the GLI1 gene present on human Chromosome 12; location 12q13.2-q13.3). In certain embodiments, the oligomers bind to variants of GLI3 target regions, such as allelic variants (such as mRNA derived from the GLI3 gene present on human Chromosome 17; location 7p13). In some embodiments, a variant of a GLI2 and/or GLI1 and/or GLI3 target region has at least 60%, more preferably at least 70%, more preferably at least 80%, more preferably at least 85%, more preferably at least 90%, more preferably at least 91%, at least 92%, at least 93%, at least 94%, at least 95%, at least 96%, at least 97%, at least 98%, at least 99% sequence identity to the target region having a sequence set forth in SEQ ID NO: 1 and/or SEQ ID NO: 2 and/or SEQ ID NO: 134. Thus, in other embodiments, the oligomers of the invention have sequences that differ in 1, 2 or 3 bases when compared to an oligomer with a sequence selected from the group consisting of SEQ ID NOs: 3 to 90. Typically, an oligomer of the invention that binds to a variant of a GLI2 target region is capable of inhibiting (e.g., by down-regulating) GLI2. Typically, an oligomer of the invention that binds to a variant of a GLI1 target region is capable of inhibiting (e.g., by down-regulating) GLI1. Typically, an oligomer of the invention that binds to a variant of a GLI3 target region is capable of inhibiting (e.g., by down-regulating) GLI3.

In other embodiments, oligomers of the invention are LNA oligomers, for example, those oligomers having the sequences shown in SEQ ID NOs: 91 to 132. In various embodiments, the oligomers of the invention are potent inhibitors of GLI2 and/or GLI1 and/or GLI3 mRNA and protein expression. In some embodiments, the phrase "potent inhibitor" refers to an oligomer with an IC50 of less than 5 nM as determined by the lipofectamine transfection assay of Example 5. In some embodiments, the IC50 is less than 4 nM, such as less than 2 nM.

In various embodiments, oligomers of the invention are LNA oligomers having the sequences of SEQ ID NO: 118 or SEQ ID NO: 132.

In various embodiments, the oligomer comprises or consists of a first region having a base sequence which is identical or partially identical to the sequence of the reverse complement of a target region in SEQ ID NO: 1 and/or SEQ ID NO: 2 and/or SEQ ID NO: 134. In various embodiments, the oligomer comprises or consists of a first region having a sequence selected from the group consisting of SEQ ID NOs: 3 to 90.

In certain embodiments, the oligomer comprises or consists of a first region having a base sequence which is fully complementary (perfectly complementary) to the sequence of a target region of a nucleic acid which encodes a mammalian GLI2 and/or GLI1 and/or GLI3.

In some embodiments, the oligomer includes 1, 2, 3, or 4 (or more) mismatches as compared to the best-aligned target region of a GLI2 and/or GLI1 and/or GLI3 target nucleic acid, and still sufficiently binds to the target region to effect inhibition of GLI2 and/or GLI1 and/or GLI3 mRNA or protein expression. The destabilizing effect of mismatches on Watson-Crick hydrogen-bonded duplex may, for example, be compensated for by increased length of the oligomer and/or an increased number of nucleoside analogues, such as LNA monomers, present within the oligomer.

In various embodiments, the oligomer base sequence comprises no more than 3, such as no more than 2 mismatches compared to the base sequence of the best-aligned target region of, for example, a target nucleic acid which encodes mammalian GLI2 or GLI1 or GLI3.

In some embodiments, the oligomer base sequence comprises no more than a single mismatch when compared to the base sequence of the best-aligned target region of a nucleic acid which encodes a mammalian GLI2.

In various embodiments, the base sequence of the oligomer of the invention, or of a first region thereof, is preferably at least 80% identical to an oligomer having a base sequence selected from the group consisting of SEQ ID NOS: 3-90, such as at least 85%, at least 90%, at least 91%, at least 92%, at least 93%, at least 94%, at least 95%, at least 96%, at least 97%, at least 98%, at least 99% identical, such as 100% identical.

In certain embodiments, the base sequence of the oligomer of the invention or of a first region thereof is at least 80% identical to the base sequence of the reverse complement of a target region present in SEQ ID NO: 1 and/or SEQ ID NO: 2 and/or SEQ ID NO: 134, such as at least 85%, at least 90%, at least 91%, at least 92%, at least 93%, at least 94%, at least 95%, at least 96% identical, at least 97% identical, at least 98% identical, at least 99% identical, such as 100% identical.

In various embodiments, the base sequence of the oligomer of the invention, or of a first region thereof, is preferably at least 80% complementary to a target region of SEQ ID NO: 1 and/or SEQ ID NO: 2 and/or SEQ ID NO: 134, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments the oligomer (or a first region thereof) has a base sequence selected from the group consisting of SEQ ID NOs: 3, 10, 19, 35, 59 and 75, or is selected from the group consisting of at least 9 or 10 contiguous monomers of SEQ ID NOs: 3, 10, 19, 35, 59 and 75. In other embodiments, the sequence of the oligomer of the invention or a first region thereof comprises one, two, or three base moieties that differ (e.g. are mismatches) from those in oligomers having sequences of SEQ ID NOs: 3, 10, 19, 35, 59 and 75, or the sequences of at least 9 or 10 contiguous monomers thereof, when optimally aligned with the selected sequence or region thereof.

In some embodiments, the term "first region" as used herein refers to a portion (subsequence) of an oligomer. For example, the 16 monomer having the sequence set forth in SEQ ID NO: 19 is a subsequence of the 24 monomer having the sequence set forth in SEQ ID NO: 87, i.e., the oligomer having the sequence set forth in SEQ ID NO: 87 comprises the sequence set forth in SEQ ID NO: 19.

In some embodiments the oligomer (or a first region thereof) has a base sequence selected from the group consisting of SEQ ID NOs: 85 to 90, or the sequences of at least 9 or 10 contiguous monomers thereof. In other embodiments, the sequence of the oligomer (or a first region thereof) comprises one, two, or three base moieties that differ from those in oligomers having sequences of SEQ ID NOs: 85 to 90, or the sequences of at least 9 or 10 contiguous monomers thereof, when optimally aligned with the selected sequence or region thereof.

In various embodiments, the oligomers comprise a region of 9, 10, 11, 12, 13, 14, 15 or 16 contiguous monomers, such as 12-16, having a base sequence identically present in a sequence selected from the group consisting of SEQ ID Nos 3, 10, 19, 35, 59 and 75. In other embodiments, the oligomers include a region which comprises one, two, or three base moieties that differ from those in oligomers having sequences of SEQ ID NOs: 3, 10, 19, 35, 59 and 75.

In some embodiments the first region consists of 9, 10, 11, 12, 13, 14, 15, 16, 17, 18, 19, 20, 21, 22, 23, 24, 25, 26, 27, 28, or 29 contiguous monomers, such as 9-22, such as 12-24, such as 12-22, such as 12-18, such as 12-16 monomers. Suitably, in some embodiments, the first region is of the same length as the oligomer of the invention.

In some embodiments the oligomer comprises additional monomers at the 5' and/or 3' ends of the first region, such as, independently, 1, 2, 3, 4 or 5 additional monomers at the 5' end and/or the 3' end of the oligomer, which are non-complementary to the target region. In various embodiments, the oligomer of the invention comprises a first region that is complementary to the target, which is flanked 5' and/or 3' by additional monomers which are complementary to the target region. In some embodiments the additional 5' or 3' monomers are nucleosides, such as DNA or RNA monomers. In various embodiments, the 5' or 3' monomers represent region D as referred to in the context of gapmer oligomers herein.

In some embodiments the oligomer according to the invention consists of or comprises contiguous monomers (a first region) having a nucleobase sequence according to SEQ ID NO: 85, or at least 9 contiguous monomers thereof such as 10, 11, 12, 13, 14, 15 or 16 contiguous monomers thereof, such as SEQ ID NOs 3, 4, 5, 6, 7, or 8.

In some embodiments the oligomer according to the invention consists of or comprises contiguous monomers (a first region) having a nucleobase sequence according to SEQ ID NO: 86, or at least 9 contiguous monomers thereof such as 10, 11, 12, 13, 14, 15 or 16 contiguous monomers thereof, such as SEQ ID NOs 10, 11, 12, 13, 14 or 15.

In some embodiments the oligomer according to the invention consists of or comprises contiguous monomers (a first region) having a nucleobase sequence according to SEQ ID NO: 87, or at least 9 contiguous monomers thereof such as 10, 11, 12, 13, 14, 15 or 16 contiguous monomers thereof, such as SEQ ID NOs 19, 20, 21, 22, 23, 24, 25, 26, 27, 28, 29, 30, 31, 32 or 33.

In some embodiments the oligomer according to the invention consists of or comprises contiguous monomers (a first region) having a nucleobase sequence according to SEQ ID NO: 88, or at least 9 contiguous monomers thereof such as 10, 11, 12, 13, 14, 15 or 16 contiguous monomers thereof, such as SEQ ID NOs 36, 37, 38, 39, 40, 41, 42, 43, 44, 45, 46, 47, 48 or 49.

In some embodiments the oligomer according to the invention consists of or comprises contiguous monomers (a first region) having a nucleobase sequence-according to SEQ ID NO: 89, or at least 9 contiguous monomers thereof such as 10, 11, 12, 13, 14, 15 or 16 contiguous monomers thereof, such as SEQ ID NOs 60, 61, 62, 63, 64, 65, 66, 67, 68, 69, 70, 71, 72 or 73.

In some embodiments the oligomer according to the invention consists of or comprises contiguous monomers (a first region) having a nucleobase sequence according to SEQ ID NO: 90, or at least 9 contiguous monomers thereof such as 10, 11, 12, 13, 14, 15 or 16 contiguous monomers thereof, such as SEQ ID NOs 76, 77, 78, 79, 80, 81, 82, 83, or 84.

In some embodiments the oligomer according to the invention consists of or comprises contiguous monomers (a first region) having a nucleobase sequence according to SEQ ID NO: 9, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 16, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 17, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 18, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 34, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 35, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 50, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 51, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 52, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 53, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 54, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 55, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 56, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 57, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 58, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 59, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 74, or at least 9 contiguous monomers thereof such as 10, 11, 12, 13, 14, 15 or 16 contiguous monomers thereof.

In some embodiments the oligomer according to the invention consists of or comprises contiguous monomers (a first region) having a nucleobase sequence according to SEQ ID NO: 75, or at least 9 contiguous monomers thereof such as 10, 11, 12, 13, 14, 15 or 16 contiguous monomers thereof.

Nucleosides and Nucleoside Analogues

In some embodiments, the terms "nucleoside analogue" and "nucleotide analogue" are used interchangeably.

In various embodiments, at least one of the monomers present in the oligomer is a nucleoside analogue that contains a modified base, such as a base selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In various embodiments, at least one of the monomers present in the oligomer is a nucleoside analogue that comprises a modified sugar.

In some embodiments, the linkage between at least 2 contiguous monomers of the oligomer is other than a phosphodiester linkage.

In certain embodiments, the oligomer includes at least one monomer that has a modified base, at least one monomer (which may be the same monomer) that has a modified sugar, and at least one inter-monomer linkage that is non-naturally occurring.

Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1 (in which some nucleoside analogues are shown as nucleotides)

Scheme 1

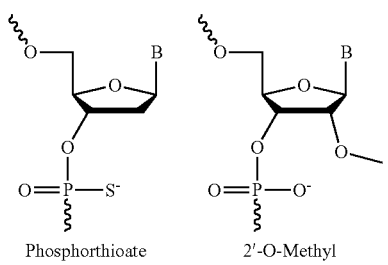

Phosphorthioate    2'-O-Methyl

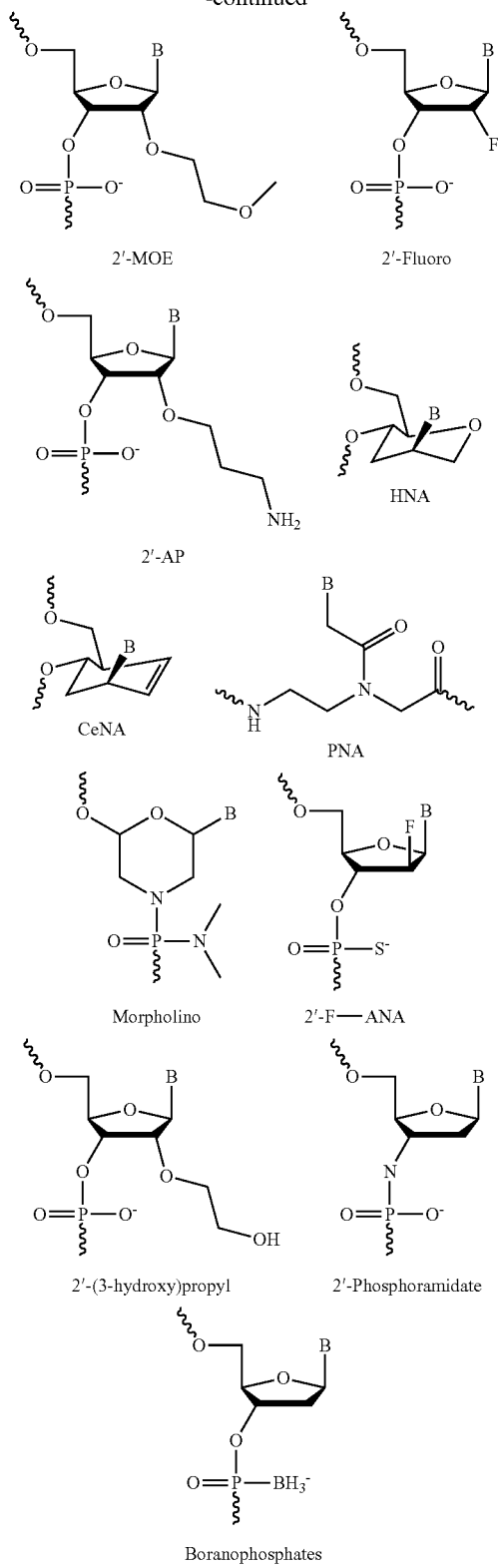

The oligomer may thus comprise or consist of a simple sequence of naturally occurring nucleosides—preferably DNA monomers, but also possibly RNA monomers, or a combination of nucleosides and one or more nucleoside analogues. In some embodiments, such nucleoside analogues suitably enhance the affinity of the oligomer for the target region of the target nucleic acid.

Examples of suitable and preferred nucleoside analogues are described in WO2007/031091, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a bicyclic sugar (LNA), which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In certain embodiments, the LNA monomers are beta-D-oxy-LNA. LNA monomers are further described below.

In various embodiments, incorporation of affinity-enhancing nucleoside analogues in the oligomer, such as LNA monomers or monomers containing 2'-substituted sugars, or incorporation of modified linkage groups provides increased nuclease resistance. In various embodiments, incorporation of affinity-enhancing nucleoside analogues allows the size of the oligomer to be reduced, and also reduces the size of the oligomer that binds specifically to a target region of a target sequence.

In some embodiments, the oligomer comprises at least 1 nucleoside analogue. In some embodiments, the oligomer comprises at least 2 nucleoside analogues. In some embodiments, the oligomer comprises from 3-8 nucleoside analogues, e.g. 6 or 7 nucleoside analogues. In various embodiments, at least one of the nucleoside analogues is a locked nucleic acid (LNA) monomer; for example at least 3 or at least 4, or at least 5, or at least 6, or at least 7, or 8, nucleoside analogues are LNA monomers. In some embodiments, all the nucleoside analogues are LNA monomers.

It will be recognised that when referring to a preferred oligomer base sequence, in certain embodiments, the oligomers comprise a corresponding nucleoside analogue, such as a corresponding LNA monomer or other corresponding nucleoside analogue, which raises the duplex stability ($T_m$) of the oligomer/target region duplex (i.e. affinity enhancing nucleoside analogues).

In various embodiments, any mismatches (i.e., non-complementarities) between the base sequence of the oligomer and the base sequence of the target region, if present, are preferably located other than in the regions of the oligomer that contain affinity-enhancing nucleoside analogues (e.g., regions A or C), such as within region B as referred to herein, and/or within region D as referred to herein, and/or in regions consisting of DNA monomers, and/or in regions which are 5' or 3' to the region of the oligomer that is complementary to the target region.

In some embodiments the nucleoside analogues present within the oligomer of the invention (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-arabinose sugars, monomers containing d-arabino-hexitol sugars ("HNA monomers"), intercalating monomers as defined in Christensen (2002) Nucl. Acids. Res. 30:4918-4925, hereby incorporated by reference, and 2'-O-methoxyethyl-ribose (2'MOE) sugars. In some embodiments, there is only one of the above types of nucleoside analogues present in the oligomer of the invention, or region thereof.

In certain embodiments, the nucleoside analogues contain 2'MOE sugars, 2'-fluoro-deoxyribose sugars, or LNA sugars, and as such the oligomer of the invention may comprise nucleoside analogues which are independently selected from these three types. In certain oligomer embodiments containing nucleoside analogues, at least one of said nucleoside analogues contains a 2'-MOE-ribose sugar, such as 2, 3, 4, 5, 6, 7, 8, 9 or 10 nucleoside analogues containing 2'-MOE-ribose sugars. In some embodiments, at least one nucleoside analogue contains a 2'-fluoro-deoxyribose sugar, such as 2, 3, 4, 5, 6, 7, 8, 9 or 10 nucleoside analogues containing 2'-fluoro-DNA nucleotide sugars.

In various embodiments, the oligomer according to the invention comprises at least one Locked Nucleic Acid (LNA) monomer, such as 1, 2, 3, 4, 5, 6, 7, or 8 LNA monomers, such as 3-7 or 4 to 8 LNA monomers, or 3, 4, 5, 6 or 7 LNA monomers. In various embodiments, all the nucleoside analogues are LNA monomers. In certain embodiments, the oligomer comprises both beta-D-oxy-LNA monomers, and one or more of the following LNA monomers: thio-LNA monomers, amino-LNA monomers, oxy-LNA monomers, and/or ENA monomers in either the beta-D or alpha-L configurations, or combinations thereof. In certain embodiments, the cytosine base moieties of all LNA monomers in the oligomer are 5-methylcytosines. In certain embodiments of the invention, the oligomer comprises both LNA and DNA monomers. Typically, the combined total of LNA and DNA monomers is 10-25, preferably 10-24, preferably 10-20, preferably 10-18, even more preferably 12-16. In some embodiments of the invention, the oligomer or region thereof consists of at least one LNA monomer, and the remaining monomers are DNA monomers. In certain embodiments, the oligomer comprises only LNA monomers and nucleosides (such as RNA or DNA monomers, most preferably DNA monomers) optionally with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" or "LNA monomer" refers to a bicyclic nucleoside analogue, known as "Locked Nucleic Acid". When used in the context of an "LNA oligonucleotide", LNA refers to an oligonucleotide containing one or more such bicyclic nucleoside analogues. LNA nucleosides are characterised by the presence of a linker group (such as a bridge) between C2' and C4' of the ribose sugar ring to form a bicyclic system—for example between the $R^{4*}$ and $R^{2*}$ groups as described below.

The LNA used in the oligonucleotide compounds (oligomers) of the invention preferably has the structure of the general formula I

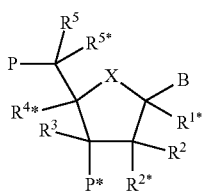

Formula 1 wherein for all chiral centers, asymmetric groups may be found in either R or S orientation;

wherein X is selected from —O—, —S—, —N(R$^{N}$*)— and —C(R$^6$R$^{6}$*)—, more preferably —O—;

B is selected from hydrogen, optionally substituted C$_{1-4}$-alkoxy, optionally substituted C$_{1-4}$-alkyl, optionally substituted C$_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleoside linkage to an adjacent monomer, or a 5'-terminal group, said internucleoside linkage or 5'-terminal group optionally including the substituent R$^5$ or equally applicable the substituent R$^{5}$*;

P* designates an internucleoside linkage to an adjacent monomer, or a 3'-terminal group;

R$^{4}$* and R$^{2}$* together form a bivalent linker group, such as, for example, a biradical consisting of 1-4 groups/atoms each independently selected from —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z, wherein Z is selected from —O—, —S—, and —N(R$^a$)—, and R$^a$ and R$^b$ are each independently selected from hydrogen, optionally substituted C$_{1-12}$-alkyl, optionally substituted C$_{2-12}$-alkenyl, optionally substituted C$_{2-12}$-alkynyl, hydroxy, optionally substituted C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where each aryl and heteroaryl may be optionally substituted and where two geminal substituents R$^a$ and R$^b$ together may form an optionally substituted methylene (=CH$_2$), wherein for all chiral centers, asymmetric groups may be found in either R or S orientation, and;

each of the substituents R$^{1}$*, R$^2$, R$^3$, R$^5$, R$^{5}$*, R$^6$ and R$^{6}$* is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where each aryl and heteroaryl may be optionally substituted, and where two geminal substituents together may designate oxo, thioxo, imino, or optionally substituted methylene; wherein R$^N$ is selected from hydrogen and C$_{1-4}$-alkyl, and where two adjacent (non-geminal) substituents may designate an additional bond resulting in a double bond; and basic salts and acid addition salts thereof. For all chiral centers, asymmetric groups may be found in either R or S orientation.

Where the definitions used herein refer to substituted C$_{1-4}$-alkyl, substituted C$_{1-6}$ alkyl, substituted C$_{1-12}$-alkyl, substituted C$_{2-12}$-alkenyl, substituted C$_{2-6}$ alkenyl, substituted C$_{2-12}$-alkynyl, substituted C$_{2-6}$ alkynyl, substituted C$_{1-12}$-alkoxy, substituted C$_{1-6}$ alkoxy, substituted C$_{1-4}$-alkoxy, substituted C$_{1-4}$-acyloxy, substituted aryl, substituted heteroaryl, substituted methylene, substituted acyl, substituted C$_{1-6}$ aminoalkyl or substituted amide, suitable substituents preferably include one or more R$^g$ groups, wherein each R$^g$ is independently selected from halogen, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, CN, OJ$_1$, SJ$_1$, NJ$_1$J$_2$, N$_3$, COOJ$_1$, C(=X)J$_1$, C(=X)NJ$_1$J$_2$, CN, O—C(=O)NJ$_1$J$_2$, O—C(=X)J$_1$, NJ$_1$C(=NH)NJ$_1$J$_2$ and NJ$_1$C(=X)NJ$_1$J$_2$ wherein X is O or S; and each J$_1$ and J$_2$ is independently selected from H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{1-6}$ aminoalkyl, substituted C$_{1-6}$ aminoalkyl and a protecting group. Preferably, each R$^g$ is independently selected from halogen, C$_{1-6}$ alkyl, C$_{2-6}$ alkenyl, C$_{2-6}$ alkynyl, CN, OJ$_1$, SJ$_1$, NJ$_1$J$_2$, N$_3$, COOJ$_1$, C(=X)J$_1$, C(=X)NJ$_1$J$_2$, CN, O—C(=O)NJ$_1$J$_2$, O—C(=X)J$_1$, NJ$_1$C(=NH)NJ$_1$J$_2$ and NJ$_1$C(=X)NJ$_1$J$_2$ wherein X is O or S; and each J$_1$ and J$_2$ is independently selected from H, C$_{1-6}$ alkyl, C$_{2-6}$ alkenyl, C$_{2-6}$ alkynyl, C$_{1-6}$ aminoalkyl and a protecting group. Suitable protecting groups are described in "Protective Groups in Organic Synthesis" by Theodora W Greene and Peter G M Wuts, 3rd edition (John Wiley & Sons, 1999).

In some embodiments, R$^{4}$* and R$^{2}$* together form a linker group selected from C(R$^a$R$^b$)—C(R$^a$R$^b$)—, C(R$^a$R$^b$)—O—, C(R$^a$R$^b$)—NR$^a$—, C(R$^a$R$^b$)—S—, and C(R$^a$R$^b$)—C(R$^a$R$^b$)—O—, wherein R$^a$ and R$^b$ are as defined above. In some embodiments, R$^a$ and R$^b$ are each independently selected from hydrogen and C$_{1-6}$ alkyl, and are more preferably each independently selected from hydrogen and methyl.

In some embodiments, R$^{1}$*, R$^2$, R$^3$, R$^5$, R$^{5}$* are each independently selected from hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{1-6}$ alkoxy, substituted C$_{1-6}$ alkoxy, acyl, substituted acyl, C$_{1-6}$ aminoalkyl and substituted C$_{1-6}$ aminoalkyl. For all chiral centers, asymmetric groups may be found in either R or S orientation.

In some preferred embodiments, R$^{1}$*, R$^2$, R$^3$, R$^5$, R$^{5}$* are all hydrogen.

In some embodiments, R$^{1}$*, R$^2$, R$^3$ are each independently selected from hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{1-6}$ alkoxy, substituted C$_{1-6}$ alkoxy, acyl, substituted acyl, C$_{1-6}$ aminoalkyl and substituted C$_{1-6}$ aminoalkyl. For all chiral centers, asymmetric groups may be found in either R or S orientation.

In some preferred embodiments, R$^{1}$*, R$^2$, R$^3$ are all hydrogen.

In some embodiments, R$^5$ and R$^{5}$* are each independently selected from H, —CH$_3$, —CH$_2$—CH$_3$, —CH$_2$—O—CH$_3$, and —CH=CH$_2$. Preferably, in some embodiments, either $R^5$ or $R^{5*}$ is hydrogen, and the other group ($R^5$ or $R^{5*}$ respectively) is selected from $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl and substituted acyl (—C(=)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(=O)$NJ_1J_2$, N(H)C(=NH)$NJ_1J_2$ and N(H)C(=X)N(H)$J_2$ wherein X is O or S; and each $J_1$ and $J_2$ is independently selected from H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl and a protecting group. In some embodiments either $R^5$ or $R^{5*}$ is substituted $C_{1-6}$ alkyl. In some embodiments either $R^5$ or $R^{5*}$ is substituted methylene, wherein preferred substituent groups include one or more groups independently selected from F, $NJ_1J_2$, $N_3$, CN, $OJ_1$, $SJ_1$, O—C(=O)$NJ_1J_2$, N(H)C(=NH)$NJ_1J_2$ and N(H)C(O)N(H)$J_2$. In some embodiments each $J_1$ and $J_2$ is independently H or $C_{1-6}$ alkyl. In some embodiments either $R^5$ or $R^{5*}$ is methyl, ethyl or methoxymethyl. In some embodiments either $R^5$ or $R^{5*}$ is methyl. In some embodiments either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Examples of such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, or a nucleobase selected from adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine and 2,6-diaminopurine.

In some embodiments, $R^{4*}$ and $R^{2*}$ together form a linker group selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, —C($R^aR^b$)—S— and —C($R^aR^b$)—C($R^cR^d$)—S—, wherein $R^a$, $R^b$, $R^c$, $R^d$, $R^e$, and $R^f$ are each independently selected from hydrogen, optionally substituted $C_{1-2}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where each aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In some embodiments $R^{4*}$ and $R^{2*}$ together designate a linker group selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, —CH($CH_2$—O—$CH_3$)—O—, —$CH_2$—$CH_2$— and —CH=CH— For all chiral centers, asymmetric groups may be found in either R or S orientation.

In some embodiments, $R^{4*}$ and $R^{2*}$ together form a linker group C($R^aR^b$)—N($R^c$)—O—, wherein $R^a$ and $R^b$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl, more preferably $R^a$ and $R^b$ are hydrogen, and; wherein $R^c$ is selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl, substituted $C_{1-6}$ aminoalkyl, and more preferably $R^c$ is hydrogen.

In some embodiments, $R^{4*}$ and $R^{2*}$ together form a linker group C($R^aR^b$)—O—C($R^cR^d$)—O—, wherein $R^a$, $R^b$, $R^c$, and $R^d$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl, substituted $C_{1-6}$ aminoalkyl, and more preferably $R^a$, $R^b$, $R^c$, and $R^d$ are hydrogen.

In some embodiments, $R^{4*}$ and $R^{2*}$ form a linker group —CH(Z)—O—, wherein Z is selected from $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol and substituted thiol; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Examples of such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are all hydrogen. In some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together form a linker group which comprises a substituted amino group, for example, $R^{4*}$ and $R^{2*}$ together form a linker group that consists of, or comprises, the group —$CH_2$—N($R^c$)—, wherein $R^c$ is $C_{1-12}$ alkyloxy. In some embodiments $R^{4*}$ and $R^{2*}$ together form a linker group —$Cq_3q_4$-NOR—, wherein $q_3$ and $q_4$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)$NJ_1J_2$ and N(H)C(=X=N(H)$J_2$ wherein X is O or S; and each of $J_1$ and $J_2$ is independently selected from H, $C_{1-6}$ alkyl, $C_{2-6}$ alkenyl, $C_{2-6}$ alkynyl, $C_{1-6}$ aminoalkyl and a protecting group. For all chiral centers, asymmetric groups may be found in either R or S orientation. Examples of such bicyclic nucleotides are disclosed in WO2008/150729 which is hereby incorporated by reference in its entirety. In some embodiments, $R^{1*}$, $R^2$, $R^3$, $R^5$, $R^{5*}$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl. In some embodiments, $R^{1*}$, $R^2$, $R^3$, $R^5$, $R^{5*}$ are all hydrogen. In some embodiments, $R^{1*}$, $R^2$, $R^3$ are all hydrogen and one or both of $R^5$, $R^{5*}$ may be other than hydrogen as referred to above and in WO 2007/134181. In some embodiments $R^{4*}$ and $R^{2*}$ together form a linker group $C(R^aR^b)$—O—, wherein $R^a$ and $R^b$ are each independently selected from halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ and N(H)C(=S)$NJ_1J_2$; or $R^a$ and $R^b$ together are =C($q_3$)($q_4$); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; each $J_1$ and $J_2$ is independently selected from H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl and a protecting group. Such compounds are disclosed in WO2009/006478, hereby incorporated in its entirety by reference.

In some embodiments, $R^{4*}$ and $R^{2*}$ form a linker group -Q-, wherein Q is C($q_1$)($q_2$)C($q_3$)($q_4$), C($q_1$)=C($q_3$), C[=C($q_1$)($q_2$)]—C($q_3$)($q_4$) or C($q_1$)($q_2$)—C[=C($q_3$)($q_4$)]; $q_1$, $q_2$, $q_3$, $q_4$ are each independently selected from H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O)$J_1$, —C(=O)$NJ_1J_2$, N(H)C(=NH)$NJ_1J_2$, N(H)C(=O)$NJ_1J_2$ and N(H)C(=S)$NJ_1J_2$; each $J_1$ and $J_2$ is independently selected from H, $C_{1-6}$ alkyl, $C_{2-6}$ alkenyl, $C_{2-6}$ alkynyl, $C_{1-6}$ aminoalkyl and a protecting group; and, optionally wherein when Q is C($q_1$)($q_2$)($q_3$)($q_4$) and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are all hydrogen. For all chiral centers, asymmetric groups may be found in either R or S orientation. Examples of such bicyclic nucleotides are disclosed in WO2008/154401 which is hereby incorporated by reference in its entirety. In some embodiments, $R^{1*}$, $R^2$, $R^3$, $R^5$, $R^{5*}$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl. In some embodiments, $R^{1*}$, $R^2$, $R^3$, $R^5$, $R^{5*}$ are all hydrogen. In some embodiments, $R^{1*}$, $R^2$, $R^3$ are all hydrogen and one or both of $R^5$, $R^{5*}$ may be other than hydrogen as referred to above and in WO 2007/134181 or WO2009/067647 (alpha-L-bicyclic nucleic acids analogs).

In some preferred embodiments the LNA monomer present in the oligonucleotide compounds of the invention preferably has the structure of the general formula II:

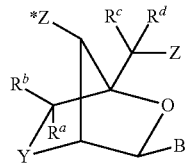

Formula II wherein Y is selected from —O—, —$CH_2$O—, —S—, —NH—, N($R^e$) and —$CH_2$—; Z and Z* are each independently selected from an internucleoside linkage, $R^H$, a terminal group and a protecting group; B constitutes a natural or non-natural nucleotide base moiety (nucleobase), and $R^H$ is selected from hydrogen and $C_{1-4}$-alkyl; $R^a$, $R^b$, $R^c$, $R^d$ and $R^e$ are each independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where each aryl and heteroaryl may be optionally substituted and where two geminal substituents $R^a$ and $R^b$ together may designate optionally substituted methylene (=$CH_2$); and $R^H$ is selected from hydrogen and $C_{1-4}$-alkyl. In some preferred embodiments $R^a$, $R^b$, $R^c$, $R^d$ and $R^e$ are each independently selected from hydrogen and $C_{1-6}$ alkyl, more preferably methyl. For all chiral centers, asymmetric groups may be found in either R or S orientation, for example, two exemplary stereochemical isomers include the beta-D and alpha-L isoforms, which may be illustrated as follows:

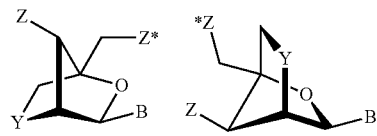

Specific exemplary LNA units are shown below (in Scheme 2):

Scheme 2

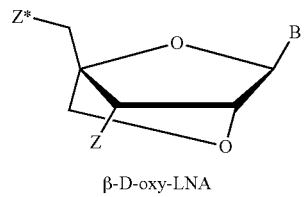

β-D-oxy-LNA

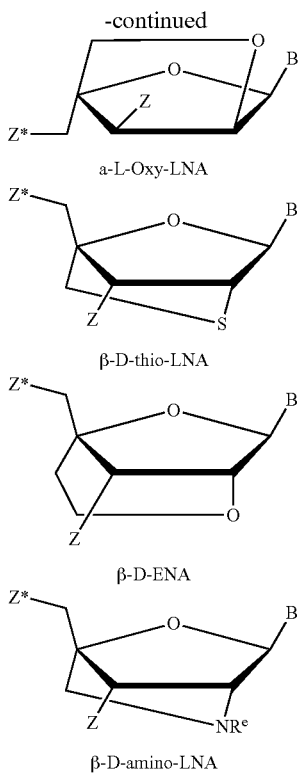

The term "thio-LNA" comprises a locked nucleoside in which Y in the general formula above is selected from S or —CH$_2$—S—. Thio-LNA can be in both beta-D and alpha-L-configuration.

The term "amino-LNA" comprises a locked nucleoside in which Y in the general formula above is selected from —N(H)—, N(R)—, CH$_2$—N(H)—, and —CH$_2$—N(R)— where R is selected from hydrogen and $C_{1-4}$-alkyl. Amino-LNA can be in both beta-D and alpha-L-configuration.

The term "oxy-LNA" comprises a locked nucleoside in which Y in the general formula above represents —O—. Oxy-LNA can be in both beta-D and alpha-L-configuration. The term "ENA" comprises a locked nucleoside in which Y in the general formula above is —CH$_2$—O— (where the oxygen atom of —CH$_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

RNAse H Recruitment

In some embodiments, an oligomer functions via non-RNase-mediated degradation of a target mRNA, such as by steric hindrance of translation, or other mechanisms; however, in various embodiments, oligomers of the invention are capable of recruiting one or more RNAse enzymes or complexes, such as endo-ribonuclease (RNase), such as RNase H.

Typically, the oligomer, comprises a region of at least 6, such as at least 7 contiguous monomers; such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein. In some embodiments, the region of the oligomer which is capable of recruiting RNAse, such as region B, consists of 9, 10, 11, 12, 13, 14, 15, 16, 17, 18, 19 or 20 monomers.

EP 1 222 309 provides in vitro methods for determining RNaseH activity, which may be used to determine the ability of the oligomers of the invention to recruit RNaseH. An oligomer is deemed capable of recruiting RNaseH if, when contacted with the complementary region of the RNA target, it has an initial rate, as measured in pmol/l/min, of at least 1%, such as at least 5%, such as at least 10% or more than 20% of the initial rate determined using an oligonucleotide having the same base sequence but containing only DNA monomers, with no 2' substitutions, with phosphorothioate linkage groups between all monomers in the oligonucleotide, using the methodology provided by Examples 91-95 of EP 1 222 309, incorporated herein by reference.

In some embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

Typically, the region of the oligomer which forms the duplex with the complementary target region of the target RNA and is capable of recruiting RNase contains DNA monomers and optionally LNA monomers and forms a DNA/RNA-like duplex with the target region. The LNA monomers are preferably in the alpha-L configuration, particularly preferred being alpha-L-oxy LNA.

In various embodiments, the oligomer of the invention comprises both nucleosides and nucleoside analogues, and is in the form of a gapmer, a headmer or a mixmer.

A "headmer" is defined as an oligomer that comprises a region X and a region Y that is contiguous thereto, with the 5'-most monomer of region Y linked to the 3'-most monomer of region X. Region X comprises a contiguous stretch of non-RNase recruiting nucleoside analogues and region Y comprises a contiguous stretch (such as at least 7 contiguous monomers) of DNA monomers or nucleoside analogue monomers recognizable and cleavable by the RNase.

A "tailmer" is defined as an oligomer that comprises a region X and a region Y that is contiguous thereto, with the 5'-most monomer of region Y linked to the 3'-most monomer of the region X. Region X comprises a contiguous stretch (such as at least 7 contiguous monomers) of DNA monomers or nucleoside analogue monomers recognizable and cleavable by the RNase, and region Y comprises a contiguous stretch of non-RNase recruiting nucleoside analogues.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNaseH) binding and cleavage. Since a-L-LNA monomers recruit RNaseH activity to a certain extent, in some embodiments, gap regions (e.g., region B as referred to herein) of oligomers containing a-L-LNA monomers consist of fewer monomers recognizable and cleavable by the RNaseH, and more flexibility in the mixmer construction is introduced.

Conjugates

In the context of this disclosure, the term "conjugate" indicates a compound formed by the covalent attachment ("conjugation") of an oligomer as described herein, to one or more moieties that are not themselves nucleic acids or monomers ("conjugated moieties"). Examples of such conjugated moieties include macromolecular compounds such as proteins, fatty acid chains, sugar residues, glycoproteins, polymers, or combinations thereof. Typically proteins may be antibodies for a target protein. Typical polymers may be polyethylene glycol.

Accordingly, provided herein are conjugates comprising an oligomer as herein described, and at least one conjugated moiety that is not a nucleic acid or monomer, covalently attached to said oligomer. Therefore, in certain embodiments where the oligomer of the invention consists of contiguous monomers having a specified sequence of bases, as herein disclosed, the conjugate may also comprise at least one conjugated moiety that is covalently attached to the oligomer.

In various embodiments of the invention, the oligomer is conjugated to a moiety that increases the cellular uptake of oligomeric compounds. WO2007/031091 provides suitable ligands and conjugates (moieties), which are hereby incorporated by reference.

In various embodiments, conjugation (to a conjugated moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipid, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

In certain embodiments, the oligomers of the invention are conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptide of, for example 1-50, such as 2-20 such as 3-10 amino acid residues in length, and/or polyalkylene oxide such as polyethylene glycol (PEG) or polypropylene glycol—see WO 2008/034123, hereby incorporated by reference. Suitably the positively charged polymer, such as a polyalkylene oxide may be attached to the oligomer of the invention via a linker such as the releasable linker described in WO 2008/034123.

By way of example, the following moieties may be used in the conjugates of the invention:

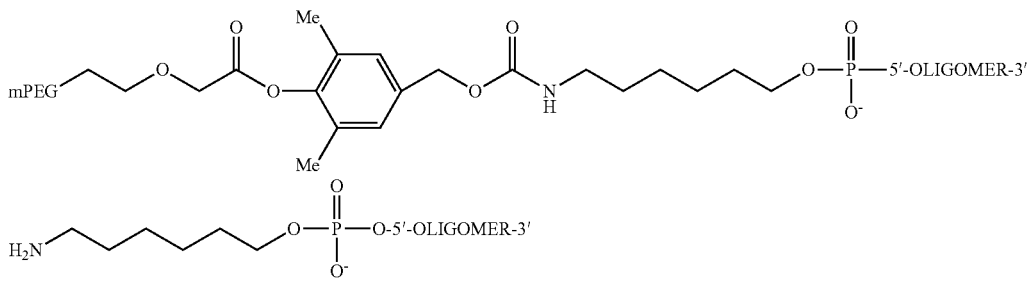

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W. Greene and Peter G. M. Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are activated (i.e. functionalized) at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH). In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular, by methods disclosed in PCT Publication No. WO 2008/034122 and the examples therein, which is incorporated herein by reference in its entirety.

Activated oligomers covalently linked to at least one functional moiety can be synthesized by any method known in the art, and in particular, by methods disclosed in U.S. Patent Publication No. 2004/0235773, which is incorporated herein by reference in its entirety, and in Zhao et al. (2007) J. Controlled Release 119:143-152; and Zhao et al. (2005) Bioconjugate Chem. 16:758-766.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

In various embodiments, the oligomer of the invention is used in pharmaceutical formulations and compositions. Suitably, such compositions comprise a pharmaceutically acceptable diluent, carrier, salt or adjuvant. WO2007/031091 provides suitable and preferred pharmaceutically acceptable diluents, carriers and adjuvants—which are hereby incorporated by reference. Suitable dosages, formulations, administration routes, compositions, dosage forms, combinations with other therapeutic agents, pro-drug formulations are also provided in WO2007/031091—which are also hereby incorporated by reference. Details on techniques for formulation and administration also may be found in the latest edition of "REMINGTON'S PHARMACEUTICAL SCIENCES" (Maack Publishing Co, Easton Pa.).

In some embodiments, an oligomer of the invention is covalently linked to a conjugated moiety to aid in delivery of the oligomer across cell membranes. An example of a conjugated moiety that aids in delivery of the oligomer across cell membranes is a lipophilic moiety, such as cholesterol. In various embodiments, an oligomer of the invention is formulated with lipid formulations that form liposomes, such as Lipofectamine 2000 or Lipofectamine RNAiMAX, both of which are commercially available from Invitrogen. In some embodiments, the oligomers of the invention are formulated with a mixture of one or more lipid-like non-naturally occurring small molecules ("lipidoids"). Libraries of lipidoids can be synthesized by conventional synthetic chemistry methods and various amounts and combinations of lipidoids can be assayed in order to develop a vehicle for effective delivery of an oligomer of a particular size to the targeted tissue by the chosen route of administration. Suitable lipidoid libraries and compositions can be found, for example in Akinc et al. (2008) Nature Biotechnol., available at http://www.nature.com/nbt/journal/vaop/ncurrent/abs/nbt1402.html, which is incorporated by reference herein.

As used herein, the term "pharmaceutically acceptable salts" refers to salts that retain the desired biological activity of the herein identified oligomers and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylene-diamine, D-glucosamine, tetraethylammonium, or ethylenediamine; or (c) combinations of (a) and (b); e.g., a zinc tannate salt or the like.

In certain embodiments, the pharmaceutical compositions according to the invention comprise other active ingredients in addition to an oligomer or conjugate of the invention, including active agents useful for the treatment of hyperproliferative disorders, such as cancer, such as prostate cancer, glioma, colorectal cancer, melanoma, breast cancer, lung cancer or hepatocellular carcinoma.

In some embodiments, the additional active agent is paclitaxel (Narita et al., Clin. Cancer. Res. 2008 Sep. 15: 14(18): 5769.

In one embodiment, the invention provides for a combined therapy, characterised in that the therapy comprises administering the pharmaceutical composition according to the invention, and an additional active agent (e.g. paclitaxel), which in certain embodiments are administered prior to, during or subsequent to the administration of the pharmaceutical compositions of the invention.

The invention also provides a kit of parts wherein a first part comprises at least one oligomer, conjugate and/or the pharmaceutical composition according to the invention and a further part comprises one or more active agents (e.g. paclitaxel) useful for the treatment of hyperproliferative disorders, such as cancer, such as prostate cancer, glioma, colorectal cancer, melanoma, breast cancer, lung cancer or hepatocellular carcinoma. It is therefore envisaged that the kit of parts may be used in a method of treatment, as referred to herein, where the method comprises administering both the first part and the further part, either simultaneously or one after the other.

Applications

The term "treatment" as used herein refers to both treatment of an existing disease (e.g., a disease or disorder as referred to herein below), or prevention of a disease, i.e., prophylaxis. It will therefore be recognised that, in certain embodiments, "treatment" includes prophylaxis.

In various embodiments, the oligomers of the invention may be utilized as research reagents for, for example, diagnostics, therapeutics and prophylaxis.

In some embodiments, such oligomers may be used for research purposes to specifically inhibit the expression of GLI2 and/or GLI1 and/or GLI3 protein (typically by degrading or inhibiting the GLI2 and/or GLI1 and/or GLI3 mRNA and thereby preventing protein formation) in cells and experimental animals, thereby facilitating functional analysis of the target or an appraisal of its usefulness as a target for therapeutic intervention.

In certain embodiments, the oligomers may be used in diagnostics to detect and/or to quantify GLI2 and/or GLI1 and/or GLI3 expression in cells and tissues by Northern blotting, in-situ hybridisation or similar techniques.

In various therapeutic embodiments, a non-human animal or a human suspected of having a disease or disorder which can be treated by modulating the expression of GLI2 and/or GLI1 and/or GLI3 is treated by administering an effective amount of an oligomer in accordance with this invention.

Further provided are methods of treating a mammal, such as treating a human, suspected of having or being prone to a disease or condition, associated with expression of GLI2 and/or GLI1 and/or GLI3 by administering a therapeutically or prophylactically effective amount of one or more of the oligomers, conjugates or compositions of the invention.

In certain embodiments, the invention also provides for the use of the oligomers or conjugates of the invention as described for the manufacture of a medicament for the treatment of a disorder as referred to herein, or for a method of the treatment of a disorder as referred to herein.

In various embodiments, the invention also provides for a method for treating a disorder as referred to herein, said method comprising administering an oligomer according to the invention as herein described, and/or a conjugate according to the invention, and/or a pharmaceutical composition according to the invention to an animal in need thereof (such as a patient in need thereof).

As illustrated in the examples, the oligomer of the invention may be used to induce apoptosis in a cell, such as a mammalian cell, such as a human cell, which is expressing the target nucleic acid(s)—in this regard the invention further provides a method for inducing apoptosis in a cell said method comprising the step of contacting the cell, which is expressing GLI2 and/or GLI1 and/or GLI3, with an oligomer or conjugate or pharmaceutical composition of the invention in an amount sufficient to induce apoptosis. Apoptosis may be triggered in vivo or in vitro. Suitably the oligomer is added in an amount effective to trigger apoptosis in said cell. In some embodiments the cell is a cancer cell.

Medical Indications

In certain therapeutic embodiments, the disorder to be treated is a hyperproliferative disorders (e.g., cancer), such as prostate cancer, glioma, colorectal cancer, breast cancer, lung cancer, melanoma, hepatocellular carcinoma, acute myeloid leukemia or preleukemia (myelodysplastic syndrome or myeloproliferative disease). In various embodiments, the treatment of such a disease or condition according to the invention may be combined with one or more other anti-cancer treatments, such as radiotherapy, chemotherapy or immunotherapy.

In various embodiments, the disease or disorder is associated with a mutation of the GLI2 and/or GLI1 and/or GLI3 gene or a gene whose protein product is associated with or interacts with GLI2 and/or GLI1 and/or GLI3. Therefore, in various embodiments, the target mRNA is a mutated form of the GLI2 and/or GLI1 and/or GLI3 sequence, for example, it comprises one or more single point mutations or triplet repeats.

In various embodiments, the disease or disorder is associated with abnormal levels of GLI2 and/or GLI1 and/or GLI3.

The term "abnormal" as used herein refers to over-expression (e.g. up-regulation) of the GLI2 and/or GLI1 and/or GLI3 gene in a cell compared to the expression level in a cell of an animal which does not have a disease, disorder or condition mentioned herein.

In some embodiments, an oligomer, a conjugate or a composition according to the invention can be used for the treatment of conditions associated with over-expression (e.g. up-regulation) of the GLI2 and/or GLI1 and/or GLI3 gene.

In other embodiments, the disease or disorder is associated with abnormal levels of a mutated form of GLI2 and/or GLI1 and/or GLI3.

The terms "mutation" and "mutated form" as used herein refer to a variant of GLI2 nucleic acid shown in SEQ ID NO: 1; and/or to a variant of GLI1 nucleic acid shown in SEQ ID NO: 2; and/or to a variant of GLI3 nucleic acid shown in SEQ ID NO: 134. Said variant may be associated with a disease, disorder or condition as referred to herein. In some embodiments, the term "variant" as used herein refers to a nucleotide sequence having a base sequence which differs from SEQ ID NO: 1 and/or SEQ ID NO: 2 and/or SEQ ID NO: 134 by one or more nucleotide additions and/or substitutions and/or deletions. In some embodiments the variant has at least 80%, 85%, 90% or 95% sequence homology (identity) with SEQ ID NO: 1 and/or SEQ ID NO: 2 and/or SEQ ID NO: 134. In the same or different embodiment, the variant has no more that 60 additional nucleotides and/or substituted nucleotides and/or deleted nucleotides over the whole of SEQ ID NO: 1 and/or SEQ ID NO: 2 and/or SEQ ID NO: 134; such as no more than 30 additional nucleotides and/or substituted nucleotides and/or deleted nucleotides; such as no more that 15 additional nucleotides and/or substituted nucleotides and/or deleted nucleotides over the whole of SEQ ID NO: 1 and/or SEQ ID NO: 2 and/or SEQ ID NO: 134.

In various embodiments, the invention relates to methods of modulating the expression of the gene product of a GLI2 target gene, i.e., a gene that is regulated by GLI2. Examples of GLI2 target genes include GLI1 and PTCH1. In some embodiments, modulation of a GLI2 target gene results in increased expression or activity of the target gene. In other embodiments, modulation of a GLI2 target gene results in decreased expression or activity of the target gene.

The invention further provides use of an oligomer of the invention in the manufacture of a medicament for the treatment of any and all conditions disclosed herein.

In various embodiments, the invention is directed to a method of treating a mammal suffering from or susceptible to a condition associated with abnormal levels of GLI2 and/or GLI1 and/or GLI3 mRNA or protein, comprising administering to the mammal a therapeutically effective amount of an oligomer of the invention, or a conjugate thereof, that comprises one or more LNA monomers.

An interesting aspect of the invention is directed to the use of an oligomer (compound) as defined herein or a conjugate as defined herein for the preparation of a medicament for the treatment of a condition as disclosed herein above.

In various embodiments, the invention encompasses a method of preventing or treating a disease comprising administering a therapeutically effective amount of an oligomer according to the invention, or a conjugate thereof, to a non-human animal or a human in need of such therapy.

In certain embodiments, the LNA oligomers of the invention, or conjugates thereof, are administered for a short period time rather than continuously.

In certain embodiments of the invention, the oligomer (compound) is linked to a conjugated moiety, for example, in order to increase the cellular uptake of the oligomer. In one embodiment the conjugated moiety is a sterol, such as cholesterol.

In various embodiments, the invention is directed to a method for treating abnormal levels of GLI2 and/or GLI1 and/or GLI3, the method comprising administering an oligomer of the invention, or a conjugate or a pharmaceutical composition thereof, to an animal (such as a patient) in need of such treatment, and optionally further comprising the administration of a further chemotherapeutic agent. In some embodiments, the chemotherapeutic agent is conjugated to the oligomer, is present in the pharmaceutical composition, or is administered in a separate formulation.

The invention also relates to an oligomer, a composition or a conjugate as defined herein for use as a medicament.

The invention further relates to use of an oligomer, composition, or a conjugate as defined herein for the manufacture of a medicament for the treatment of abnormal levels of GLI2 and/or GLI1 and/or GLI3 or expression of mutant forms of GLI2 and/or GLI1 and/or GLI3 (such as allelic variants, such as those associated with one of the diseases referred to herein).

Moreover, in various embodiments, the invention relates to a method of treating an animal (such as a patient) suffering from a disease or condition selected from the group consisting of hyperproliferative disorders, such as cancer, such as prostate cancer, glioma, colorectal cancer, melanoma, breast cancer, lung cancer or hepatocellular carcinoma, the method comprising the step of administering a pharmaceutical composition as defined herein to the animal (such as a patient) in need thereof.

In certain embodiments, the methods of the invention are employed for treatment or prophylaxis against diseases caused by abnormal levels of GLI2 and/or GLI1 and/or GLI3.

In some embodiments, the invention is directed to a method for treating abnormal levels of GLI2 and/or GLI1 and/or GLI3, said method comprising administering a oligomer of the invention, or a conjugate of the invention or a pharmaceutical composition of the invention to an animal (such as a patient) in need thereof.

Moreover, the invention relates to a method of treating an animal (such as a human) suffering from a disease or condition such as those referred to herein.

An animal (such as a patient) who is in need of treatment is an animal (such as a patient) suffering from or likely to suffer from the disease or disorder.

Suitable animals include human and non-human animals.

In some embodiments, the animal is a mammal. Examples include humans, rodents (such as rats and mice), rabbits, primates, non-human primates (such as chimpanzees and monkeys), horses, cattle, sheep, pigs, dogs and cats.

Suitable dosages, formulations, administration routes, compositions, dosage forms, combinations with other therapeutic agents, pro-drug formulations are also provided in WO2007/031091—which is hereby incorporated by reference.

The invention also provides for a pharmaceutical composition comprising an oligomer or a conjugate as herein described, and a pharmaceutically acceptable diluent, carrier or adjuvant. WO2007/031091 provides suitable and preferred pharmaceutically acceptable diluents, carriers and adjuvants—which are hereby incorporated by reference.

Embodiments

The following embodiments of the invention may be used alone or in combination with the other embodiments described herein.

1. An oligomer of between 10-30 nucleotides in length which comprises a contiguous nucleotide sequence of a total of between 10-30 nucleotides, wherein said contiguous nucleotide sequence is at least 80% homologous to a region corresponding to a mammalian GLI2 gene or the reverse complement of an mRNA, such as SEQ ID NO: 1 or a naturally occurring variant thereof.
2. The oligomer according to embodiment 1, wherein the contiguous nucleotide sequence is at least 80% homologous to a region corresponding to any of SEQ ID NO: 3-90.
3. The oligomer according to embodiment 1 or 2, wherein the contiguous nucleotide sequence comprises no mismatches or no more than, one or two mismatches with the reverse complement of the corresponding region of SEQ ID NO 1.
4. An oligomer according to any one of embodiments 1-3, wherein said contiguous nucleotide sequence comprises either no mismatches or no more than 1 or 2 mismatches to a corresponding region of the reverse complement of both the human GLI1 (SEQ ID NO 1) and GLI2 (SEQ ID NO 2) mRNA sequences.

5. The oligomer according to any one of embodiments 1-4, wherein the nucleotide sequence of the oligomer consists of the contiguous nucleotide sequence.

6. The oligomer according to any one of embodiments 1-5, wherein the contiguous nucleotide sequence is between 10-18 nucleotides in length.

7. The oligomer according to any one of embodiments 1-6, wherein the contiguous nucleotide sequence comprises nucleotide analogues.

8. The oligomer according to embodiment 7, wherein the nucleotide analogues are sugar modified nucleotides, such as sugar modified nucleotides selected from the group consisting of: Locked Nucleic Acid (LNA) units; 2-O-alkyl-RNA units, 2'-OMe-RNA units, 2'-amino-DNA units, and 2'-fluoro-DNA units.

9. The oligomer according to embodiment 8, wherein the nucleotide analogues are LNA.

10. The oligomer according to any one of embodiments 7-9 which is a gapmer.

11. The oligomer according to any one of embodiments 1-10, which inhibits the expression of GLI2 gene or mRNA in a cell which is expressing GLI2 gene or mRNA.

12. A conjugate comprising the oligomer according to any one of embodiments 1-11, and at least one non-nucleotide or non-polynucleotide moiety covalently attached to said oligomer.

13. A pharmaceutical composition comprising the oligomer according to any one of embodiments 1-11, or the conjugate according to embodiment 12, and a pharmaceutically acceptable diluent, carrier, salt or adjuvant.

14. The oligomer according to any one of embodiments 1-11, or the conjugate according to embodiment 12, for use as a medicament for the treatment or prevention of hyperproliferative disorders, such as cancer, for example, acute myeloid leukemia or preleukemia such as myelodysplastic syndrome or myeloproliferative disease.

15. The use of an oligomer according to any one of the embodiments 1-11, or a conjugate as defined in embodiment 12, for the manufacture of a medicament for the treatment or prevention of hyperproliferative disorders, such as cancer, for example, acute myeloid leukemia or preleukemia (myelodysplastic syndrome or myeloproliferative disease), in a mammal such as a human patient.

16. A method of treating hyperproliferative disorders, such as cancer, for example, for example, acute myeloid leukemia or preleukemia (myelodysplastic syndrome or myeloproliferative disease) in a mammal such as a human patient said method comprising administering an oligomer according to any one of the embodiments 1-11, or a conjugate according to embodiment 12, or a pharmaceutical composition according to embodiment 13, to a patient suffering from, or likely to suffer from hyperproliferative disorders, such as cancer, for example, acute myeloid leukemia or preleukemia such as myelodysplastic syndrome or myeloproliferative disease.

17. A method for the inhibition of GLI2 in a leukemic or preleukemic cell which is expressing GLI2, said method comprising contacting an oligomer according to any one of the embodiments 1-11, or a conjugate according to embodiment 12 with said cell so as to inhibit GLI2 in said cell, for example, by administering said oligomer or conjugate to a mammal such as a human patient suffering from acute myeloid leukemia or preleukemia such as myelodysplastic syndrome or myeloproliferative disease.

18. A method of inducing apoptosis in a leukemic or preleukemic cell which is expressing GLI2, said method comprising the step of contacting an oligomer according to any one of the embodiments 1-11, or a conjugate according to embodiment 12, or a pharmaceutical composition according to embodiment 13, with said cell in an amount sufficient to trigger apoptosis, for example, by administering said oligomer or conjugate to a mammal such as a human patient suffering from acute myeloid leukemia or preleukemia such as myelodysplastic syndrome or myeloproliferative disease.

19. Use of an oligomer according to any of embodiments 1-11, or a conjugate according to embodiment 12, or a pharmaceutical composition according to embodiment 13 in the manufacture of a medicament for preventing or delaying the advancement of preleukemia such as to acute myeloid leukemia in a mammal such as a human patient.

20. A method for preventing or delaying the advancement of preleukemia, such as such as myelodysplastic syndrome or myeloproliferative disease, to acute myeloid leukemia in a mammal such as a human patient, said method comprising the step of administering to the mammal an oligomer according to any of embodiments 1-11, or a conjugate according to embodiment 12, or a pharmaceutical composition according to embodiment 13.

21. Any one of embodiments 1-20 in which the oligomer includes or consists of an oligonucleotide selected from the group consisting of SEQ ID NOS: 112, 114, 118, 120, 130 and 132. In a variation, the oligomer includes or consists of an oligonucleotide selected from the group consisting of SEQ ID NOS: 118 and 132.

EXAMPLES

Example 1

Monomer Synthesis

The LNA monomer building blocks and derivatives were prepared following published procedures and references cited therein—see WO07/031081 and the references cited therein.

Example 2

Oligonucleotide Synthesis

Oligonucleotides (oligomers) were synthesized according to the method described in WO07/031081. Table 1 shows examples of antisense oligonucleotide motifs and of the invention.

Example 3

Design of the Oligonucleotides

In accordance with the invention, a series of oligonucleotides (oligomers) were designed to target different regions of the human GLI2 mRNA using the published sequence GenBank accession number NM_005270, presented herein as SEQ ID NO: 1. In some embodiments the oligonucleotides were also designed to target GLI1 mRNA using the published sequence GenBank accession number NM_005269 presented herein as SEQ ID NO: 2 and/or to target GLI3 mRNA using the published sequence GenBank accession number NM_000168 presented herein as SEQ ID NO: 134.

TABLE 1

Antisense oligonucleotide sequences of the invention.
SEQ ID NOs: 3-84 and SEQ ID NOs: 85-90 (shown in Table 2) are oligo motif sequences (oligomers) designed to target human GLI2 mRNA and optionally human GLI1 mRNA and optionally human GLI3 mRNA. (100% sequence homology with GLI1 mRNA is indicated—see "Compl Gli1").

| SEQ ID NO | Sequence (5'-3') | Length (bases) | Target site GLI2 | (Compl Gli1) |
|---|---|---|---|---|
| SEQ ID NO: 3 | ACCAGCATGTACTG | 14 | 1647-1660 | 100(%) |
| SEQ ID NO: 4 | ACCAGCATGTACT | 13 | | 100(%) |
| SEQ ID NO: 5 | CCAGCATGTACTG | 13 | | 100(%) |
| SEQ ID NO: 6 | ACCAGCATGTAC | 12 | | 100(%) |
| SEQ ID NO: 7 | CCAGCATGTACT | 12 | | 100(%) |
| SEQ ID NO: 8 | CAGCATGTACTG | 12 | | 100(%) |
| SEQ ID NO: 9 | AACGTGCACTTGTG | 14 | 1695-1708 | 100(%) |
| SEQ ID NO: 10 | TTCTGGTGCTTGGC | 14 | 1839-1852 | 100(%) |
| SEQ ID NO: 11 | TTCTGGTGCTTGG | 13 | | 100(%) |
| SEQ ID NO: 12 | TCTGGTGCTTGGC | 13 | | 100(%) |
| SEQ ID NO: 13 | TTCTGGTGCTTG | 12 | | 100(%) |
| SEQ ID NO: 14 | TCTGGTGCTTGG | 12 | | 100(%) |
| SEQ ID NO: 15 | CTGGTGCTTGGC | 12 | | 100(%) |
| SEQ ID NO: 16 | GTGAAGGCTGGGCTGA | 16 | 1030-1045 | |
| SEQ ID NO: 17 | TCTGCTTGTTCTGGTT | 16 | 1242-1257 | |
| SEQ ID NO: 18 | CCTGCTTACAGTCATC | 16 | 1458-1473 | |
| SEQ ID NO: 19 | CTCCTTGGTGCAGTCT | 16 | 1514-1529 | |
| SEQ ID NO: 20 | CTCCTTGGTGCAGTC | 15 | | |
| SEQ ID NO: 21 | TCCTTGGTGCAGTCT | 15 | | |
| SEQ ID NO: 22 | CTCCTTGGTGCAGT | 14 | | |
| SEQ ID NO: 23 | TCCTTGGTGCAGTC | 14 | | |
| SEQ ID NO: 24 | CCTTGGTGCAGTCT | 14 | | |
| SEQ ID NO: 25 | CTCCTTGGTGCAG | 13 | | |
| SEQ ID NO: 26 | TCCTTGGTGCAGT | 13 | | |
| SEQ ID NO: 27 | CCTTGGTGCAGTC | 13 | | |
| SEQ ID NO: 28 | CTTGGTGCAGTCT | 13 | | |
| SEQ ID NO: 29 | CTCCTTGGTGCA | 12 | | |
| SEQ ID NO: 30 | TCCTTGGTGCAG | 12 | | |
| SEQ ID NO: 31 | CCTTGGTGCAGT | 12 | | |
| SEQ ID NO: 32 | CTTGGTGCAGTC | 12 | | |
| SEQ ID NO: 33 | TTGGTGCAGTCT | 12 | | |
| SEQ ID NO: 34 | GTGTGTCTTCAGGTTC | 16 | 1742-1757 | |
| SEQ ID NO: 35 | CGCAGGTGTGTCTTCA | 16 | 1747-1762 | |
| SEQ ID NO: 36 | CGCAGGTGTGTCTTC | 15 | | |
| SEQ ID NO: 37 | GCAGGTGTGTCTTCA | 15 | | |
| SEQ ID NO: 38 | CGCAGGTGTGTCTT | 14 | | |

TABLE 1-continued

Antisense oligonucleotide sequences of the invention.
SEQ ID NOs: 3-84 and SEQ ID NOs: 85-90 (shown in Table 2) are
oligo motif sequences (oligomers) designed to target human GLI2
mRNA and optionally human GLI1 mRNA and optionally human GLI3 mRNA.
(100% sequence homology with GLI1 mRNA is indicated—see "Compl Gli1").

| SEQ ID NO | Sequence (5'-3') | Length (bases) | Target site GLI2 | (Compl Gli1) |
|---|---|---|---|---|
| SEQ ID NO: 39 | GCAGGTGTGTCTTC | 14 | | |
| SEQ ID NO: 40 | CAGGTGTGTCTTCA | 14 | | |
| SEQ ID NO: 41 | CGCAGGTGTGTCT | 13 | | |
| SEQ ID NO: 42 | GCAGGTGTGTCTT | 13 | | |
| SEQ ID NO: 43 | CAGGTGTGTCTTC | 13 | | |
| SEQ ID NO: 44 | AGGTGTGTCTTCA | 13 | | |
| SEQ ID NO: 45 | CGCAGGTGTGTC | 12 | | |
| SEQ ID NO: 46 | GCAGGTGTGTCT | 12 | | |
| SEQ ID NO: 47 | CAGGTGTGTCTT | 12 | | |
| SEQ ID NO: 48 | AGGTGTGTCTTC | 12 | | |
| SEQ ID NO: 49 | GGTGTGTCTTCA | 12 | | |
| SEQ ID NO: 50 | GCAGATGTAGGGTTTC | 16 | 1871-1886 | |
| SEQ ID NO: 51 | GCCACTGTCATTGTTG | 16 | 2213-2228 | |
| SEQ ID NO: 52 | CCAGGGCTGAGGTGTC | 16 | 2301-2316 | |
| SEQ ID NO: 53 | GAGGCAGCTTGGTGTT | 16 | 2451-2466 | |
| SEQ ID NO: 54 | TGCTGGTGGAGCTGTC | 16 | 2607-2622 | |
| SEQ ID NO: 55 | GTGAGGTTGAGCAGCC | 16 | 2818-2833 | |
| SEQ ID NO: 56 | GCCGCACAGGGTCGCT | 16 | 3096-3111 | |
| SEQ ID NO: 57 | ATGTAGTTTACCCTGG | 16 | 3838-3853 | |
| SEQ ID NO: 58 | CCATGAAGCCAGGCTG | 16 | 4230-4245 | |
| SEQ ID NO: 59 | TACATGTGGATCTGGC | 16 | 4534-4549 | |
| SEQ ID NO: 60 | TACATGTGGATCTGG | 15 | | |
| SEQ ID NO: 61 | ACATGTGGATCTGGC | 15 | | |
| SEQ ID NO: 62 | TACATGTGGATCTG | 14 | | |
| SEQ ID NO: 63 | ACATGTGGATCTGG | 14 | | |
| SEQ ID NO: 64 | CATGTGGATCTGGC | 14 | | |
| SEQ ID NO: 65 | TACATGTGGATCT | 13 | | |
| SEQ ID NO: 66 | ACATGTGGATCTG | 13 | | |
| SEQ ID NO: 67 | CATGTGGATCTGG | 13 | | |
| SEQ ID NO: 68 | ATGTGGATCTGGC | 13 | | |
| SEQ ID NO: 69 | TACATGTGGATC | 12 | | |
| SEQ ID NO: 70 | ACATGTGGATCT | 12 | | |
| SEQ ID NO: 71 | CATGTGGATCTG | 12 | | |
| SEQ ID NO: 72 | ATGTGGATCTGG | 12 | | |
| SEQ ID NO: 73 | TGTGGATCTGGC | 12 | | |

TABLE 1-continued

Antisense oligonucleotide sequences of the invention.
SEQ ID NOs: 3-84 and SEQ ID NOs: 85-90 (shown in Table 2) are
oligo motif sequences (oligomers) designed to target human GLI2
mRNA and optionally human GLI1 mRNA and optionally human GLI3 mRNA.
(100% sequence homology with GLI1 mRNA is indicated—see "Compl Gli1").

| SEQ ID NO | Sequence (5'-3') | Length (bases) | Target site GLI2 | (Compl Gli1) |
|---|---|---|---|---|
| SEQ ID NO: 74 | GCCATGTTGCTGATGC | 16 | 4864-4879 | |
| SEQ ID NO: 75 | TCAGATTCAAACCCA | 15 | 5330-5344 | |
| SEQ ID NO: 76 | TCAGATTCAAACCC | 14 | | |
| SEQ ID NO: 77 | CAGATTCAAACCCA | 14 | | |
| SEQ ID NO: 78 | TCAGATTCAAACC | 13 | | |
| SEQ ID NO: 79 | CAGATTCAAACCC | 13 | | |
| SEQ ID NO: 80 | AGATTCAAACCCA | 13 | | |
| SEQ ID NO: 81 | TCAGATTCAAAC | 12 | | |
| SEQ ID NO: 82 | CAGATTCAAACC | 12 | | |
| SEQ ID NO: 83 | AGATTCAAACCC | 12 | | |
| SEQ ID NO: 84 | GATTCAAACCCA | 12 | | |

Table 2 shows 24mer sequence motifs from which oligomers of the invention may be designed—the bold type represents oligomer sequence motifs as shown in Table 1.

| Corresponding 24 mer sequence | 24 mer SEQ ID | 16 mer SEQ ID |
|---|---|---|
| GCACCACCAGCATGTACTGCGCCT | SEQ ID NO: 85 | SEQ ID NO: 3 |
| TGCGATTCTGGTGCTTGGCGCGGT | SEQ ID NO: 86 | SEQ ID NO: 10 |
| CGTACTCCTTGGTGCAGTCTTCCC | SEQ ID NO: 87 | SEQ ID NO: 19 |
| GGACCGCAGGTGTGTCTTCAGGTT | SEQ ID NO: 88 | SEQ ID NO: 35 |
| TTCGTACATGTGGATCTGGCCGTA | SEQ ID NO: 89 | SEQ ID NO: 59 |
| AGCATTCAGATTCAAACCCAAATG | SEQ ID NO: 90 | SEQ ID NO: 75 |

TABLE 3

Oligonucleotide designs of the invention.
In the SEQ ID NOs: 91-111 upper case letters
indicates nucleotide (nucleoside) analogue units
(monomers), such as those disclosed herein, such
as LNA units. Lower case letters represent
nucleotide (DNA) monomers. In some embodiments the
internucleoside linkages between nucleotides are
all phosphorothioate. In some embodiments, all
cytosine bases (residues) in LNA monomers are
5-methyl cytosine.

| Sequence (5'-3') | |
|---|---|
| ACCagca☐tgtaCTG | SEQ ID NO: 91 |
| AACgtgcacttGTG | SEQ ID NO: 92 |

TABLE 3-continued

Oligonucleotide designs of the invention.
In the SEQ ID NOs: 91-111 upper case letters
indicates nucleotide (nucleoside) analogue units
(monomers), such as those disclosed herein, such
as LNA units. Lower case letters represent
nucleotide (DNA) monomers. In some embodiments the
internucleoside linkages between nucleotides are
all phosphorothioate. In some embodiments, all
cytosine bases (residues) in LNA monomers are
5-methyl cytosine.

| Sequence (5'-3') | |
|---|---|
| TTCtggtgcttGGC | SEQ ID NO: 93 |
| GTGaaggctgggcTGA | SEQ ID NO: 94 |
| TCTgcttgttctgGTT | SEQ ID NO: 95 |
| CCTgcttacagtcATC | SEQ ID NO: 96 |
| CTCcttggtgcagTCT | SEQ ID NO: 97 |
| GTGtgtcttcaggT☐TC | SEQ ID NO: 98 |
| CGCaggtgtgtctTCA | SEQ ID NO: 99 |
| GCAgatgtagggtTTC | SEQ ID NO: 100 |
| GCCactgtcattgTTG | SEQ ID NO: 101 |
| CCAgggctgaggtGTC | SEQ ID NO: 102 |
| GAGgcagcttggtGTT | SEQ ID NO: 103 |
| TGCtggtggagctGTC | SEQ ID NO: 104 |
| GTGaggttgagcaGCC | SEQ ID NO: 105 |
| GCCgcacagggtcGCT | SEQ ID NO: 106 |
| ATGtagtttacccTGG | SEQ ID NO: 107 |

TABLE 3-continued

Oligonucleotide designs of the invention.
In the SEQ ID NOs: 91-111 upper case letters
indicates nucleotide (nucleoside) analogue units
(monomers), such as those disclosed herein, such
as LNA units. Lower case letters represent
nucleotide (DNA) monomers. In some embodiments the
internucleoside linkages between nucleotides are
all phosphorothioate. In some embodiments, all
cytosine bases (residues) in LNA monomers are
5-methyl cytosine.

| Sequence (5'-3') | |
|---|---|
| CCAtgaagccaggCTG | SEQ ID NO: 108 |
| TACatgtggatctGGC | SEQ ID NO: 109 |
| GCCatgttgctgaTGC | SEQ ID NO: 110 |
| TCAgattcaaacCCA | SEQ ID NO: 111 |

Example 4

In Vitro Model: Cell Culture

The effect of antisense oligonucleotides on target nucleic acid expression can be tested in any of a variety of cell types provided that the target nucleic acid is present at measurable levels. The target can be expressed endogenously or by transient or stable transfection of a nucleic acid encoding said target nucleic acid. The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen. Cells were cultured in the appropriate medium as described below and maintained at 37° C. at 95-98% humidity and 5% $CO_2$. Cells were routinely passaged 2-3 times weekly.

DU-145:

The human prostate cancer cell line DU-145 was cultured in RPMI 1640 medium with glutamax I (Gibco #61870-010) containing 10% fetal bovine serum (Biochrom 19357-5010) and 25 µg/ml Gentamicin (25 µg/ml) (Sigma # G1397).

518A2:

The human melanoma cancer cell line 518A2 was cultured in Dulbecco's MEM (Sigma # D5671), containing 10% fetal bovine serum (Biochrom 19357-5010), 2 mM Glutamax I (Gibco #35050-038) and 25 µg/ml Gentamicin (Sigma # G1397).

Example 5

In Vitro Model: Treatment with Antisense Oligonucleotide

The cells were treated with an oligomer (oligonucleotide) using the cationic liposome formulation LipofectAMINE 2000 (Gibco) as transfection vehicle. Cells were seeded in 6-well cell culture plates (NUNC) and treated when 75-90% confluent. Oligonucleotide concentrations used ranged from 0.8 nM to 20 nM final concentration. Formulation of oligonucleotide-lipid complexes were carried out essentially as described by the manufacturer using serum-free OptiMEM (Gibco) and a final lipid concentration of 5 µg/mL LipofectAMINE 2000. Cells were incubated at 37° C. for 4 hours and treatment was stopped by removal of oligonucleotide-containing culture medium. Cells were washed and serum-containing media was added. After oligonucleotide treatment, cells were allowed to recover for 20 hours before they were harvested for RNA analysis.

Example 6

In Vitro Model: Extraction of RNA and cDNA Synthesis

For RNA isolation from the cell lines, the RNeasy mini kit (Qiagen cat. no. 74104) was used according to the protocol provided by the manufacturer. First strand synthesis was performed using Reverse Transcriptase reagents from Ambion according to the manufacturer's instructions.

For each sample, 0.5 µg total RNA was adjusted to (10.8 µl) with RNase free $H_2O$ and mixed with 2 µl random decamers (50 µM) and 4 µl dNTP mix (2.5 mM each dNTP) and heated to 70° C. for 3 min after which the samples were rapidly cooled on ice. After cooling the samples on ice, 2 µl 10× Buffer RT, 1 µl MMLV Reverse Transcriptase (100 U/µl) and 0.25 µl RNase inhibitor (10 U/µl) was added to each sample, followed by incubation at 42° C. for 60 min, heat inactivation of the enzyme at 95° C. for 10 min and then the sample was cooled to 4° C.

Example 7

In Vitro Model: Analysis of Oligonucleotide Inhibition of GLI2 Expression by Real-Time PCR Antisense modulation of GLI2 mRNA expression can be assayed in a variety of ways known in the art. For example, GLI2 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis is routine in the art and is taught in, for example, Current Protocols in Molecular Biology, John Wiley and Sons. Real-time quantitative (PCR) can be conveniently accomplished using the commercially available Multi-Color Real Time PCR Detection System, available from Applied Biosystem.

Real-time Quantitative PCR Analysis of GLI2 mRNA Levels

The content of human GLI2 mRNA in the samples was quantified using the human GLI2 ABI Prism Pre-Developed TaqMan Assay Reagent (Applied Biosystems cat. no. Hs00257977_m1) according to the manufacturer's instructions.

The content of human GLI1 (also referred herein as Gli1) mRNA in the samples was quantified using the human Gli1 ABI Prism Pre-Developed TaqMan Assay Reagent (Applied Biosystems cat. no. Hs00171790_m1) according to the manufacturer's instructions. Glyceraldehyde-3-phosphate dehydrogenase (GAPDH) mRNA quantity was used as an endogenous control for normalizing any variance in sample preparation.

The content of human GAPDH mRNA in the samples was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example Heid et al. Real time quantitative PCR, Genome Research (1996), 6: 986-994.

Real Time PCR

The cDNA from the first strand synthesis performed as described in Example 6 was diluted 2-20 times, and analyzed by real time quantitative PCR using Taqman 7500 FAST from Applied Biosystems. The primers and probe were mixed with 2× Taqman Fast Universal PCR master mix (2×) (Applied Biosystems Cat.#4364103) and added to 4 μl cDNA to a final volume of 10 μl. Each sample was analysed in triplicate. Standard curves were generated by assaying 2-fold dilutions of a cDNA that had been prepared on material purified from a cell line expressing the RNA of interest. Sterile H₂O was used instead of cDNA for the no template control. PCR program: 95° C. for 30 seconds, followed by 40 cycles of 95° C., 3 seconds, 60° C., 30 seconds. Relative quantities of target mRNA sequence were determined from the calculated Threshold cycle using the Applied Biosystems Fast System SDS Software Version 1.3.1.21.

Example 8

In Vitro Analysis: Antisense Inhibition of Human GLI2 Expression by Oligonucleotides Oligonucleotides were evaluated for their potential to knockdown GLI2 mRNA expression at concentrations of 0.8, 4 and 20 nM in DU-145 cells and 518A2 cells (see FIGS. 4, 5 and 6). The data are presented in Table 4 as percentage downregulation of GLI2 mRNA relative to mock transfected cells at 4 nM. Mock transfected cells were transfected with a scrambled control (a negative control). Said scrambled control is an oligomer, such as the oligomer having the sequence shown as SEQ ID No: 133, which does not have complementarity to the target sequence. Lower case letters represent DNA units, bold upper case letters represent LNA such as β-D-oxy-LNA units. All cytosine bases in the LNA monomers are 5-methylcytosine. Subscript "s" represents phosphorothioate linkage.

TABLE 4

| Test substance | Sequence (5'-3') | GLI2 mRNA (% Inhib) |
|---|---|---|
| SEQ ID NO: 112 | $A_sC_sC_sa_sg_sc_sa_s{\square}t_sg_st_sa_sC_sT_sG$ | 72.8 |
| SEQ ID NO: 113 | $A_sA_sC_sg_st_sg_sc_sa_sc_st_st_sG_sT_sG$ | 55.2 |
| SEQ ID NO: 114 | $T_sT_sC_st_sg_sg_st_sg_sc_st_st_sG_sG_sC$ | 79.6 |
| SEQ ID NO: 115 | $G_sT_sG_sa_sa_sg_sg_sc_st_sg_sg_sg_sc_sT_sG_sA$ | 82.3 |
| SEQ ID NO: 116 | $T_sC_sT_sg_sc_st_st_sg_sg_st_st_sc_st_sg_sG_sT_sT$ | 71.9 |
| SEQ ID NO: 117 | $C_sC_sT_sg_sc_st_st_sa_sc_sa_sg_st_sc_sA_sT_sC$ | 62.2 |
| SEQ ID NO: 118 | $C_sT_sC_sc_st_st_sg_sg_st_sg_sc_sa_sg_sT_sC_sT$ | 79.9 |
| SEQ ID NO: 119 | $G_sT_sG_st_sg_st_sc_st_st_sc_sa_sg_sg_sT_s{\square}T_sC$ | 68.4 |
| SEQ ID NO: 120 | $C_sG_sC_sa_sg_sg_st_sg_st_sg_st_sc_st_sT_sC_sA$ | 71.4 |
| SEQ ID NO: 121 | $G_sC_sA_sg_sa_st_sg_st_sa_sg_sg_sg_st_sT_sT_sC$ | 74.9 |
| SEQ ID NO: 122 | $G_sC_sC_sa_sc_st_sg_st_sc_sa_st_st_sg_sT_sT_sG$ | 63.7 |
| SEQ ID NO: 123 | $C_sC_sA_sg_sg_sg_sc_st_sg_sa_sg_sg_st_sG_sT_sC$ | 66.8 |
| SEQ ID NO: 124 | $G_sA_sG_sg_sc_sa_sg_sc_st_st_sg_sg_st_sG_sT_sT$ | 37.6 |
| SEQ ID NO: 125 | $T_sG_sC_st_sg_sg_st_sg_sg_sa_sg_sc_st_sG_sT_sC$ | 31.6 |
| SEQ ID NO: 126 | $G_sT_sG_sa_sg_sg_st_st_sg_sa_sg_sc_sa_sG_sC_sC$ | 70.3 |
| SEQ ID NO: 127 | $G_sC_sC_sg_sc_sa_sc_sa_sg_sg_sg_st_sc_sG_sC_sT$ | 42.8 |
| SEQ ID NO: 128 | $A_sT_sG_st_sa_sg_st_st_st_sa_sc_sc_sc_sT_sG_sG$ | 71.4 |
| SEQ ID NO: 129 | $C_sC_sA_st_sg_sa_sa_sg_sc_sc_sa_sg_sg_sC_sT_sG$ | 73.7 |
| SEQ ID NO: 130 | $T_sA_sC_sa_st_sg_st_sg_sg_sa_st_sc_st_sG_sG_sC$ | 69.2 |
| SEQ ID NO: 131 | $G_sC_sC_sa_st_sg_st_st_sg_sc_st_sg_sa_sT_sG_sC$ | 62.4 |
| SEQ ID NO: 132 | $T_sC_sA_sg_sa_st_st_sc_sa_sa_sa_sc_sC_sC_sA$ | 79.7 |
| SEQ ID NO: 133 | $C_sG_sT_sc_sa_sg_st_sa_st_sg_sc_sg_sA_sA_sT_sc$ | control oligo |

As shown in Table 4, all the tested oligonucleotides targeting GLI2 mRNA expression provided an inhibition of at least 30% at the low dosage of 4 nM. SEQ ID NO 113, 117, 119, 122, 123, 130 and 131 all gave at least 50% inhibition at the low dosage of 4 nM, and SEQ ID NO 112, 114, 115, 116, 118, 120, 121, 126, 128, 129 and 132 all gave at least 70% inhibition at 4 nM dosage.

Oligomers (also referred herein as oligos) having the sequence shown as SEQ ID NO 117, 119, 122, 123, 130, 131, 112, 114, 115, 116, 118, 120, 121, 126, 128, 129 and 132 all gave at least 60% inhibition at 4 nM dosage, and are therefore, in some embodiments, preferred, as well as oligonucleotides based on the illustrated antisense oligomer sequences, for example varying the length (shorter or longer) and/or nucleobase content (e.g. the type and/or proportion of analogue units), which also provide good inhibition of GLI2 mRNA expression.

Example 9

In Vitro Analysis: Antisense Inhibition of Human GLI1 Expression and Human GLI3 Expression by Oligonucleotides Oligonucleotides were evaluated for their potential to knockdown GLI1 mRNA at concentrations of 0.8, 4 and 20 nM in DU-145 cells and 518A2 cells (see FIGS. 7 and 8).

Figure 9:
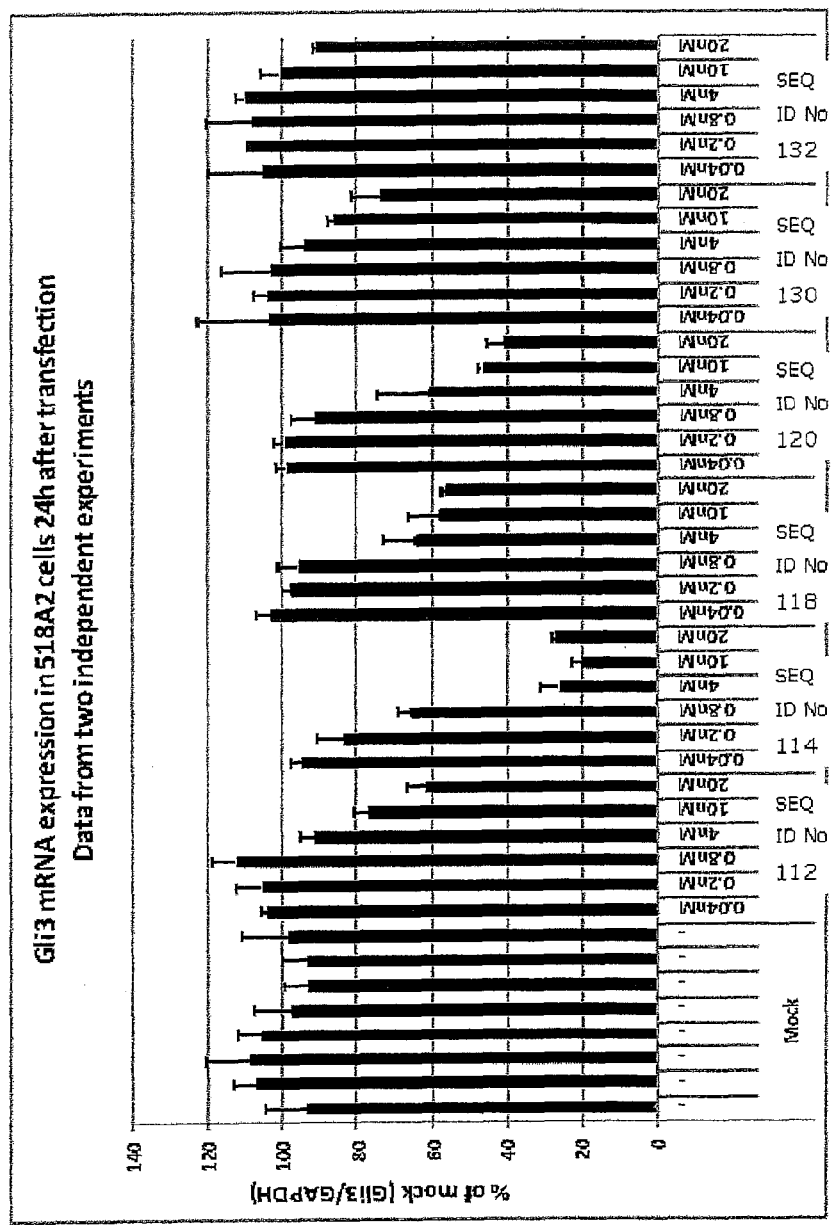
FIG. 9: GLI3 mRNA expression in 518A2 cells 24 h after transfection with GLI2 oligomers. Q-PCR data from 518A2 cells 24 h after transfection with GLi2 oligomers. The data have been normalised with GAPDH mRNA expression and are compared to target expression in mock (100%). Mock transfected cells are transfected with the transfection agent only (negative control).

Oligonucleotides were evaluated for their potential to knockdown GLI3 mRNA at concentrations of 0.8, 4 and 20 nM in 518A2 cells (see FIG. 9).

Example 10

Apoptosis Induction by LNA Oligonucleotides

518A2 cells were seeded in 6-well culture plates (NUNC) the day before transfection at a density of $1.5 \times 10^5$ cells/well and DU-145 cells at a density of $2.8 \times 10^5$ cells/well. The cells were treated with oligonucleotide using the cationic liposome formulation LipofectAMINE 2000 (Gibco) as transfection vehicle when 75-90% confluent. The oligomer concentrations used were 4 nM and 20 nM (final concentration in well). Formulation of oligomer-lipid complexes were carried out essentially as described by the manufacturer using serum-free OptiMEM (Gibco) and a final lipid concentration of 5 μg/mL LipofectAMINE 2000. Cells were incubated at 37° C. for 4 hours and treatment was stopped by removal of oligomer-containing culture medium. After washing with Optimem, 300 μl of Trypsin was added to each well until the cells detached from the wells. The trypsin was inactivated by adding 3 ml HUH7 culture media to the well and a single cell suspension was made by gently pipetting the cell suspension up and down. The scrambled oligo (oligomer) SEQ ID NO: 133 was used as control.

Following this, 100 μl of the cell suspension was added to each well of a white 96-well plate from Nunc (cat #136101) (four plates were prepared, for measurement at different time points). The plates were then incubated at 37° C., 95% humidity and 5% $CO_2$ until the assays were performed.

Figure 13:
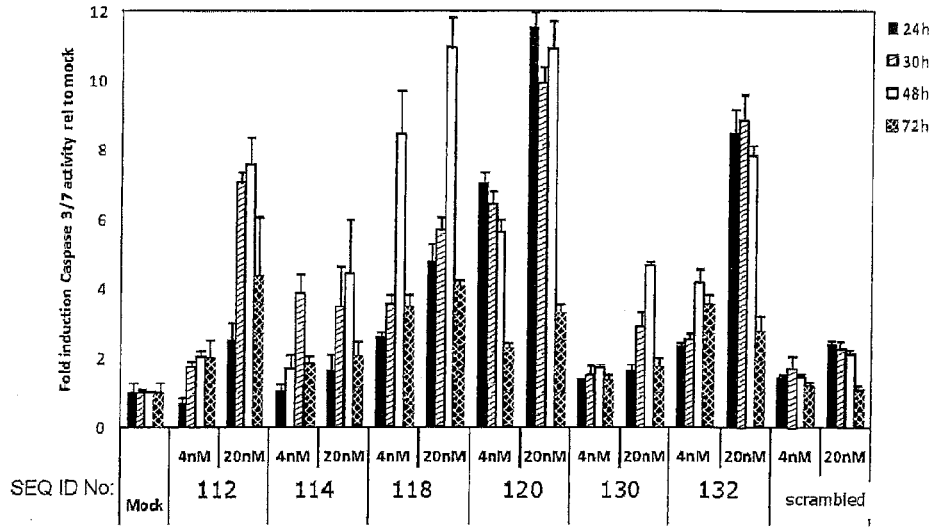
FIG. 13: Caspase 3/7 assay in DU-145 cells. The caspase 3/7 assay was performed in DU-145 cells using 4 nM and 20 nM final oligomer concentrations. The scrambled control was used as negative control. Mock refers to no oligomer control—i.e. the mock transfected cells were transfected with the transfection agent only (negative control). The SEQ ID No of the oligomer used is indicated under the bars of the graph.
Figure 14:
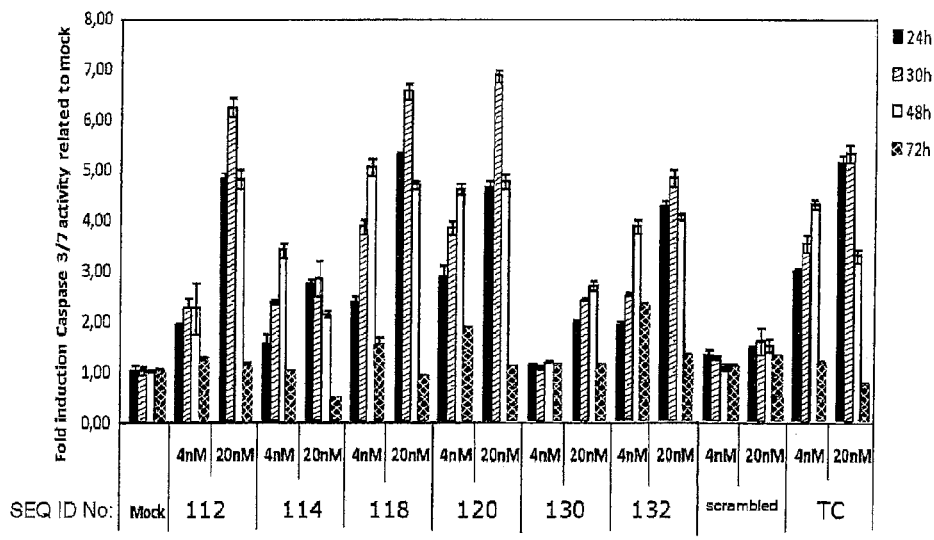
FIG. 14: Caspase 3/7 assay in 518A2 cells. The caspase 3/7 assay was performed in 518A2 cells using 4 nM and 20 nM final oligomer concentrations. The scrambled control was used as negative control. Mock refers to no oligomer control. Toxic oligomer (TC) is an oligomer that has been shown to be toxic both in vitro and in vivo and was used as a positive control. The SEQ ID No of the oligomer used is indicated under the bars of the graph.

Caspase Assay:

The activity of apoptosis specific caspases 3 and 7 was measured using a luminogenic Caspase-Glo 3/7-substrate assay (Cat#G8091 from Promega). The plate to be analyzed was equilibrated to room temperature for 15 min. The Caspase-Glo® 3/7 buffer was mixed with the Caspase-Glo 3/7 substrate to a Caspase-Glo® working solution which was equilibrated to room temperature. Then, 100 μl of the Caspase-Glo® working solution was carefully added to the medium in each well of the 96-well plate (it is important to avoid bubbles and contamination between wells). The plate was carefully shaken for 1 min, after which it was incubated at room temperature for 1 h, protected from light. The caspase activity was measured as Relative Light Units per second (RLU/s) in a Luminoscan Ascent instrument (Thermo Labsystems). Data were correlated and plotted relative to an average value of the mock samples, which was set to 1. See FIGS. 13 and 14.

Example 11

In Vitro Inhibition of Proliferation Using LNA Oligonucleotides

518A2 cells were transfected and harvested into a single cell suspension as described in Example 10 (apoptosis induction). SEQ ID NO: 133 served as a scrambled control. Following this, 100 μl of the cell suspension was added to each well of a 96-well plate ("Orange Scientific") for MTS assay (four plates were prepared, for measurement at different time points). The plates were then incubated at 37° C., 95% humidity and 5% $CO_2$ until the assays were performed.

Measurement of Proliferating Viable Cells (MTS Assay)

For the proliferation assay, 10 μl CellTiter 96® AQueous One Solution Cell Proliferation Assay (Promega, G3582) was added to the medium of each well of the 96-well plate, the plate was carefully shaken, and incubated at 37° C., 95% humidity and 5% $CO_2$ for 1 h before measurement. The absorbance was measured at 490 nm in a spectrophotometer and background for the assay was subtracted from wells containing only medium. The absorbance at 490 nm is proportional to the number of viable cells and was plotted over time for the mock transfected cells and for cells transfected with oligomer. See FIG. 11.

Example 12

Preparation of a Conjugate of SEQ ID NO: 112, 114, 118, 120, 130 and 132 and Polyethylene Glycol An oligomer is functionalized on the 5' terminus by attaching an aminoalkyl group, such as hexan-1-amine blocked with a blocking group such as Fmoc to the 5' phosphate group of the oligomer using routine phosphoramidite chemistry, oxidizing the resultant compound, deprotecting it and purifying it to achieve the functionalized oligomer (an activated oligomer) having the formula (I):

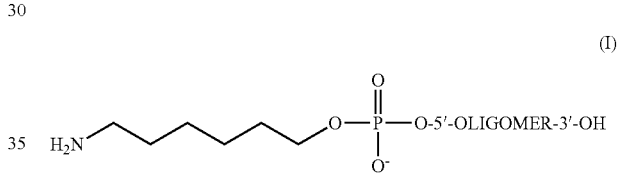

The term oligomer in formula (I) or (III) refers to an oligomer of the invention—such as an oligomer selected from the group consisting of SEQ ID NO: 112, 114, 118, 120, 130 and 132.

A solution of activated PEG, such as the one shown in formula (II):

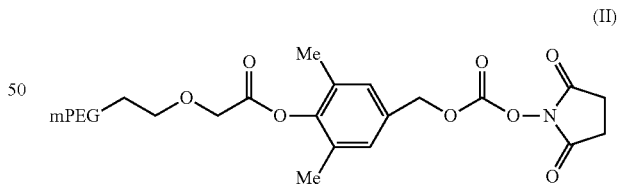

wherein the PEG moiety has an average molecular weight of 12,000, and the compound of formula (I) in PBS buffer is stirred at room temperature for 12 hours. The reaction solution is extracted three times with methylene chloride and the combined organic layers are dried over magnesium sulphate and filtered and the solvent is evaporated under reduced pressure. The residue is dissolved in double distilled water and loaded onto an anion exchange column. Unreacted PEG linker is eluted with water and the product is eluted with $NH_4HCO_3$ solution. Fractions containing pure product are pooled and lyophilized to yield the conjugate of formula (III):

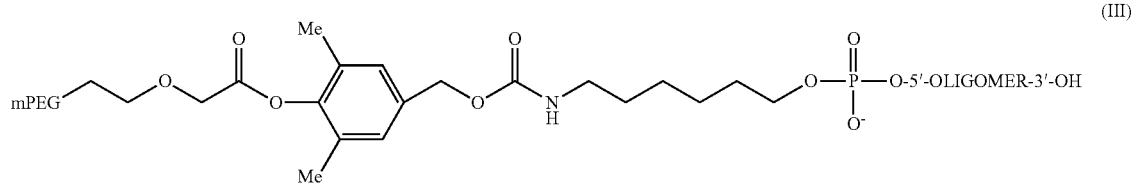

(III)

wherein the oligomer (for example, SEQ ID NO: 112, 114, 118, 120, 130 and 132) is attached to a PEG polymer having average molecular weight of 12,000 via a releasable linker.

Example 13

IC50 Determination in DU-145 and 518A2 Cells with Respect to Gli1, Gli2 and Gli3 mRNA Expression See Examples 4-9 for experimental details.

Figure 5:
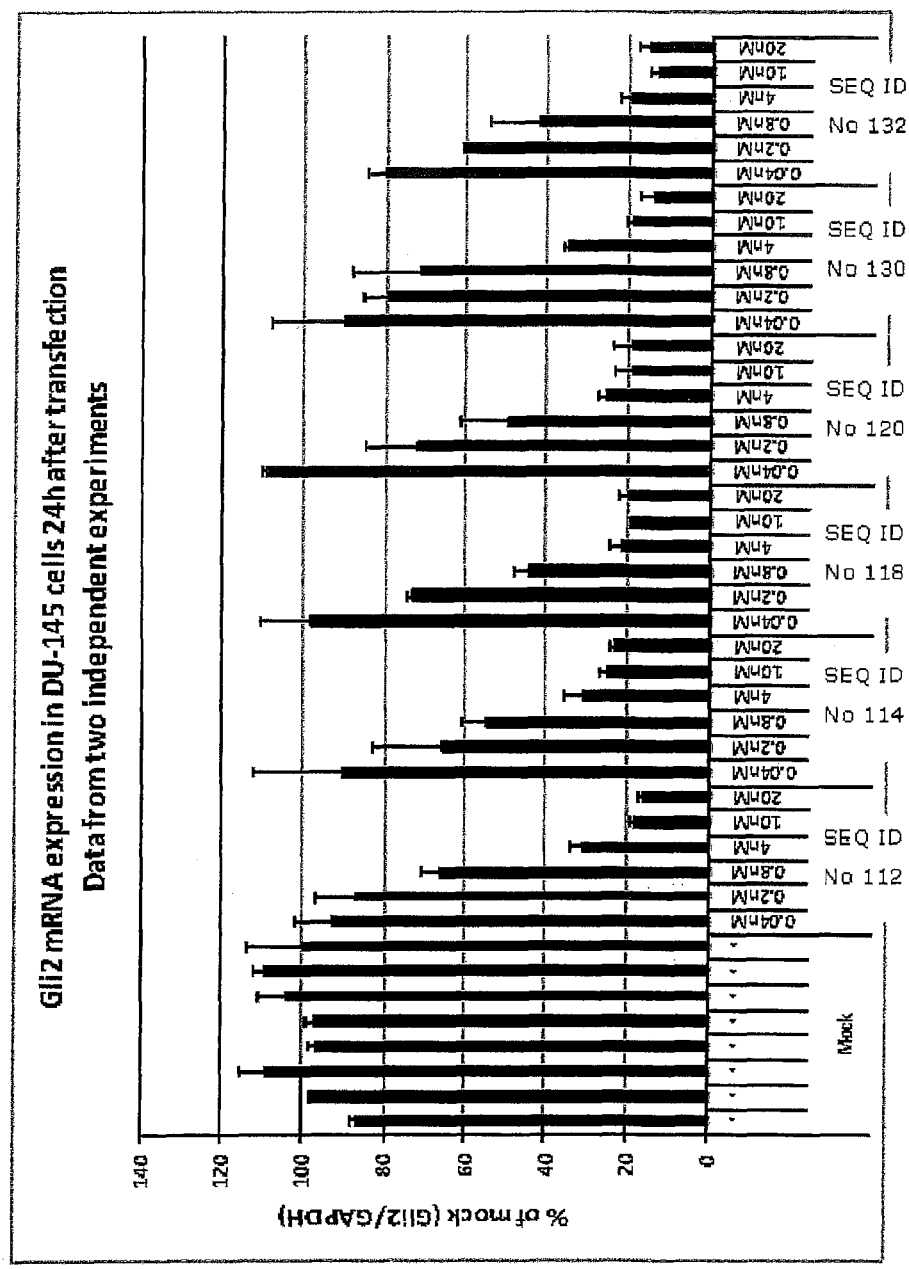
FIG. 5: GLI2 mRNA expression in DU-145 cells 24 h after transfection with GLI2 oligomers. Q-PCR (quantitative PCR) data from DU-145 cells 24 h after transfection with GLi2 oligomers (which may be referred to as oligos). The data have been normalised with GAPDH mRNA expression and are compared to target expression in mock (100%). Mock transfected cells are transfected with the transfection agent only (negative control).
Figure 6:
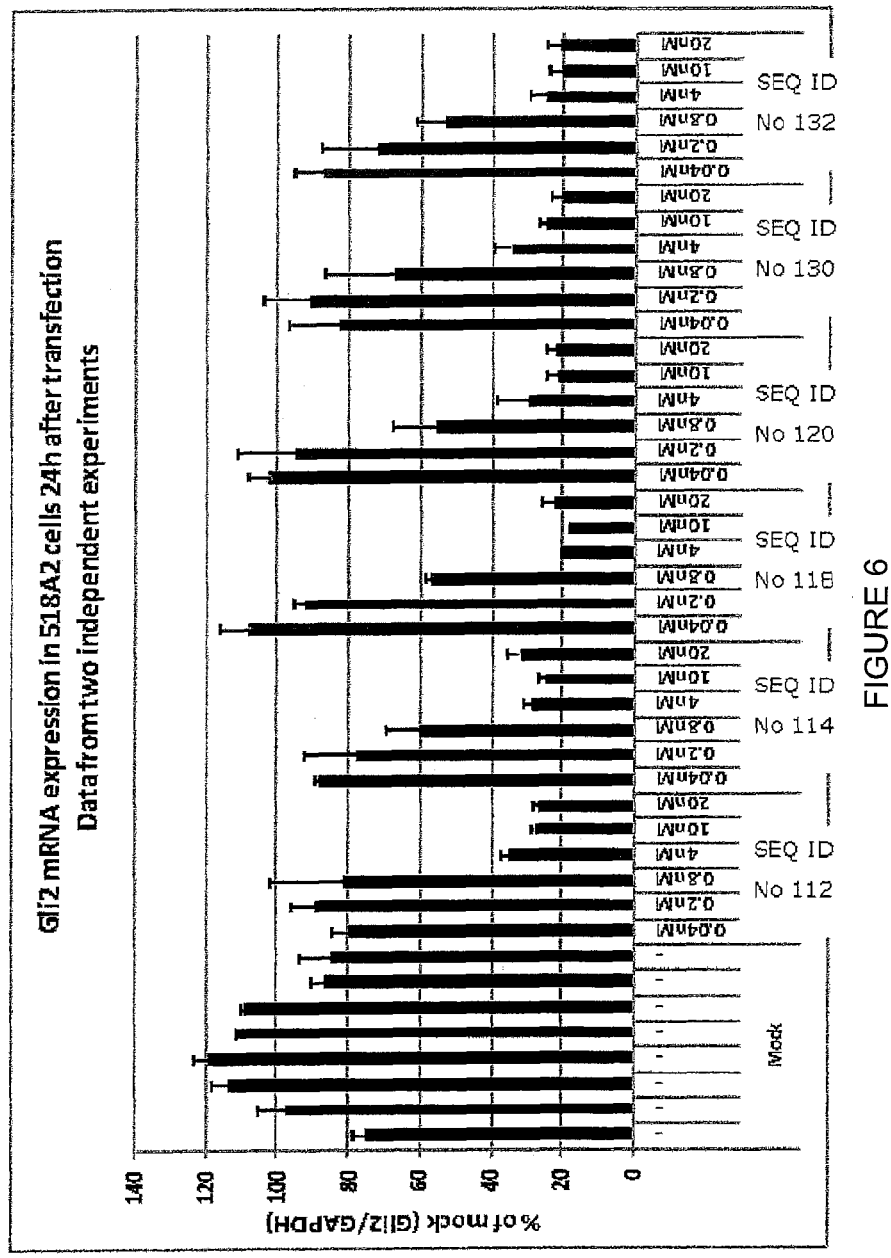
FIG. 6: GLI2 mRNA expression in 518A2 cells 24 h after transfection with GLI2 oligomers. Q-PCR data from 518A2 cells 24 h after transfection with GLi2 oligomers. The data have been normalised with GAPDH mRNA expression and are compared to target expression in mock (100%). Mock transfected cells are transfected with the transfection agent only (negative control).

$IC_{50}$ values for the different GLI2 oligomers with respect to GLI2 mRNA expression were determined in DU-145 cells and 518A2 cells. The cells were transfected with oligomers in concentrations ranging from 0.04 nM to 20 nM final concentration. GLI2 (also referred to herein as GLi2) mRNA expression was determined 24 h after transfection by qPCR (quantitative PCR). The results are shown in FIGS. 4, 5 and 6. All oligomers showed potent downregulation of GLI2 mRNA 24 h after transfection, with IC50:s below 4 nM in both cell lines.

Figure 7:
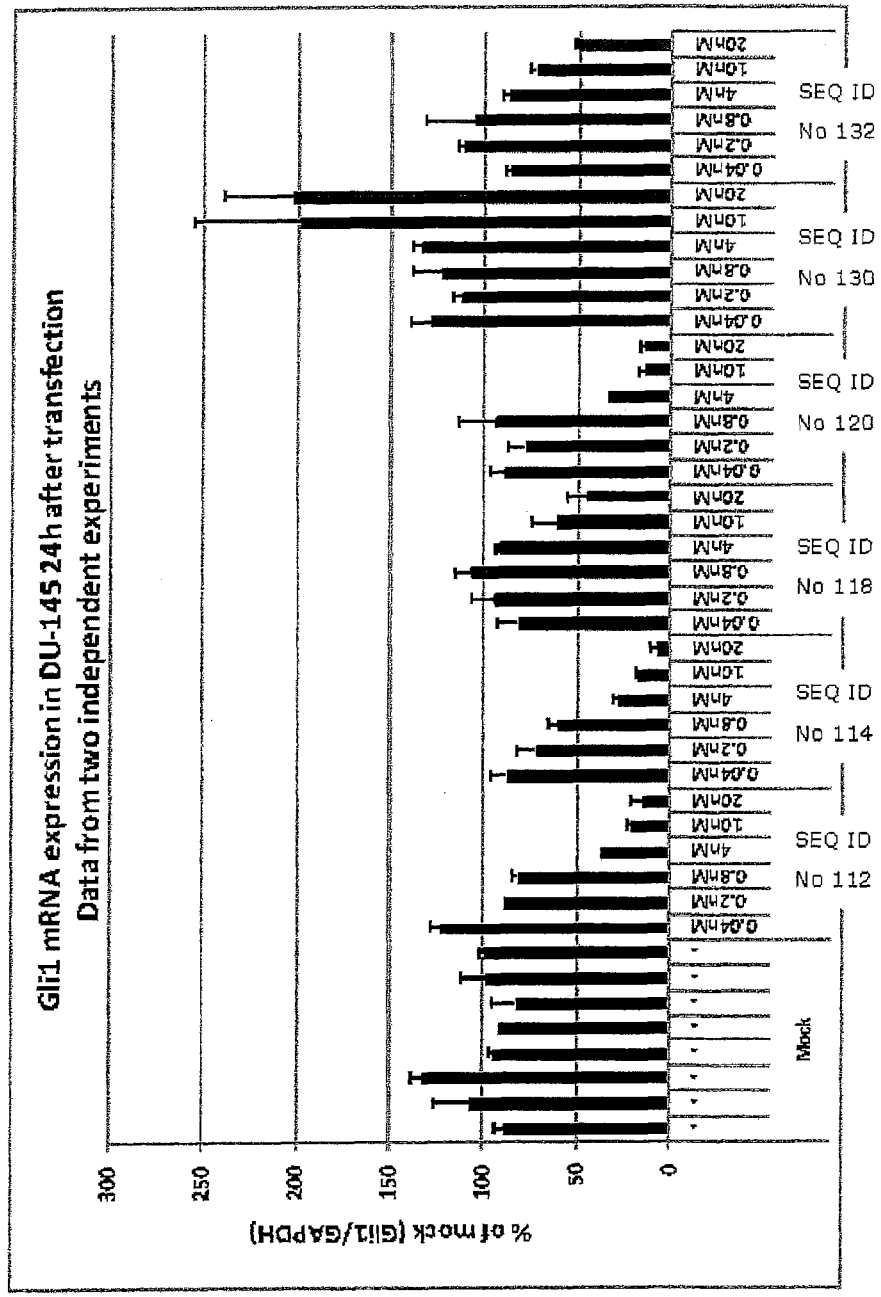
FIG. 7: GLI1 mRNA expression in DU-145 cells 24 h after transfection with GLI2 oligomers. Q-PCR data from DU-145 cells 24 h after transfection with GLI2 oligomers. The data have been normalised with GAPDH mRNA expression and are compared to target expression in mock (100%). Mock transfected cells are transfected with the transfection agent only (negative control).
Figure 8:
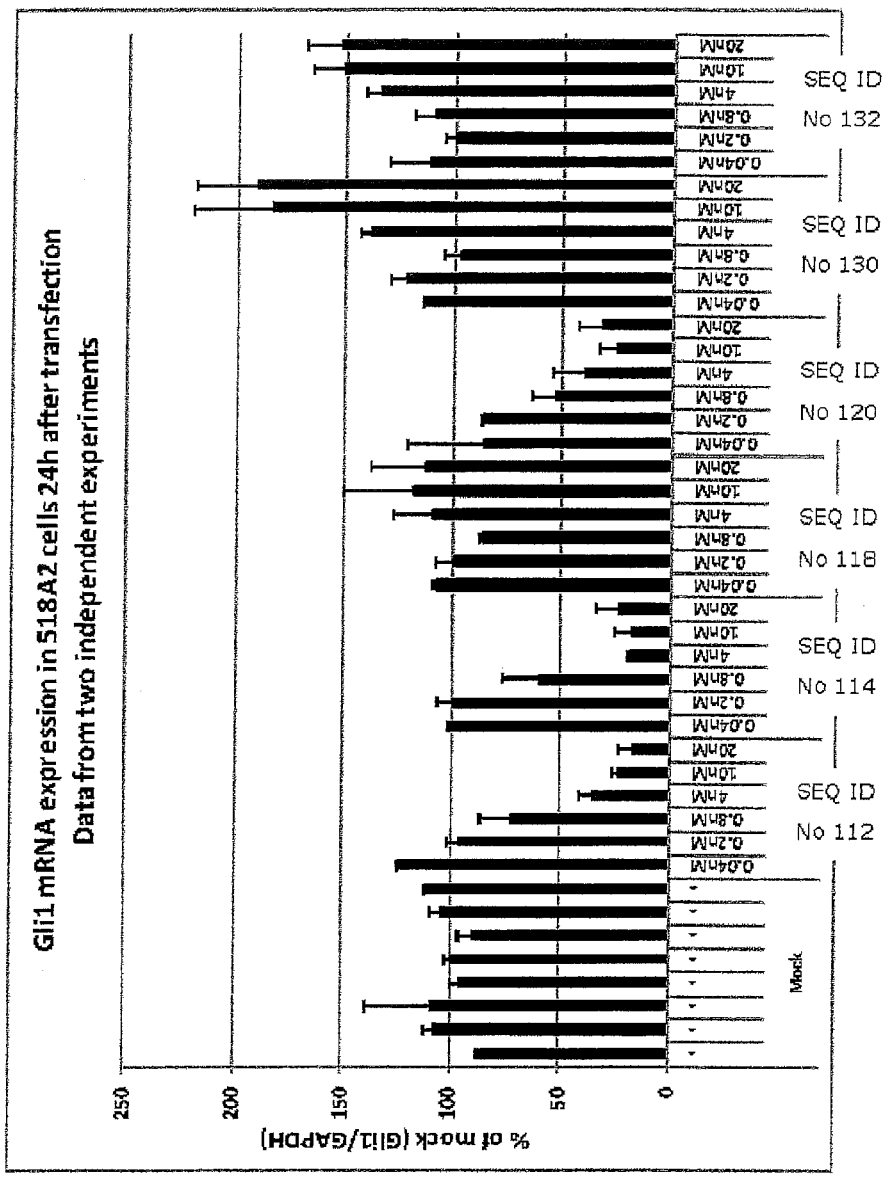
FIG. 8: Gli1 mRNA expression in 518A2 cells 24 h after transfection with GLI2 oligomers. Q-PCR data from 518A2 cells 24 h after transfection with GLI2 oligomers. The data have been normalised with GAPDH mRNA expression and are compared to target expression in mock (100%). Mock transfected cells are transfected with the transfection agent only (negative control).

$IC_{50}$ values for the different GLI2 oligomers with respect to GLI1 mRNA expression were determined in DU-145 cells and 518A2 cells. The cells were transfected with oligomers in concentrations ranging from 0.04 nM to 20 nM final concentration. GLI1 mRNA expression was determined 24 h after transfection by qPCR. The results are shown in FIGS. 7 and 8. The bi-specific Gli2 oligomers, SEQ ID NO 112 and 114, showed potent downregulation of GLI1 with IC50:s below 4 nM in both DU-145 and 518A2 cells when analysed 24 h after transfection. In addition, SEQ ID NO 120 showed knockdown of GLI1 (reduced expression of Gli1 mRNA) in both cell lines, with the most potent knockdown found in DU-145 cells. SEQ ID NO 120 has only 1 mismatch to GLI1, which is likely to be the reason for the observed knockdown of GLI1 with this oligomer. In contrast, SEQ ID NO 130 seemed to induce GLI1 expression at the concentrations 10 nM and 20 nM in both DU-145 and 518A2 cells.

The expression of GLI3 (also referred to herein as Gli3) was investigated in 518A2 cells after transfection with the GLI2 oligomers. The expression was not analysed in DU-145 cells, as these cells express very low levels of GLI3 mRNA (under detection limit for qPCR). All oligomers had been designed with at least two mismatches to GLI3, as it was desirable to avoid targeting of GLI3 with the oligomers. The results are shown in FIG. 9. The results showed that SEQ ID NO 114 showed potent knockdown of GLI3 mRNA expression, with an IC50 below 4 nM. SEQ ID NO 118 and SEQ ID NO 120 showed down-regulation of GLI3 with IC50:s above 20 nM (118) or between 10-20 nM (120), while the remaining oligomers had no or only slight effect on GLI3 mRNA expression at the highest concentrations.

Example 14

Plasma Stability of the GLI2 Oligomers

Mouse plasma (Lithium heparin plasma from BomTac: NMRI mice, collected 14-09-05, Taconic Europe) was defrosted and aliquoted into tubes with 45 µl plasma/tube. Following, 5 µl oligomer (200 µM) was added to the 45 µl plasma to a final concentration of 20 µM. After thorough mixing, the samples were incubated at 37° C. for 0-120 hrs. At different time points (0 h, 24 h, 48 h and 120 h) samples were collected and the reaction was quenched by snap freezing the samples in liquid nitrogen. For analysis, samples were added to loading buffer and analysed by electrophoresis on a PAGE-sequencing gel under denaturing conditions.

Figure 10:
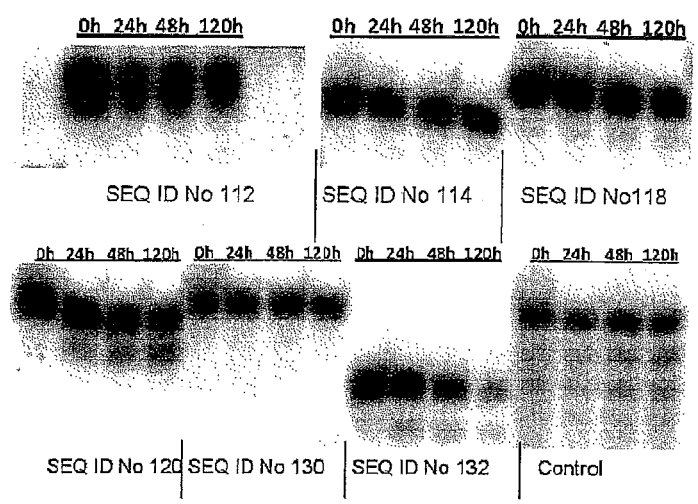
FIG. 10: Stability determinations of LNA oligomers in mouse plasma. The LNA oligomers were incubated with mouse plasma at 37° C. and aliquots were taken at 0, 24, 48 and 120 h. The results are visualized by gel electrophoresis using an SDS-PAGE gel. A DNA phosphorothioate was used as positive control oligomer showing degradation of the oligomers. The SEQ ID No of the oligomer used is indicated under each gel.

The results from the plasma stability assay demonstrated that the oligomers were very stable. All oligomers showed in-vitro stability whereby more than 90% of active compound remained after 24 h when incubated with mouse plasma at 37° C. h. For oligomers having sequences shown as SEQ ID NO: 120 and SEQ ID NO: 132, which have an A-residue at the 3'-end, a weak N−1 band could be detected starting after 24 h incubation, while no degradation could be detected for any of the other oligomers. We have previously observed that oligomers with an A-residue at the 3'-end show weak N−1 bands after incubation in plasma, which is probably due to depurination. The results are shown in FIG. 10.

Example 15

$T_m$ Determination of the GLI2 Oligomers

The melting temperature of the LNA oligomer/RNA duplexes was determined using a UV-spectrometry system with corresponding software (Perkin Elmer, Fremont, USA). The LNA oligomer and its complementary RNA were added in final concentrations of 1.5 µM to the $T_m$-buffer (200 nM NaCl, 0.2 nM EDTA, 20 mM NaP, pH 7.0). Duplex formation was prepared by heating the samples to 95° C. for 3 min followed by cooling at room temperature for 30 min.

Melting temperature ($T_m$) values were measured in a Lambda 25 UV/VIS spectrometer (Perkin Elmer) and data was collected and analysed using the TempLab software (Perkin Elmer). The instrument was programmed to heat the oligomer duplex sample from 20-95° C. and afterwards cooling the sample to 25° C. During this process the absorbance at 260 nm was recorded. The melting curves were used to calculate $T_m$ values (Table 5).

TABLE 5

Tm of the LNA oligomers against complementary RNA as determined by UV-spectrophotometry.

| SEQ ID NO | Tm |
|---|---|
| 112 | 63.8° C. |
| 114 | 72.2° C. |
| 118 | 72.9° C. |
| 120 | 70.5° C. |
| 130 | 65.0° C. |
| 132 | 60.7° C. |

All GLI2 oligomers had a $T_m$ above 60° C. against their complementary RNA.

Example 16

Proliferation Assay in DU-145 and 518A2 Cells

MTS assay: For the proliferation assay, 10 µl CellTiter 96® AQueous One Solution Cell Proliferation Assay (Promega, G3582) was added to the medium of each well of the 96-well plate, the plate was carefully shaken, and incubated at 37° C., 95% humidity and 5% $CO_2$ for 1 h before measurement. The absorbance was measured at 490 nm in a spectrophotometer and background for the assay was subtracted from wells containing only medium.

Figure 11:
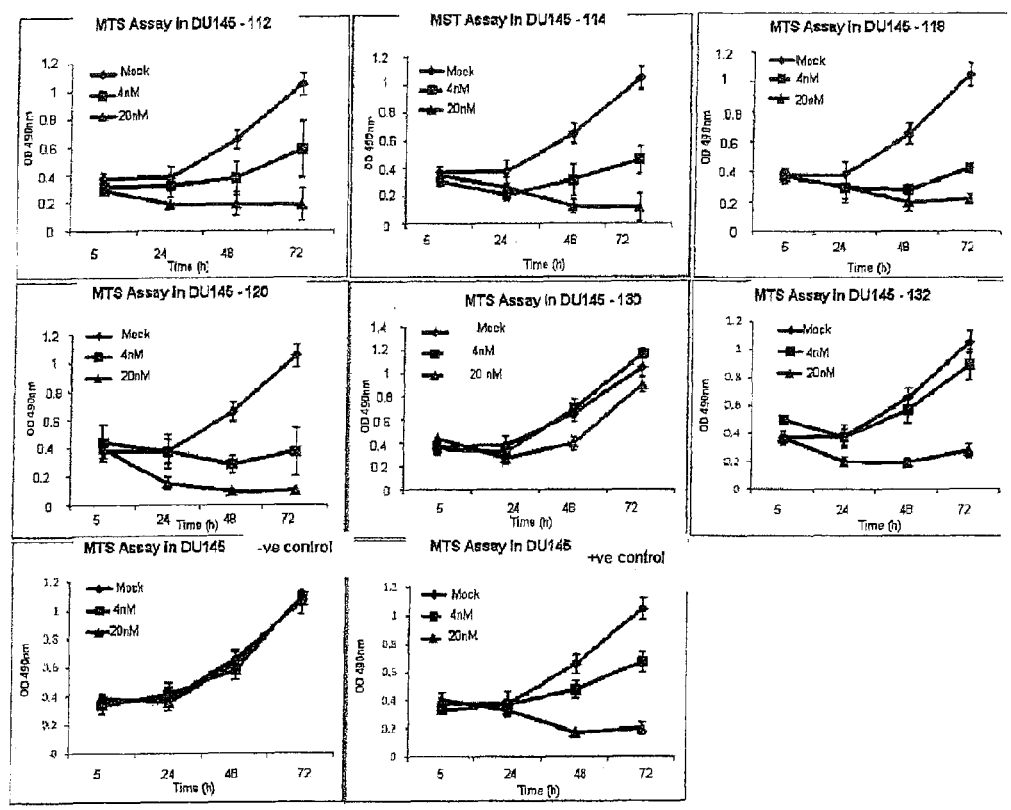
FIG. 11: Proliferation assay in DU-145 cells. The MTS assay was performed in DU-145 cells using 4 nM and 20 nM final oligomer concentrations. The oligomer having the sequence set forth in SEQ ID NO: 133 is a scrambled control which was used as negative control (−ve). The positive control (+ve) is an oligomer which is toxic both in vitro and in vivo—it is therefore used as a positive control in toxicity assays. The SEQ ID No of the oligomer used is indicated on the header of each graph.

Proliferation after transfection with GLI2 oligomers was investigated in DU-145 and 518A2 cells using an MTS assay. Proliferation was analysed at 5 h, 24 h, 48 h and 72 h after transfection. The results showed that all GLI2 oligomers except for the oligomer having the sequence shown as SEQ ID NO: 130 showed potent and dose-dependent inhibition of proliferation in both the DU-145 and 518A2 cells, while the negative control had no effect on cell proliferation. The most potent oligomers at inhibiting proliferation were oligomers having sequences shown as SEQ ID NOs: 114, 118 and 120. Four independent screens were performed, and data from the screen being the best representative of the average activity of the different oligomers is presented (FIG. 11).

Example 17

In Vivo Analysis: ALT and AST Determination in Mouse Liver after In Vivo (i.v.) Administration of Gli Oligonucleotides Female NMRI mice received i.v. injection of oligonucleotides having the sequences shown as SEQ ID NOs: 112, 114, 118, 120 and 132 on day 0, 3, 6 and 9 at a dosage of 10 mg/kg. Animals were sacrificed 24 h after last dosing. ALT and AST levels were determined in the blood serum, free from red blood cells, obtained from the mice at the time of sacrifice. The activity of alanine-aminotransferase (ALT) and aspartate-aminotransferase (AST) in mouse serum was determined using an enzymatic ALT assay (ABX Pentra A11A01627 (ALT) or A11A01629 (AST), Horiba ABX Diagnostics, France) according to the manufacturer's instruction but adjusted to 96-well format. In short, serum samples were diluted 2.5 fold with $H_2O$ and assayed in duplicate. After addition of 50 µl diluted sample or standard (multical from ABX Pentra, A11A01652) to each well, 200 µl of 37° C. ALT reagent mix was added to each well. Kinetic measurements were performed at 340 nm and 37° C. for 5 min with an interval of 30 s. Data were correlated to the 2-fold diluted standard curve and results were presented as ALT activity in U/L.

Figure 12A:
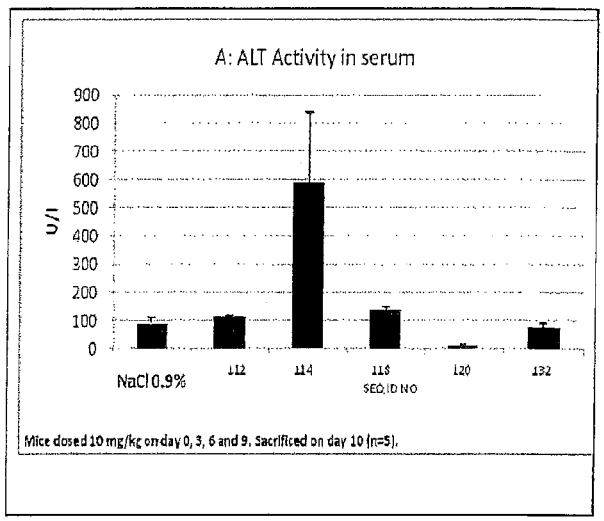
FIGS. 12 A and B: ALT/AST activity in serum. One mouse in the group dosed with an oligomer having the sequence set forth in SEQ ID NO: 120 targeting GLI2 was found dead on day 6, and the remaining animals in this group were in a poor condition and were sacrificed on day 6. ALT activity in the group treated with the oligomer having the sequence set forth in SEQ ID NO: SEQ ID NO: 120 was too high to be measurable. The SEQ ID No of the oligomer used is indicated under each bar of the graph.
Figure 12B:
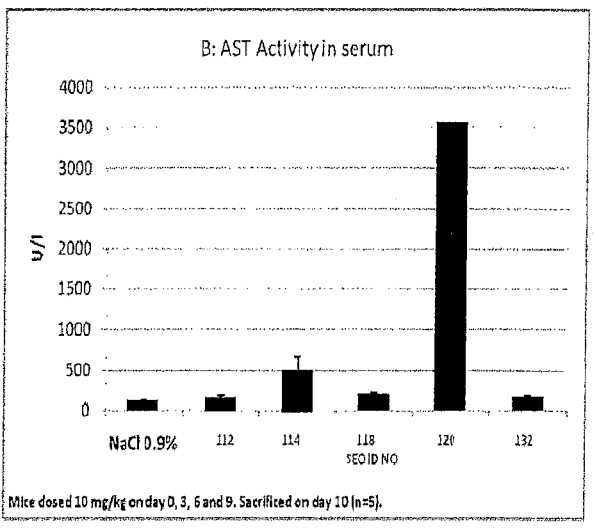

The results are shown in FIGS. 12 A and B.

Example 18

Anti-Tumor Effects of Anti-GLI Oligonucleotides in Animal Models

For all xenograft studies, mice were implanted with tumors subcutaneously. When tumors reached about 100-200 mm³ (or the size indicated), mice were injected with LNA-oligonucleotides at the indicated doses and schedule.

Figure 15A:
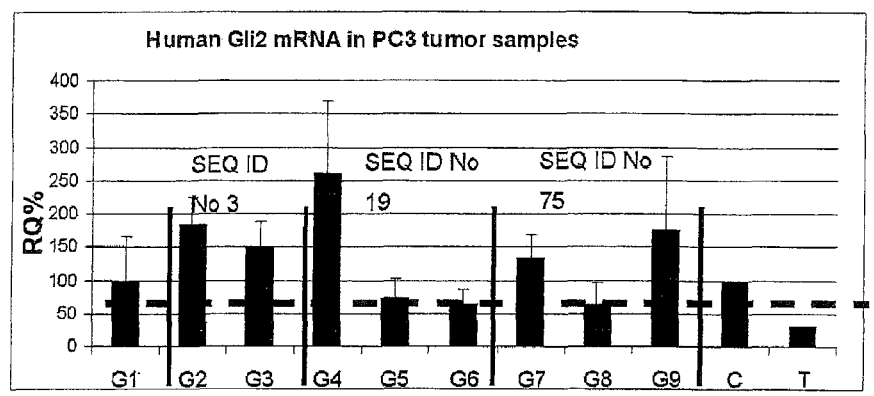

PC3 tumor-bearing mice (a prostate cancer model) were treated with 3, 30, and 100 mg/kg of LNA oligomers having the sequences set forth in SEQ ID NO: 3, SEQ ID NO: 19, or SEQ ID NO: 75 (intravenous (IV); 4 doses every third day (q3dx4)). At the end of the study, tumors were harvested, and human and mouse GLI mRNA and PTCH1 mRNA levels were assayed using probes specific for either human or mouse mRNAs. A positive control (from cells transfected with a GLI2 antisense oligonucleotide—SEQ ID NO: 10) was included in the study, which produced down regulation results as expected. Treatment with oligomers having the sequences set forth in SEQ ID NO: 19, SEQ ID NO: 75 or SEQ ID NO: 3 did not result in knockdown of human GLI1, GLI3 or Ptch1 mRNA (data not shown). However, as shown in FIG. 15a, a degree of down modulation of GLI2 mRNA in tumor epithelial cells was observed upon treatment with oligomers having SEQ ID NO: 19 or SEQ ID NO: 75, although no dose-response relationship could be established.

Interestingly, mouse mRNA of GLI1, GLI2 and Ptch1 were significantly down modulated by all 3 oligomers, although no dose-response relationship could be established (see FIG. 15b—PC3 tumor stroma). Since GLI1 (under the control of GLI2) is a transcription factor directly related to the hedgehog pathway, the results suggest that stromal cells are likely affected by the treatment of antisense oligonucleotides targeted to GLI mRNAs. GLI2 controls the levels of GLI1 and Ptch1. Therefore, inhibition of GLI2 will lead to the down-regulation of GLI1 and Ptch1.

In FIG. 15: G1 refers to saline; G2 refers to 3 mg/kg of SEQ ID No 3; G3 refers to 30 mg/kg of SEQ ID No 3; G4 refers to 3 mg/kg of SEQ ID No 19; G5 refers to 30 mg/kg of SEQ ID No 19; G6 refers to 100 mg/kg of SEQ ID No 19; G7 refers to 3 mg/kg of SEQ ID No 75; G8 refers to 30 mg/kg of SEQ ID No 75; G9 refers to 100 mg/kg of SEQ ID No 75; C refers to the in vitro control 518A—a melanoma cell line; T refers to the in vitro control 10 nM of 4478 (GLi2 antisense (SEQ ID NO 10). The term RQ % refers to percentage relative quantity; the term KD refers to knock down; the term AN09017 refers to the study number used by the experimenter; the term "mpk" refers to mg/kg.

A previous mini-toxicology (minitox) study showed evidence of tumor growth inhibition (TGI) (FIG. 16). In this study, the efficacy of oligomers having the sequences set forth in SEQ ID NO: 3 (data not shown), SEQ ID NO: 19 (see FIG. 16), or SEQ ID NO: 75 (see FIG. 16) were tested at multiple doses (0.3-30 mg/kg; 10 doses every third day (q3dx10)) in a DU-145 prostate cancer model. The compounds failed to show robust TGI, as suggested by the minitoxicology experiments. There was a trend for the 3 mg/kg dose to perform better than other dose levels, at least for the oligomers having the sequences set forth in SEQ ID NO: 19 and SEQ ID NO: 75.

An efficacy study in a PC3 xenograft prostate cancer model was conducted.

Figure 17:
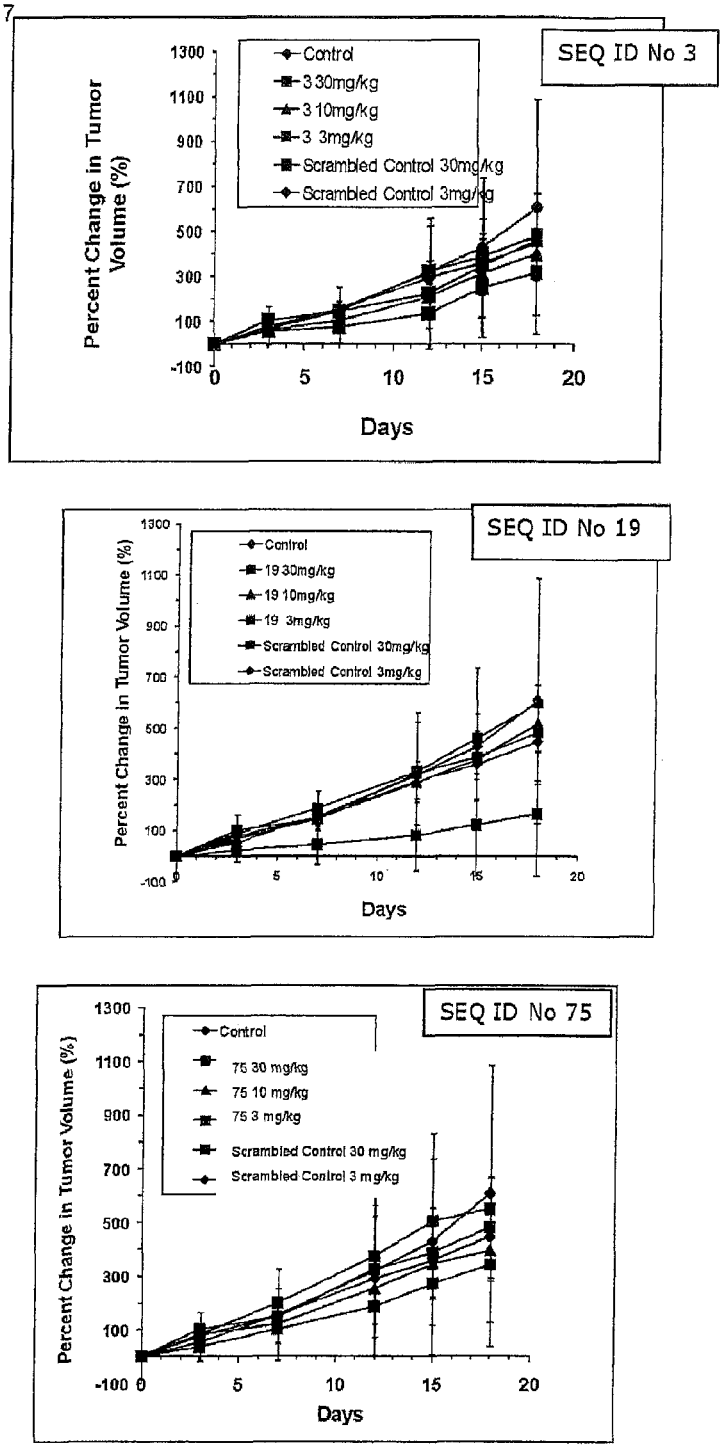
FIG. 17: Efficacy study (tumor growth inhibition) of oligomers having the sequence set forth in SEQ ID NO: 3, SEQ ID NO: 19, or SEQ ID NO: 75 in PC3 prostate cancer model. In the key to the graphs, "3" refers to SEQ ID No 3 (e.g. "3 30 mg/kg" refers to 30 mg/kg of SEQ ID No 3); "Scrambled control" refers to scrambled control oligomer for survivin; "19" refers to SEQ ID No 19 (e.g. "19 30 mg/kg" refers to 30 mg/kg of SEQ ID No 19); and "75" refers to SEQ ID No 75 (e.g. "75 10 mg/kg" refers to 10 mg/kg of SEQ ID No 75).

Oligonucleotides having sequences as shown in SEQ ID NO: 3, SEQ ID NO: 19, or SEQ ID NO: 75 were given q3dx10 (10 doses every third day) at 3-30 mg/kg. As of day 28 (last day with survival near 100% among most groups), the largest TGI of any treatments were seen for treatment with the oligomer having the sequence set forth in SEQ ID NO: 19 (54%) and with the oligomer having the sequence set forth in SEQ ID NO: 3 (34%), both at 3 mg/kg (see FIG. 17). Large variation in response was observed in any particular group. Interestingly, treatment with the oligomer having the sequence set forth in SEQ ID NO: 19 at 3 mg/kg resulted in the best TGI.

Figure 18:
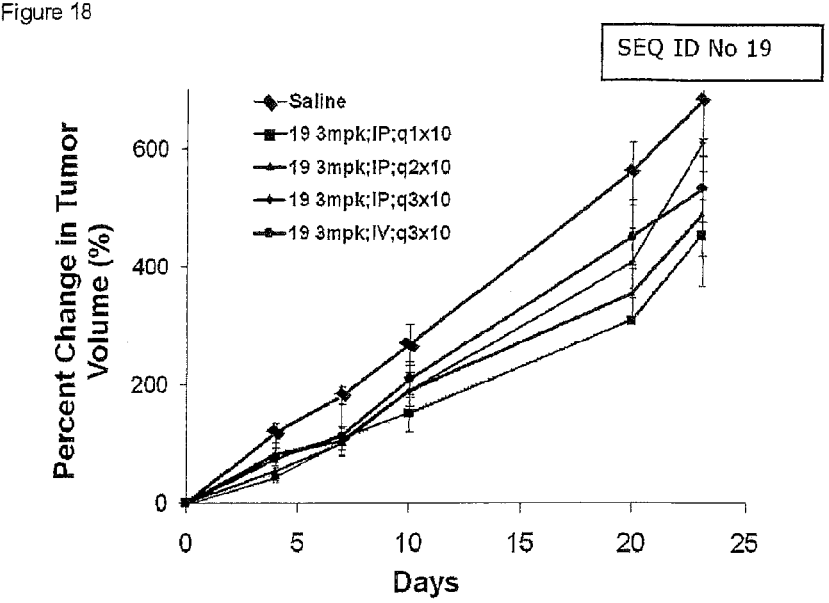
FIG. 18: Efficacy study (tumor growth inhibition) of the oligomer having the sequence set forth in SEQ ID NO: 19 in PC3 prostate cancer model. In the key to the graph, "19" refers to SEQ ID No 19, "mpk" refers to mg/kg, "IP" refers to intraperitoneal administration; "IV" refers to intravenous administration; "q1×10" refers to 10 doses every day; "q2× 10" refers to 10 doses every second day; and "q3×10" refers to 10 doses every third day; e.g. "19 3 mpk;IP;q1×10" refers to 10 doses every day of 3 mg/kg of SEQ ID No 19 by intraperitoneal administration.

In this study, the oligomer having the sequence set forth in SEQ ID NO: 19 was administered (3 mg/kg, IV) in a full efficacy study against PC3 xenografts (a prostate cancer model). The study also compared ip (intraperitoneal) and iv (intravenous) dosing routes. A moderate TGI with best response on q1d (everyday dosing) schedule (29% TGI) was observed (see FIG. 18). Administration of the oligomer via an intravenous or intraperitoneal route (on a q3d schedule—dosing every third day) resulted in similar efficacy. This study indicates that the GLI antisense oligomer may be effective in treating prostate cancer. The term "mpk" on FIG. 18 means "mg/kg".

DLD-1 colorectal cancer model is a cyclopamine-resistant colon cancer model (Yauch et al Nature 2008, 455: 406-410). A mutation in exon 11 of the Smo gene is present in this cancer cell line. Nevertheless, the hedgehog pathway is still activated. The model is not responsive to Smo inhibitors (e.g., cyclopamine) in vitro or in vivo. Further, it has been shown that DLD-1 does not secrete the hedgehog ligand. Because of the absence of ligand and/or Smo mutations, the model is unlikely to respond to cyclopamine or its analogues, and thus is a good model for testing alternative therapies, such as GLI2 antisense therapy. Growth inhibition has been previously demonstrated with an MOE sugar containing-oligonucleotide (Kim et al, 2007 CANCER RES. 67(8) 3583-3593.).

The effect of the oligomer having the sequence set forth in SEQ ID NO: 19 was tested at two dose levels (3 and 30 mg/kg, 6 intravenous doses every third day (q3dx6(iv))) in a DLD-1 colorectal cancer model. Results (top panel of FIG. 19) demonstrate that treatment of animals with 3 mg/kg injected biweekly results in a TGI of 23%. No effect was obtained at the 30 mg/kg dose level. The study was repeated to confirm the TGI results. Encouraged by these preliminary results, an efficacy study was performed in the same model with dosing administered at 3 mg/kg, 10 doses every third day (q3dx10), iv. After the 4$^{th}$ dose, a cohort was sacrificed and tumor and liver samples collected for GLI1/GLI2 mRNA knockdown analysis. Remaining animals were monitored for TGI. In this study, no TGI was observed (bottom panel of FIG. 19). Additional efficacy studies are required.

Figure 20A:
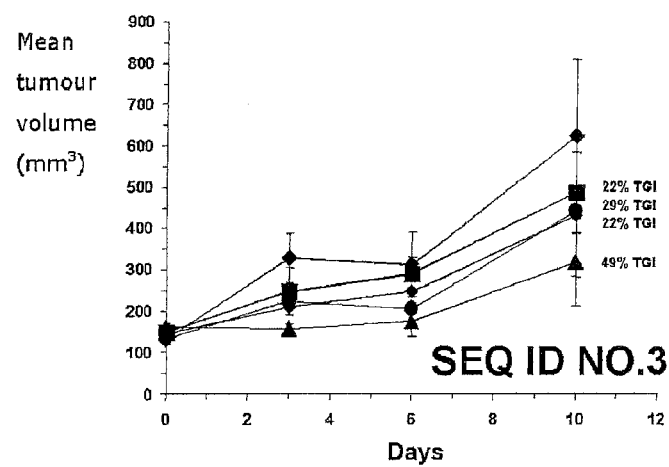
FIGS. 20a, b and c: Efficacy study (tumor growth inhibition) of the oligomer having the sequence set forth in SEQ ID NO: 19 in DU-145 prostate cancer model. In the key to the graphs, "3" refers to SEQ ID No 3, "19" refers to SEQ ID No 19; "75" refers to SEQ ID No 75; "IV" refers to intravenous administration; "q3×4" refers to 4 doses every third day; e.g. "3 3 mg/kg;IV;q3×4" refers to 4 doses every third day of 3 mg/kg of SEQ ID No 3 by intravenous administration.

DU-145 tumor xenografts (a prostate cancer model) were treated with an oligomer having the sequence set forth in SEQ ID NO: 19, SEQ ID NO: 75, or SEQ ID NO: 3 at various doses as indicated. Good antitumor growth inhibition (DU145 model) was observed for all three compounds (FIG. 20 a-c). However, there was a lack of dose response. The most effective dose of SEQ ID NO: 19 and SEQ ID NO: 75 was 3 mg/kg (3 doses every third day (q3dx3)). FIG. 20 refers to q3dx4 (4 doses every third day).

Figure 21:
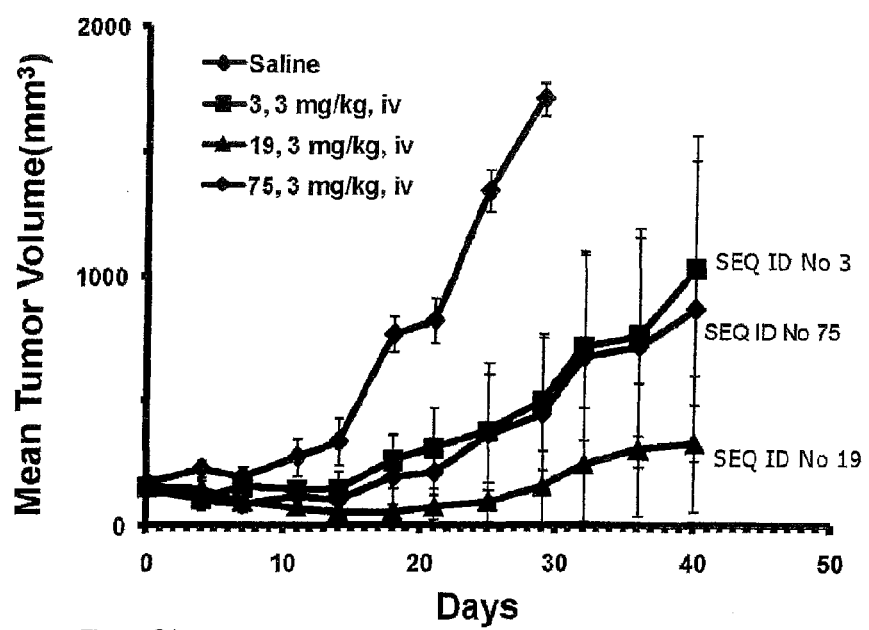
FIG. 21: Tumor growth inhibition (TGI) of oligomers having the sequence set forth in SEQ ID NO: 3, SEQ ID NO: 19, or SEQ ID NO: 75 in PC3 prostate cancer model. In the key to the graphs, "3" refers to SEQ ID No 3, "19" refers to SEQ ID No 19; "75" refers to SEQ ID No 75; "iv" refers to intravenous administration; e.g. "3, 3 mg/kg,iv" refers to 3 mg/kg of SEQ ID No 3 by intravenous administration.

A tumor growth inhibition study was performed with the oligomers having SEQ ID NO: 3, SEQ ID NO: 19, and SEQ ID NO: 75 in the PC3 prostate cancer model (10 doses every third day (q3dx10)) (n.b. n=3). Due to limited quantity of the compounds, each group contained 3 mice. Good to excellent antitumor effects were observed with all three compounds (see FIG. 21), although tumor breakthrough was detected with compounds having the sequences set forth in SEQ ID NO: 3 and SEQ ID NO: 75. Since a high dose of some of these compounds appeared to have no inhibitory effect on tumor growth in the first experiment, tumor-bearing animals were retreated on day 41 with 30 mg/kg of antisense oligomers having the sequences set forth in SEQ ID NO: 19, SEQ ID NO: 3, or SEQ ID NO: 75 to determine if the effect was reproducible. SEQ ID NO: 19 and SEQ ID NO: 75 showed tumor stasis.

Example 19

GLi2 LNA Oligomers Inhibit Human Acute Myeloid Leukemia Cells

Human acute myeloid leukemia (AML) cell lines, especially cytokine-responsive CD34$^+$ cells such as TF-1, Kasumi-1 and -3, were reported to have active hedgehog signaling (Kobune et al. Cancer Sci. 2009, 100:948), suggesting activation of Hh pathway as a contributing factor for the survival and drug resistance of this type of cells. These cell lines were used as models to demonstrate the pathway targeting effect of the following oligomers:

$A_SC_SC_Sa_Sg_Sc_Sa_S{\square}t_Sg_St_Sa_SC_ST_SG$; (SEQ ID NO: 112)

$C_ST_SC_Sc_St_St_Sg_Sg_St_Sg_Sc_Sa_Sg_ST_SC_ST$; (SEQ ID NO: 118)
and $T_SC_SA_Sg_Sa_St_St_Sc_Sa_Sa_Sa_SC_SC_SC_SA$, (SEQ ID NO: 132)

wherein capital letters indicate Beta-D-oxy LNA monomers, lower case letters indicate deoxyribonucleotides, subscript "s" indicates an internucleotide phosphorothioate linkage and all cytosine LNA monomers are 5-methyl cytosine LNA monomers.

(a) The GLi2 LNA oligomers knock down GLi2 mRNA in TF-1 cells. TF-1 cells were plated in 24-well plates approximately 2×10$^5$ cells per well and treated with 1, 0.1, or 0.1 μM of SEQ ID NO: 118 for 24 hours. Lipofectamine 2000 (Invitrogen) at a final dilution of 600-fold was used to facilitate transfection. U937, which is a Hh pathway inactive cell line due to lacking expression of Hh receptor components, were similarly treated as a control. Total RNA was extracted from cells after the treatment and expression of GLi2 mRNA was determined by quantitative RT-PCR. Briefly, 1$^{st}$ strand cDNA was synthesized from 2 μg of total RNA using the High Capacity cDNA Synthesis kit (Invitrogen). The target (GLi2, Hs00259799-ml) and control (GAPDH) gene levels were determined in ABI 7500 Fast Real-time PCR system using the absolute quantification method. SEQ ID NO: 112 and SEQ ID NO: 118 treatment resulted in reduced cellular GLi2 mRNA levels compared to the untreated or the vehicle treated controls (FIG. 22). In U937 cells, the GLi2 mRNA level was too low to be reliably estimated.

(b) The GLi2 LNA oligomers inhibit the growth of TF-1 cells. TF-1 or U937 cells were plated in 24-well plates at a density of approximately 2×10$^3$ cells/ml and treated with 0-4 μM of SEQ ID NO: 118 or SEQ ID NO: 132 without transfection reagent for 6 days. Viable cell population and cell viability were determined in Guava EasyCyte System by using Guava ViaCount reagent. As shown in FIG. 23, without transfection reagent, treatment with SEQ ID NO: 118 and SEQ ID NO: 132 resulted in a concentration-dependent inhibition of cell growth in TF-1 cell. The effect appears to be cell line specific because similar treatment did not affect U937 cell growth (FIG. 24). It should be noted that the cyclopamine, a known Hh pathway inhibitor, did not affect TF-1 cell growth in this study.

(c) Down-regulation of GLI2 protein level by GLi2 LNA oligomers in TF-1 cells. TF-1 cells were treated with 10 or 100 nM of SEQ ID NO: 118 and SEQ ID NO: 132 in the presence of Lipofectamine 2000, a similar treatment as in (a). After 24 hour incubation, cell lysates were prepared and analyzed with SDS-PAGE and Western blotting. As shown in FIG. 25, treatment with SEQ ID NO: 118 resulted in concentration-dependent reduction of GLI2 protein level in TF-1 cells. In this study, the GLI2 protein level in SEQ ID NO: 132-treated cells was not significantly different from the untreated controls, probably due to the short treatment time. Consistent with the mRNA level determination, U937 cell has low GLI2 expression level comparing to TF-1 cell.

(d) Modulation of Hh, FGF, and Wnt pathway components by SEQ ID NOS: 118 and 132 in TF-1 cells. To elucidate the targeted effects of SEQ ID NO: 118 and SEQ ID NO: 132, RT$^2$ Profiler PCR Array Human Hedgehog Signaling Pathway (PAHS-087A, SABiosciences) was used to profile changes of gene expression in TF-1 cells treated similarly as in (a) and (c). Expression of selected gene targets was confirmed by quantitative RT-PCR and is shown in FIG. 26. Consistent with the results in FIG. 22, SEQ ID NO: 118 and SEQ ID NO: 132 treatments resulted in approximately 50% reduction of Gli2 mRNA level in TF-1 cells. Although there were no consistent changes in some known GLI2-targeted gene levels, such as Gli1, Ptch1, and Wnt2B, significant changes were observed in Hh, FGF, and Wnt pathway components. For example, FGF9 mRNA levels were increased more than 6-fold in SEQ ID NO: 118 or SEQ ID NO: 132 treated cells, while Wnt5B expression was reduced 40-50% in the treated cells. These results suggest that expression of FGF9 and Wnt5 might be transcriptionally regulated by GLI2.

(e) To confirm that knockdown of Gli2 by Gli2 LNA oligomers regulates FGF9 and Wnt5B, expression levels of Fgf9 and Wnt5B mRNA in TF-1 and 0937 treated similarly as in (a) were determined by quantitative RT-PCR. The results in FIG. 27 confirmed up- and down-regulation of Fgf9 and Wnt5B, respectively, by SEQ ID NO: 112 and SEQ ID NO: 118 in concentration-dependent fashion. In addition, as shown in FIG. 28, because U937 cell has a much lower Gli2 expression comparing to TF-1, the Gli2 LNA oligomer treatment did not affect expression levels of Fgf9 and Wnt5B. These results support that the changes in Fgf9 and Wnt5B in TF-1 are targeted effects of the Gli2 LNA oligomers.

All publications mentioned in the above specification are incorporated by reference herein. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

The invention claimed is:

1. A method for treating acute myeloid leukaemia or pre-leukaemia, comprising administering to a patient an oligomer consisting of 10-30 nucleobases wherein the oligomer is perfectly complementary to a corresponding region of SEQ ID NO:1, all linkages between nucleobases are phosphorothioate linkages, and comprises nucleotide analogues having a modified sugar.

2. The method of claim 1 wherein the oligomer is not perfectly complementary along its entire length to any portion of SEQ ID NO:2.

3. The method of claim 1 wherein the oligomer comprises the sequence of SEQ ID NO:19.

4. The method of claim 1 wherein the is between 10-18 nucleobases in length.

5. The method of claim 1 wherein the nucleotide analogues having a modified sugar are selected from the group consisting of: Locked Nucleic Acid (LNA); 2'-O-alkyl-RNA, 2'-OMe-RNA, 2'-amino-DNA, and 2'-fluoro-DNA.

6. The method of claim 5 wherein the nucleotide analogues are LNA.

7. The method of claim 1 wherein the oligomer is a gapmer.

8. The method of claim 1 wherein the oligomer inhibits the expression of GL12 or GL12 mRNA in a cell which is expressing GL12 or GL12 mRNA.

9. The method of claim 1 wherein the oligomer comprises at least one non-nucleotide or non-polynucleotide moiety.

10. The method of claim 1 wherein the preleukemia is myelodysplastic syndrome or myeloproliferative disease.

11. The method of claim 1 wherein the oligomer comprises SEQ ID NOs: 112, 114, 118, 120, or 132.

12. The method of claim 1 wherein the oligomer is between 12-18 nucleobases in length.

13. The method of claim 1 wherein the oligomer is between 12-16 nucleobases in length.

* * * * *

```
                        SEQUENCE LISTING

<160> NUMBER OF SEQ ID NOS: 134

<210> SEQ ID NO 1
<211> LENGTH: 6780
<212> TYPE: DNA
<213> ORGANISM: Homo sapiens

<400> SEQUENCE: 1
gattgccacc caggacgatg agcggctgag atggagacgt ctgcctcagc cactgcctcc      60
gagaagcaag aagccaaaag tgggatcctg gaggccgctg gcttccccga cccgggtaaa     120
aaggcctctc ctttggtggt ggctgcagcg gcagcagcag cggtagctgc ccaaggagtg     180
ccgcagcatc tcttgccacc attccatgcg cccctaccga ttgacatgcg acaccaggaa     240
ggaaggtacc attacgagcc tcattctgtc cacggtgtgc acgggccccc tgccctcagc     300
ggcagccctg tcatctctga catctccttg atccggcttt ccccgcaccc ggctggccct     360
ggggagtccc ccttcaacgc cccccacccg tacgtgaacc cccacatgga gcactacctc     420
cgttctgtgc acagcagccc cacgctctcc atgatctctg cagccagggg cctcagcccc     480
gctgatgtgg cccaggagca ccttaaggag aggggactgt ttggccttcc tgctccaggc     540
accaccccct cagactatta ccaccagatg accctcgtgg caggccaccc cgcgccctac     600
ggggacctgc tgatgcagag cggggcgct gccagcgcac cccatctcca cgactacctc     660 aacccgtgg acgtgtcccg tttctccagc ccgcgggtga cgccccgcct gagccgcaag     720
cgggcgctgt ccatctcccc actctcagac gccagcctgg acctgcagcg gatgatccgc     780
acctcaccca actcgctagt ggcctacatc aacaactccc gaagcagctc ggcggccagc     840
ggttcctacg ggcatctgtc agcgggtgcc ctcagcccag ccttcacctt ccccaccccc     900
atcaaccccg tggcctacca gcagattctg agccagcaga ggggtctggg gtcagccttt     960
ggacacacac caccctgat ccagccctca cccaccttcc tggcccagca gccatggcc    1020 ctcacctcca tcaatgccac gcccaccag ctcagcagca gcagcaactg tctgagtgac    1080
accaaccaga acaagcagag cagtgagtcg gccgtcagca gcaccgtcaa ccctgtcgcc    1140
```

-continued

```
attcacaagc gcagcaaggt caagaccgag cctgagggcc tgcggccggc ctcccctctg    1200
gcgctgacgc agggccaggt gtctggacac ggctcatgtg ggtgtgccct tcccctctcc    1260
caggagcagc tggctgacct caaggaagat ctggacaggg atgactgtaa gcaggaggct    1320
gaggtggtca tctatgagac caactgccac tgggaagact gcaccaagga gtacgacacc    1380
caggagcagc tggtgcatca catcaacaac gagcacatcc acggggagaa gaaggagttt    1440
gtgtgccgct gcaggcctg cacgcgggag cagaagccct tcaaggcgca gtacatgctg    1500
gtggtgcaca tgcggcgaca cacgggcgag aagccccaca agtgcacgtt cgagggctgc    1560
tcgaaggcct actcccgcct ggagaacctg aagacacacc tgcggtccca caccggggag    1620
aagccatatg tgtgtgagca cgagggctgc aacaaagcct tctccaacgc ctcggaccgc    1680
gccaagcacc agaatcgcac ccactccaac gagaaaccct acatctgcaa gatcccaggc    1740
tgcaccaaga gatacacaga ccccagctct ctccggaagc atgtgaaaac ggtccacggc    1800
ccagatgccc acgtcaccaa gaagcagcgc aatgacgtgc acctccgcac accgctgctc    1860
aaagagaatg gggacagtga ggccggcacg gagcctggcg gcccagagag caccgaggcc    1920
agcagcacca gccaggccgt ggaggactgc ctgcacgtca gagccatcaa gaccgagagc    1980
tccgggctgt gtcagtccag ccccggggcc cagtcgtcct gcagcagcga gccctctcct    2040
ctgggcagtg cccccaacaa tgacagtggc gtggagatgc cggggacggg gcccgggagc    2100
ctgggagacc tgacggcact ggatgacaca ccccagggg ccgacacctc agccctggct    2160
gcccctccg ctggtggcct ccagctgcgc aaacacatga ccaccatgca ccggttcgag    2220
cagctcaaga aggagaagct caagtcactc aaggattcct gctcatgggc cgggccgact    2280
ccacacacgc ggaacaccaa gctgcctccc ctcccgggaa gtggctccat cctggaaaac    2340
ttcagtggca gtggggcgg cgggcccgcg gggctgctgc cgaacccgcg gctgtcggag    2400
ctgtccgcga gcgaggtgac catgctgagc cagctgcagg agcgccgcga cagctccacc    2460
agcacggtca gctcggccta caccgtgagc cgccgctcct ccggcatctc ccctacttc    2520
tccagccgcc gctccagcga ggcctcgccc ctgggcgccg gccgcccgca caacgcgagc    2580
tccgctgact cctacgaccc catctccacg gacgcgtcgc ggcgctcgag cgaggccagc    2640
cagtgcagcg gcggctccgg gctgctcaac ctcacgccgg cgcagcagta cagcctgcgg    2700
gccaagtacg cggcagccac tggcggcccc ccgcccactc cgctgccggg cctggagcgc    2760
atgagcctgc ggaccaggct ggcgctgctg gacgcgcccg agcgcacgct gcccgccggc    2820
tgcccacgcc cactggggcc gcggcgtggc agcgacgggc cgacctatgg ccacggccac    2880
gcggggctg cgcccgcctt ccccacgag gctccaggcg gcggagccag gcgggccagc    2940
gaccctgtgc ggcggcccga tgccctgtcc ctgccgcggg tgcagcgctt ccacagcacc    3000
cacaacgtga accccggccc gctgccgccc tgtgccgaca ggcgaggcct ccgcctgcag    3060
agccacccga gcaccgacgg cggcctgcc cgcggcgcct actcgccccg gccgcctagc    3120
atcagcgaga acgtggcgat ggaggccgtg gcggcaggag tggacggcgc ggggcccgag    3180
gccgacctgg ggctgccgga ggacgacctg gtgcttccag acgacgtggt gcagtacatc    3240
aaggcgcacg ccagtggcgc tctggacgag ggcaccgggc aggtgtatcc cacggaaagc    3300
actggcttct ctgacaaccc cagactaccc agcccggggc tgcacggcca gcgcaggatg    3360
gtggctgcgg actccaacgt gggccctcc gcccctatgc tgggaggatg ccagttaggc    3420
tttgggcgc cctccagcct gaacaaaaat aacatgcctg tgcagtggaa tgaggtgagc    3480
```

-continued

```
tccggcaccg tagacgccct ggccagccag gtgaagcctc acccttttcc tcagggcaac    3540
ctggcggtgg tgcagcagaa gcctgccttt ggccagtacc cgggctacag tccgcaaggc    3600
ctacaggcta gccctggggg cctggacagc acgcagccac acctgcagcc ccgcagcgga    3660
gcccctccc agggcatccc cagggtaaac tacatgcagc agctgcgaca gccagtggca    3720
ggcagccagt gtcctggcat gactaccact atgagccccc atgcctgcta tggccaagtc    3780
caccccagc tgagcccag caccatcagt ggggccctca accagttccc caatcctgc      3840
agcaacatgc cagccaagcc agggcatctg gggcacctc agcagacaga gtggcacct    3900
gaccccacca cgatgggcaa tcgccacagg gaacttgggg tccccgattc agccctggct    3960
ggagtgccac cacctcaccc agtccagagc taccacagc agagccatca cctggcagcc    4020
tccatgagcc aggagggcta ccaccaggtc cccagccttc tgcctgcccg ccagcctggc    4080
ttcatggagc cccaaacagg cccgatgggg gtggctacag caggctttgg cctagtgcag    4140
ccccggcctc ccctcgagcc cagcccact ggccgccacc gtggggtacg tgctgtgcag    4200
cagcagctgg cctacgccag gccacaggc catgccatgg ctgccatgcc gtccagtcag    4260
gaaacagcag aggctgtgcc caagggagcg atgggcaaca tggggtcggt gcctccccag    4320
ccgcctccgc aggacgcagg tggggcccg gaccacagca tgctctacta ctacggccag    4380
atccacatgt acgaacagga tggaggcctg gagaacctcg ggagctgcca ggtcatgcgg    4440
tcccagccac cacagccaca ggcctgtcag gacagcatcc agccccagcc cttgccctca    4500
ccaggggtca accaggtgtc cagcactgtg gactcccagc tcctggaggc ccccagatt    4560
gacttcgatg ccatcatgga tgatggcgat cactcgagtt tgttctcggg tgctctgagc    4620
cccagcctcc tccacagcct ctcccagaac tcctcccgcc tcaccacccc ccgaaactcc    4680
ttgaccctgc cctccatccc cgcaggcatc agcaacatgg ctgtcgggga catgagctcc    4740
atgctcacca gcctcgccga ggagagcaag ttcctgaaca tgatgaccta gaggcccgag    4800
cgcctggtgc tgagtgcacc cggaggggtc atcgctgccc agagcctggg gattccagct    4860
gtcttgtctt tttccaaaaa agtgttaaat aggcttgagg ggttgttgcg caatggccgc    4920
tcagatgac agatgttgta agagaaggtt tatgggcatc ctctctggtc ttttggatta    4980
ttcctcagaa caatgaaaaa agtctccata ggacaggaag gaatgcaaaa ctcatttaca    5040
cagtgctttc cagcctttgg tgcttacagg accgcgctgt tccggcttct tcacggctga    5100
cattcggcta acgagggatt actttggcca aaaccttca aaggatatgc agaaagatgg    5160
tagggagcat ttgggtttga atctgaatgc tatactggat actctgctcc ggaaagatga    5220
gcttttatt ctactacttg gaaggaaaag gaattcctgg tccacctgaa ttcctctatg    5280
aagcctaact cttgaggtct ctaacatacc ttgtcataga ggaaaagcac agattatacc    5340
tggatgattc aggagcacat tctgattcca ggtttggtag agctggctct tctactccgt    5400
aaagccgagt ctgggactgg cagcccatcc aagtgtatat gaatgaataa agcatccaag    5460
tatatatgaa tgaataaagt atgtaagtat caccagaaaa aggaaagaaa aaatgtactc    5520
cttggggcaa gcccagaagc tgccctggcc tctccagacc gtgtttacag tgtttgcatg    5580
tagaatgtag cccttcctga aaagaagact tgtttctaaa tacctcgggg ctgctggagc    5640
cgctgtgggt tagggatgga ctgaggcctc gaggagtgag ggtgcacccg ggcccagcc    5700
tcaggctgcc ctaggatct ctcagtagga agaggaagtt gcgtgtttac ccaatcctgt    5760
ttctccaatg caacgtccac ccactttacc accaaaaact ccaggccctg acggcagccc    5820
ggtccccag cactcaccag cagcccagtg ttctccacca agccacagtg tgcatgcctg    5880
```

| | | | | |
|---|---|---|---|---|
| gtatcctccg | gattcccttc | cttctgcccg | ctgagtcact | gggcagagaa tgatgacatg | 5940 |
| tgtaggtggt | gtggttgggg | gtggaaaggg | gaagggttg | atcctcagga ctctgaggga | 6000 |
| gcatcgttga | attttcctgt | tcagtgtgac | caagacccac | ctggaaatgg aatttggaac | 6060 |
| tggcttcagg | agacatcatt | cctgaacaca | ctgtagggtg | aattggtgca tcttccccac | 6120 |
| catacacaca | cacacacaca | cacacacaca | cacacacaca | cacacacccc aaaccttttc | 6180 |
| atggggaatg | tgtggcaacc | ttgccaaaca | gcaccactca | gagtgtgact ctgactgtga | 6240 |
| ccttggcctt | aatgaggaac | ttcttaggag | agtttgagga | caaggccaac atcgtcatct | 6300 |
| gggctcgctg | cgtcccagca | catcaaactc | tgtccagaga | caaggccaac tgcaaatgaa | 6360 |
| agccagggaa | cattgctaag | ggtctgtggc | tctgtggtgg | tgttcatcgc cttcctgaga | 6420 |
| taggatttcc | cttgccagtc | ccaacctgta | tatattctgt | acagaagaca tccctgaata | 6480 |
| tactgtaggt | gagtcgtcca | gccaaattta | tatctccaaa | acattttag cttttctac | 6540 |
| atgctatgaa | ttgagatgac | atgctcaact | tgtaaataag | tcttttgta cattaaaaaa | 6600 |
| gtaattttt | cataatttat | cttgtctatc | tgcttccccc | ttgacagtag ttaatgagaa | 6660 |
| cctgggcagt | aaatttggtg | cattcgagca | gaaattaggc | tgtattttt cttaacagtg | 6720 |
| tcaaaattga | ctatcccgcc | tttgccaaga | aatgtttaat | gctgaggcaa aaaaaaaaa | 6780 |

<210> SEQ ID NO 2
<211> LENGTH: 3600
<212> TYPE: DNA
<213> ORGANISM: Homo sapiens

<400> SEQUENCE: 2

| | | | | |
|---|---|---|---|---|
| cccagactcc | agccctggac | cgcgcatccc | gagcccagcg | cccagacaga gtgtccccac | 60 |
| accctcctct | gagacgccat | gttcaactcg | atgaccccac | caccaatcag tagctatggc | 120 |
| gagccctgct | gtctccggcc | cctccccagt | caggggggccc | ccagtgtggg gacagaagga | 180 |
| ctgtctggcc | cgcccttctg | ccaccaagct | aacctcatgt | ccggccccca cagttatggg | 240 |
| ccagccagag | agaccaacag | ctgcaccgag | ggcccactct | tttcttctcc ccggagtgca | 300 |
| gtcaagttga | ccaagaagcg | ggcactgtcc | atctccacct | tgtcggatgc cagcctggac | 360 |
| ctgcagacgg | ttatccgcac | ctcacccagc | tccctcgtag | ctttcatcaa ctcgcgatgc | 420 |
| acatctccag | gaggctccta | cggtcatctc | tccattggca | ccatgagccc atctctggga | 480 |
| ttcccagccc | agatgaatca | ccaaaaaggg | ccctcgcctt | cctttggggt ccagccttgt | 540 |
| ggtcccccatg | actctgcccg | gggtgggatg | atcccacatc | ctcagtcccg ggacccttc | 600 |
| ccaacttgcc | agctgaagtc | tgagctggac | atgctggttg | gcaagtgccg ggaggaaccc | 660 |
| ttggaaggtg | atatgtccag | ccccaactcc | acaggcatac | aggatcccct gttgggatg | 720 |
| ctggatgggc | gggaggacct | cgagagagag | gagaagcgtg | agcctgaatc tgtgtatgaa | 780 |
| actgactgcc | gttgggatgg | ctgcagccag | gaatttgact | cccaagagca gctggtgcac | 840 |
| cacatcaaca | gcgagcacat | ccacggggag | cggaaggagt | tcgtgtgcca ctgggggggc | 900 |
| tgctccaggg | agctgaggcc | cttcaaagcc | cagtacatgc | tggtggttca catgcgcaga | 960 |
| cacactggcg | agaagccaca | caagtgcacg | tttgaagggt | gccggaagtc atactcacgc | 1020 |
| ctcgaaaacc | tgaagacgca | cctgcggtca | cacacgggtg | agaagccata catgtgtgag | 1080 |
| cacgagggct | gcagtaaagc | cttcagcaat | gccagtgacc | gagccaagca ccagaatcgg | 1140 |
| acccattcca | atgagaagcc | gtatgtatgt | aagctccctg | gctgcaccaa acgctataca | 1200 |

```
gatcctagct cgctgcgaaa acatgtcaag acagtgcatg gtcctgacgc ccatgtgacc    1260
aaacggcacc gtggggatgg cccctgcct cgggcaccat ccatttctac agtggagccc    1320
aagagggagc gggaaggagg tcccatcagg gaggaaagca gactgactgt gccagagggt    1380
gccatgaagc cacagccaag ccctgggcc cagtcatcct gcagcagtga ccactccccg    1440
gcagggagtg cagccaatac agacagtggt gtggaaatga ctggcaatgc aggggcagc    1500 actgaagacc tctccagctt ggacgaggga ccttgcattg ctggcactgg tctgtccact    1560
cttcgccgcc ttgagaacct caggctggac cagctacatc aactccggcc aatagggacc    1620
cggggtctca aactgcccag cttgtcccac accggtacca ctgtgtcccg ccgcgtgggc    1680 ccccagtct ctcttgaacg ccgcagcagc agctccagca gcatcagctc tgcctatact    1740
gtcagccgcc gctcctccct ggcctctcct ttcccctg gctccccacc agagaatgga    1800
gcatcctccc tgcctggcct tatgcctgcc cagcactacc tgcttcgggc aagatatgct    1860
tcagccagag ggggtggtac ttcgcccact gcagcatcca gcctggatcg gataggtggt    1920
cttcccatgc ctccttggag aagccgagcc gagtatccag gatacaaccc caatgcaggg    1980 gtcaccccgga gggccagtga cccagcccag gctgctgacc gtcctgctcc agctagagtc    2040
cagaggttca gagcctggg ctgtgtccat acccccaccca ctgtggcagg gggaggacag    2100
aactttgatc cttacctccc aacctctgtc tactcaccac agccccccag catcactgag    2160
aatgctgcca tggatgctag agggctacag gaagagccaa aagttgggac ctccatggtg    2220
ggcagtggtc tgaaccccta tatggacttc ccacctactg atactctggg atatggggga    2280
cctgaagggg cagcagctga gccttatgga gcgaggggtc caggctctct gcctcttggg    2340
cctggtccac ccaccaacta tggccccaac ccctgtcccc agcaggcctc atatcctgac    2400
cccacccaag aaacatgggg tgagttccct tccacactctg gctgtaccc aggcccaag    2460 gctctaggtg aacctacag ccagtgtcct cgacttgaac attatggaca agtgcaagtc    2520
aagccagaac aggggtgccc agtgggggtct gactccacag gactggcacc ctgcctcaat    2580
gcccacccca gtgaggggcc cccacatcca cagcctctct tttcccatta ccccagccc    2640 tctcctcccc aatatctcca gtcaggcccc tatacccagc cacccctga ttatcttcct    2700 tcagaaccca ggccttgcct ggactttgat tcccccaccc attccacagg gcagctcaag    2760
gctcagcttg tgtgtaatta tgttcaatct caacaggagc tactgtggga gggtggggc    2820 agggaagatg ccccgccca ggaaccttcc taccagagtc ccaagtttct gggggggttcc    2880 caggttagcc caagccgtgc taaagctcca gtgaacacat atggacctgg ctttggaccc    2940
aacttgccca atcacaagtc aggttcctat cccacccctt caccatgcca tgaaaatttt    3000
gtagtggggg caaatagggc ttcacatagg gcagcagcac cacctcgact tctgcccca    3060 ttgcccactt gctatgggcc tctcaaagtg ggaggcacaa accccagctg tggtcatcct    3120
gaggtgggca ggctaggagg gggtcctgcc ttgtaccctc ctcccgaagg acaggtatgt    3180 aacccctgg actctcttga tcttgacaac actcagctgg actttgtggc tattctggat    3240
gagccccagg ggctgagtcc tcctccttcc catgatcagc ggggcagctc tggacatacc    3300
ccacctccct ctgggccccc caacatggct gtgggcaaca tgagtgtctt actgagatcc    3360
ctacctgggg aaacagaatt cctcaactct agtgcctaaa gagtagggaa tctcatccat    3420
cacagatcgc atttcctaag gggttttctat ccttccagaa aaattggggg agctgcagtc    3480
ccctgcacaa gatgccccag ggatgggagg tatgggctgg gggctatgta tagtctgtat    3540
acgttttgag gagaaatttg ataatgacac tgtttcctga taataaagga actgcatcag    3600
```

```
<210> SEQ ID NO 3
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 3
accagcatgt actg                                                      14

<210> SEQ ID NO 4
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 4
accagcatgt act                                                       13

<210> SEQ ID NO 5
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 5
ccagcatgta ctg                                                       13

<210> SEQ ID NO 6
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 6
accagcatgt ac                                                        12

<210> SEQ ID NO 7
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 7
ccagcatgta ct                                                        12

<210> SEQ ID NO 8
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 8
cagcatgtac tg                                                        12
```

<210> SEQ ID NO 9
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 9
aacgtgcact tgtg                                                       14

<210> SEQ ID NO 10
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 10
ttctggtgct tggc                                                       14

<210> SEQ ID NO 11
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 11
ttctggtgct tgg                                                        13

<210> SEQ ID NO 12
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 12
tctggtgctt ggc                                                        13

<210> SEQ ID NO 13
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 13
ttctggtgct tg                                                         12

<210> SEQ ID NO 14
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 14
tctggtgctt gg                                                         12

```
<210> SEQ ID NO 15
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 15
ctggtgcttg gc                                                            12

<210> SEQ ID NO 16
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 16
gtgaaggctg ggctga                                                        16

<210> SEQ ID NO 17
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 17
tctgcttgtt ctggtt                                                        16

<210> SEQ ID NO 18
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 18
cctgcttaca gtcatc                                                        16

<210> SEQ ID NO 19
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 19
ctccttggtg cagtct                                                        16

<210> SEQ ID NO 20
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 20
ctccttggtg cagtc                                                         15

<210> SEQ ID NO 21
```

```
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 21
tccttggtgc agtct                                                          15

<210> SEQ ID NO 22
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 22
ctccttggtg cagt                                                           14

<210> SEQ ID NO 23
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 23
tccttggtgc agtc                                                           14

<210> SEQ ID NO 24
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 24
ccttggtgca gtct                                                           14

<210> SEQ ID NO 25
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 25
ctccttggtg cag                                                            13

<210> SEQ ID NO 26
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 26
tccttggtgc agt                                                            13

<210> SEQ ID NO 27
<211> LENGTH: 13
```

```
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 27
ccttggtgca gtc                                                          13

<210> SEQ ID NO 28
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 28
cttggtgcag tct                                                          13

<210> SEQ ID NO 29
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 29
ctccttggtg ca                                                           12

<210> SEQ ID NO 30
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 30
tccttggtgc ag                                                           12

<210> SEQ ID NO 31
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 31
ccttggtgca gt                                                           12

<210> SEQ ID NO 32
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 32
cttggtgcag tc                                                           12

<210> SEQ ID NO 33
<211> LENGTH: 12
<212> TYPE: DNA
```

<213> ORGANISM: Artificial sequence
<220> FEATURE:
<223> OTHER INFORMATION: Oligomer sequence motif - sequence of monomers
      (nucleotides)

<400> SEQUENCE: 33
ttggtgcagt ct                                                          12

<210> SEQ ID NO 34
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 34
gtgtgtcttc aggttc                                                      16

<210> SEQ ID NO 35
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 35
cgcaggtgtg tcttca                                                      16

<210> SEQ ID NO 36
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 36
cgcaggtgtg tcttc                                                       15

<210> SEQ ID NO 37
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 37
gcaggtgtgt cttca                                                       15

<210> SEQ ID NO 38
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 38
cgcaggtgtg tctt                                                        14

<210> SEQ ID NO 39
<211> LENGTH: 14
<212> TYPE: DNA
<213> ORGANISM: Artificial sequence

```
<220> FEATURE:
<223> OTHER INFORMATION: Oligomer sequence motif - sequence of monomers
      (nucleotides)

<400> SEQUENCE: 39
gcaggtgtgt cttc                                                        14

<210> SEQ ID NO 40
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 40
caggtgtgtc ttca                                                        14

<210> SEQ ID NO 41
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 41
cgcaggtgtg tct                                                         13

<210> SEQ ID NO 42
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 42
gcaggtgtgt ctt                                                         13

<210> SEQ ID NO 43
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 43
caggtgtgtc ttc                                                         13

<210> SEQ ID NO 44
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 44
aggtgtgtct tca                                                         13

<210> SEQ ID NO 45
<211> LENGTH: 12
<212> TYPE: DNA
<213> ORGANISM: Artificial sequence
<220> FEATURE:
```

<223> OTHER INFORMATION: Oligomer sequence motif - sequence of monomers
      (nucleotides)

<400> SEQUENCE: 45
cgcaggtgtg tc                                                         12

<210> SEQ ID NO 46
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 46
gcaggtgtgt ct                                                         12

<210> SEQ ID NO 47
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 47
caggtgtgtc tt                                                         12

<210> SEQ ID NO 48
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 48
aggtgtgtct tc                                                         12

<210> SEQ ID NO 49
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 49
ggtgtgtctt ca                                                         12

<210> SEQ ID NO 50
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 50
gcagatgtag ggtttc                                                     16

<210> SEQ ID NO 51
<211> LENGTH: 16
<212> TYPE: DNA
<213> ORGANISM: Artificial sequence
<220> FEATURE:
<223> OTHER INFORMATION: Oligomer sequence motif - sequence of monomers

```
                                   (nucleotides)

<400> SEQUENCE: 51
gccactgtca ttgttg                                                        16

<210> SEQ ID NO 52
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 52
ccagggctga ggtgtc                                                        16

<210> SEQ ID NO 53
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 53
gaggcagctt ggtgtt                                                        16

<210> SEQ ID NO 54
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 54
tgctggtgga gctgtc                                                        16

<210> SEQ ID NO 55
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 55
gtgaggttga gcagcc                                                        16

<210> SEQ ID NO 56
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 56
gccgcacagg gtcgct                                                        16

<210> SEQ ID NO 57
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)
```

```
<400> SEQUENCE: 57
atgtagttta ccctgg                                                    16

<210> SEQ ID NO 58
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 58
ccatgaagcc aggctg                                                    16

<210> SEQ ID NO 59
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 59
tacatgtgga tctggc                                                    16

<210> SEQ ID NO 60
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 60
tacatgtgga tctgg                                                     15

<210> SEQ ID NO 61
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 61
acatgtggat ctggc                                                     15

<210> SEQ ID NO 62
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 62
tacatgtgga tctg                                                      14

<210> SEQ ID NO 63
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)
```

```
<400> SEQUENCE: 63
acatgtggat ctgg                                                        14

<210> SEQ ID NO 64
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 64
catgtggatc tggc                                                        14

<210> SEQ ID NO 65
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 65
tacatgtgga tct                                                         13

<210> SEQ ID NO 66
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 66
acatgtggat ctg                                                         13

<210> SEQ ID NO 67
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 67
catgtggatc tgg                                                         13

<210> SEQ ID NO 68
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 68
atgtggatct ggc                                                         13

<210> SEQ ID NO 69
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 69
```
tacatgtgga tc                                                          12

<210> SEQ ID NO 70
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 70
acatgtggat ct                                                          12

<210> SEQ ID NO 71
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 71
catgtggatc tg                                                          12

<210> SEQ ID NO 72
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 72
atgtggatct gg                                                          12

<210> SEQ ID NO 73
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 73
tgtggatctg gc                                                          12

<210> SEQ ID NO 74
<211> LENGTH: 16
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 74
gccatgttgc tgatgc                                                      16

<210> SEQ ID NO 75
<211> LENGTH: 15
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 75
tcagattcaa accca                                                          15

<210> SEQ ID NO 76
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 76
tcagattcaa accc                                                           14

<210> SEQ ID NO 77
<211> LENGTH: 14
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 77
cagattcaaa ccca                                                           14

<210> SEQ ID NO 78
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 78
tcagattcaa acc                                                            13

<210> SEQ ID NO 79
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 79
cagattcaaa ccc                                                            13

<210> SEQ ID NO 80
<211> LENGTH: 13
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 80
agattcaaac cca                                                            13

<210> SEQ ID NO 81
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 81
tcagattcaa ac                                                             12

<210> SEQ ID NO 82
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 82
cagattcaaa cc                                                            12

<210> SEQ ID NO 83
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 83
agattcaaac cc                                                            12

<210> SEQ ID NO 84
<211> LENGTH: 12
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 84
gattcaaacc ca                                                            12

<210> SEQ ID NO 85
<211> LENGTH: 24
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 85
gcaccaccag catgtactgc gcct                                               24

<210> SEQ ID NO 86
<211> LENGTH: 24
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 86
tgcgattctg gtgcttggcg cggt                                               24

<210> SEQ ID NO 87
<211> LENGTH: 24
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 87
cgtactcctt ggtgcagtct tccc                                               24

```
<210> SEQ ID NO 88
<211> LENGTH: 24
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 88
ggaccgcagg tgtgtcttca ggtt                                               24

<210> SEQ ID NO 89
<211> LENGTH: 24
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 89
ttcgtacatg tggatctggc cgta                                               24

<210> SEQ ID NO 90
<211> LENGTH: 24
<212> TYPE: DNA
<213> ORGANISM: Artificial sequence
<220> FEATURE:
<223> OTHER INFORMATION: Oligomer sequence motif - sequence of monomers
      (nucleotides)

<400> SEQUENCE: 90
agcattcaga ttcaaaccca aatg                                               24

<210> SEQ ID NO 91
<211> LENGTH: 14
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(14)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (12)..(14)
<223> OTHER INFORMATION: Nucleotide analogue, such as LNA, such as beta-
      D-oxy LNA

<400> SEQUENCE: 91
accagcatgt actg                                                          14

<210> SEQ ID NO 92
<211> LENGTH: 14
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(14)
<223> OTHER INFORMATION: Internucleoside linkage, preferably
      phosphorothioate linkage
<220> FEATURE:
```

```
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (12)..(14)
<223> OTHER INFORMATION: Nucleotide analogue, such as LNA, such as beta-
      D-oxy LNA

<400> SEQUENCE: 92
aacgtgcact tgtg                                                       14

<210> SEQ ID NO 93
<211> LENGTH: 14
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(14)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (12)..(14)
<223> OTHER INFORMATION: Nucleotide analogue, such as LNA, such as beta-
      D-oxy LNA

<400> SEQUENCE: 93
ttctggtgct tggc                                                       14

<210> SEQ ID NO 94
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 94
gtgaaggctg ggctga                                                     16

<210> SEQ ID NO 95
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
```

```
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 95
tctgcttgtt ctggtt                                                   16

<210> SEQ ID NO 96
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 96
cctgcttaca gtcatc                                                   16

<210> SEQ ID NO 97
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 97
ctccttggtg cagtct                                                   16

<210> SEQ ID NO 98
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
```

```
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 98
gtgtgtcttc aggttc                                                       16

<210> SEQ ID NO 99
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 99
cgcaggtgtg tcttca                                                       16

<210> SEQ ID NO 100
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 100
gcagatgtag ggtttc                                                       16

<210> SEQ ID NO 101
<211> LENGTH: 16
<212> TYPE: DNA
<213> ORGANISM: Artificial sequence
<220> FEATURE:
<223> OTHER INFORMATION: Oligomer design or LNA oligomer compound
```

-continued

<400> SEQUENCE: 101
gccactgtca ttgttg                                                    16

<210> SEQ ID NO 102
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 102
ccagggctga ggtgtc                                                    16

<210> SEQ ID NO 103
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 103
gaggcagctt ggtgtt                                                    16

<210> SEQ ID NO 104
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)

-continued

<223> OTHER INFORMATION: Nucleotide analogue, such as LNA, such as beta-
     D-oxy LNA

<400> SEQUENCE: 104
tgctggtgga gctgtc                                                   16

<210> SEQ ID NO 105
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 105
gtgaggttga gcagcc                                                   16

<210> SEQ ID NO 106
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 106
gccgcacagg gtcgct                                                   16

<210> SEQ ID NO 107
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:

```
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 107
atgtagttta ccctgg                                                    16

<210> SEQ ID NO 108
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 108
ccatgaagcc aggctg                                                    16

<210> SEQ ID NO 109
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 109
tacatgtgga tctggc                                                    16

<210> SEQ ID NO 110
<211> LENGTH: 16
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
```

-continued

D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 110
gccatgttgc tgatgc                                                      16

<210> SEQ ID NO 111
<211> LENGTH: 15
<212> TYPE: DNA
<213> ORGANISM: Artificial sequence
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as beta-
      D-oxy LNA
<220> FEATURE:
<221> NAME/KEY: misc_feature
<222> LOCATION: (14)..(16)
<223> OTHER INFORMATION: Nucleotide analogue, such as LNA, such as beta-
      D-oxy LNA

<400> SEQUENCE: 111
tcagattcaa accca                                                       15

<210> SEQ ID NO 112
<211> LENGTH: 14
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (12)..(14)
<223> OTHER INFORMATION: Beta-D-oxy LNA, all LNA cytosines are 5-
      methylcytosine

<400> SEQUENCE: 112
accagcatgt actg                                                        14

<210> SEQ ID NO 113
<211> LENGTH: 14
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5- methylcytosine
<220> FEATURE:
<221> NAME/KEY: misc_feature
<222> LOCATION: (12)..(14)
<223> OTHER INFORMATION: Beta-D-oxy LNA, all LNA cytosines are 5-
      methylcytosine

<400> SEQUENCE: 113
aacgtgcact tgtg                                                         14

<210> SEQ ID NO 114
<211> LENGTH: 14
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (12)..(14)
<223> OTHER INFORMATION: Beta-D-oxy LNA, all LNA cytosines are 5-
      methylcytosine

<400> SEQUENCE: 114
ttctggtgct tggc                                                         14

<210> SEQ ID NO 115
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 115
gtgaaggctg ggctga                                                       16

<210> SEQ ID NO 116
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine

```
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 116
tctgcttgtt ctggtt                                                        16

<210> SEQ ID NO 117
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 117
cctgcttaca gtcatc                                                        16

<210> SEQ ID NO 118
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 118
ctccttggtg cagtct                                                        16

<210> SEQ ID NO 119
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
```

```
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 119
gtgtgtcttc aggttc                                                       16

<210> SEQ ID NO 120
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 120
cgcaggtgtg tcttca                                                       16

<210> SEQ ID NO 121
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 121
gcagatgtag ggtttc                                                       16

<210> SEQ ID NO 122
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
```

```
<222> LOCATION: (14)..(16)
<223> OTHER INFORMATION: Beta-D-oxy LNA, all LNA cytosines are 5-
      methylcytosine

<400> SEQUENCE: 122
gccactgtca ttgttg                                               16

<210> SEQ ID NO 123
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 123
ccagggctga ggtgtc                                               16

<210> SEQ ID NO 124
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 124
gaggcagctt ggtgtt                                               16

<210> SEQ ID NO 125
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
```

```
<223> OTHER INFORMATION: Beta-D-oxy LNA, all LNA cytosines are 5-
      methylcytosine

<400> SEQUENCE: 125
tgctggtgga gctgtc                                                    16

<210> SEQ ID NO 126
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 126
gtgaggttga gcagcc                                                    16

<210> SEQ ID NO 127
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 127
gccgcacagg gtcgct                                                    16

<210> SEQ ID NO 128
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
```

-continued methylcytosine

<400> SEQUENCE: 128
atgtagttta ccctgg                                                    16

<210> SEQ ID NO 129
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 129
ccatgaagcc aggctg                                                    16

<210> SEQ ID NO 130
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 130
tacatgtgga tctggc                                                    16

<210> SEQ ID NO 131
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

```
<400> SEQUENCE: 131
gccatgttgc tgatgc                                                      16

<210> SEQ ID NO 132
<211> LENGTH: 15
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 132
tcagattcaa accca                                                       15

<210> SEQ ID NO 133
<211> LENGTH: 16
<212> TYPE: DNA
<213> ORGANISM: Artificial sequence
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines are 5-
      methylcytosine
<220> FEATURE:
<221> NAME/KEY: misc_feature
<222> LOCATION: (14)..(16)
<223> OTHER INFORMATION: Beta-D-oxy LNA, all LNA cytosines are 5-
      methylcytosine

<400> SEQUENCE: 133
cgtcagtatg cgaatc                                                      16

<210> SEQ ID NO 134
<211> LENGTH: 8281
<212> TYPE: DNA
<213> ORGANISM: Homo sapiens

<400> SEQUENCE: 134
gcgcacaccc gccgctccca ctcacccgcg ccgctctccc gccttccccg cgcgccccgc       60
ggccgcccgc gggtctatgg gaagttcggg gacttgacag ccgctgccgc cgcagggcat      120
ttttggtcga agagagctga agtaatgaga agacatcatg gaggcccagt cccacagctc      180
cacgaccact gaaaagaaaa aagttgagaa ttccatagtg aagtgctcca ctcgaacaga      240
tgtgagcgag aaagccgttg cctccagcac cacttctaat gaggatgaaa gtcctggaca      300
gacttatcac agagagagaa gaaacgcaat cactatgcag ccacagaatg tccaggggct      360
cagcaaagtc agtgaggaac cttcaacatc gagtgacgag agggcctcat tgatcaagaa      420
```

```
agagatccat gggtccctgc cacacgtggc ggagccctct gtgccgtacc gcgggacggt    480
gtttgccatg gacccagga atggttacat ggagccccac taccaccctc ctcatctttt    540
ccctgccttc catcctcctg taccaattga tgccagacat catgagggcc gttaccatta    600
cgatccatct ccgattcctc cattgcatat gacttccgcc ttatctagta gccctacgta    660
tccggacctg cccttcatta ggatctcccc acaccggaac cccactgctg cttccgagtc    720
tcccttcagc cctccacatc cctacattaa tccctacatg gactatatcc gctccttgca    780
cagcagccca tcgctctcca tgatctcagc aacccgtggg ctgagcccta cagatgcgcc    840
ccatgcagga gtcagcccag cagaatacta tcatcagatg ccctgctaa ctggccagcg    900 cagcccctat gcagacatta ttccctcagc tgccaccgcc ggcacggggg ccatccacat    960
ggaatatctt catgctatgg atagcaccag attctccagc cccaggctgt cagccaggcc   1020
gagccgaaaa cgtacactgt ccatatcacc actctccgat catagctttg accttcagac   1080
catgataagg acgtctccca actccttggt cacgattctc aataattccc gtagcagctc   1140
ttcagcaagt ggctcctatg gtcacttatc tgcaagtgca atcagccctg ccttgagctt   1200
cacctactct tccgcgcccg tctctctcca catgcatcag cagatcctaa gccgacaaca   1260
gagcttaggt tcagcctttg gacacagccc tccactcatc caccctgccc caacttttcc   1320
aacacagagg cctattccag ggatccctac ggttctgaac cccgtccagg tcagctccgg   1380
cccttctgag tcctcacaga caagcccac gagtgagtct gcagtgagca gcactggtga   1440
cccgatgcac aacaagaggt ccaagatcaa acccgatgaa gacctcccca gcccaggggc   1500 tcggggggcag caggaacagc ccgaaggaac aaccccttgtc aaggaggaag gggacaaaga   1560
tgaaagcaaa caggagcctg aagtcatcta tgagacaaac tgccactggg aaggctgcgc   1620
gagggagttc gacacccaag agcagcttgt gcaccatata aataacgacc atattcatgg   1680
agagaagaag gagttcgtgt gcaggtggct ggactgctca agagagcaga aacccttcaa   1740
agcccagtat atgttggtag tgcatatgag aagacacacg ggcgagaagc ctcacaaatg   1800 cactttgaa ggttgcacaa aggcctactc gagactagaa aacttgaaaa cacacttgag   1860
atctcacact ggagagaaac catacgtctg tgagcacgaa ggttgcaaca aggctttctc   1920
aaatgcctct gatcgcgcca acaccaaaa cagaacgcat tccaatgaga aaccatatgt   1980
gtgcaaaatc ccaggctgca ctaagcgtta cacagaccca agctccctcc ggaaacatgt   2040
gaagacagtg catggcccag aggctcatgt caccaagaag cagcgagggg acatccatcc   2100
tcggccgcca cccccgagag attccggcag ccattcacag tccaggtcgc ctggccgacc   2160
gactcaggga gcccttggtg agcagcagga cctcagcaac actacctcaa agcgggaaga   2220
atgcctccag gtgaaaaccg tcaaggcaga aagccaatg acatctcagc caagccctgg   2280
tggtcagtct tcatgcagca gccaacagtc ccccatcagc aactattcca acagtgggct   2340
cgagcttcct ctgaccgatg gaggtagtat aggagacctc agtgccatcg atgaaacccc   2400
aatcatggac tcaaccattt ccactgcaac cacagccctt gctttgcaag ccaggagaaa   2460
cccggcaggg accaaatgga tggagcacgt aaaactagaa aggctaaaac aagtgaatgg   2520
aatgtttccg cgactgaacc ccattctacc ccctaaagcc cctgcggtct ctcctctcat   2580
aggaaatggc acacagtcca acaacacctg cagcttgggt gggcccatga cgcttctccc   2640
gggcagaagc gacctctctg gggtggacgt cactatgctg aacatgctca acagaaggga   2700
cagcagcgca agcaccatca gctcggccta cctgagcagc cgccgctcct cagggatctc   2760
gccctgcttc tccagccgcc gctccagcga ggcgtcacag gccgagggcc ggccgcagaa   2820
```

-continued

```
cgtgagcgtg gccgactcct acgacccat ctccaccgac gcctcgcgcc gctccagcga    2880
agccagccag agcgacggcc tgcccagcct gctcagcctc acgcccgccc agcagtaccg    2940
cctcaaggcc aagtacgcgg ctgccacagg agggccgccg ccgacgcccc tgcccaacat    3000
ggagaggatg agcctgaaga cgcgcctggc gctgctcggg gatgccctcg agcctggcgt    3060
ggccctgcct ccagttcatg ccccgaggag gtgcagcgac gggggagccc acggctacgg    3120
gcggcgccac ctgcagccgc acgatgcgcc gggccacggc gtgaggaggg ccagcgaccc    3180
ggtgcggaca ggctccgagg gcctggccct gcctcgtgtg ccgcgcttca gcagcctcag    3240
cagctgcaac cccccggcga tggccacgtc cgcggagaag cgcagtctcg tgcttcagaa    3300
ttacacgcgg cccgagggcg gccagtcccg aaacttccac tcgtccccct gtcctcccag    3360
catcaccgag aacgtcaccc tggagtccct gaccatggac gctgatgcca acctgaacga    3420
tgaggatttc ctgccggacg acgtggtgca gtatttaaat cccagaaacc aagcagggta    3480
cgagcagcac ttccccagcg ccctcccgga cgacagcaaa gtgccccacg ggcccggtga    3540
ctttgacgcg cccgggctgc cagacagcca cgctggccag cagttccatg ccctcgagca    3600
gccctgcccc gagggcagca aaaccgacct gcccattcag tggaacgaag tcagctccgg    3660
aagcgccgac ctgtcctcct ccaagctcaa gtgtgggccg cggcccgctg tgccgcagac    3720
tcgcgccttt gggttctgca acggcatggt cgtccacccg cagaaccccct tgaggagcgg    3780 gcctgctggg ggctatcaga ccctcgggga gaacagcaac ccctacggtg gcccagagca    3840
cttgatgctc cacaacagcc ccggaagtgg caccagtgga aacgccttcc atgaacagcc    3900
ctgtaaggcc ccgcagtatg ggaactgtct caacaggcag ccagtgggcc ctggtgcact    3960
cgacggtgcc tgtggtgccg ggattcaagc ctcaaagctg aagagcaccc ccatgcaagg    4020
gagcgggggc cagctgaatt tcggcctgcc ggtagcgcca aatgagtcag ctggcagcat    4080
ggtgaatggc atgcagaacc aggacccagt gggacagggg tacctggctc accagctcct    4140
cggcgacagc atgcagcacc cggggcagg ccgccccggt cagcagatgc ttgggcagat    4200
tagtgctacc tcacacatca acatctacca agggccagag agctgcctgc aggggctca    4260 cggcatgggc agccagccgt caagcttggc agttgtcagg ggctaccagc catgtgccag    4320
cttttggggc agcaggcgcc aggctatgcc gagggacagc cttgctctgc agtcaggaca    4380
gctcagtgac acaagtcaga cctgcagggt gaatggtatc aagatggaga tgaaaggca    4440 gccccatccg ctgtgctcta atctgcagaa ttactctggt cagttctatg accaaaccgt    4500
gggcttcagt cagcaagaca cgaaagctgg ttcattctct atttcagacg ccagctgcct    4560
gctacagggg accagcgcca aaaactctga gttactttcc ccaggtgcta atcaggtgac    4620
aagcacagtg gacagcctcg acagccatga cctggaaggg gtacagattg acttcgatgc    4680
catcatagac gatggggacc actccagcct gatgtcgggg gccctgagcc caagtatcat    4740
tcagaacctt tcccatagct cctcccgcct caccacgcct cgggcgtccc tcccattccc    4800
agcgctgtcc atgagcacca ccaacatggc tatcgggac atgagttctt tgctgacctc    4860
cctagcggaa gaaagcaaat tccttgcagt tatgcaatag gctttaggaa aaaaagactg    4920
caaccaacgg aaatcaatag gagttgaaga gattaaactg actttgtttt ggctgttttt    4980
ttagttctgt atgtatttta gcaatctcat ctcacctaac tgagatgtgt ttcaattata    5040
ttccttttat ggaaaggac tctgaaaaac cctaaagtat tctagggaga aactgtcttc    5100
catttcagtt ttgaatcagt attgttacac tcaaaccacc ctcttttaa aaaaaaaaa    5160
```

```
aaaaactgta agccccgccc ccttttagt aaaccgatgt aaatttgtga tgtgcatatt    5220
cttctttctt ttagaagagc agtcaaatta aaggatttga catgttttgc tgttgctcaa    5280
aggaaatagg agttggtgtg cttgtgacca aggggttaca cttccagctt ttaaaattct    5340
cctttacatg tgctcagtgt tttgttttgt gttttggttt ctgttttta ttttaattcc    5400 cacattgggc acaagaatca gaatatggat agctagttta agaaactttt gtgggtgcac    5460
tgtagcatag atgacagaat attgatgttc ccccatctc caattcagtt cagggcattc    5520
cacagttaaa cagaaatggg aacgtggggc tcttataaat gaaatgggcg ctcacagttt    5580
tggttttcag ctcttcatgt ctgtaagtgt gcttgggggg aggctatgtc tgtatggtcg    5640
attctcagtt atcacatttg cctctcctcc cactaccttc atgaacattc agtgctgttt    5700
cgcactgcag ttagagagaa gggacggaca gttggtgaca ctcagccaca ttgctacttt    5760
tatctgttct ggtaagaagt tagatagatg gtagattgaa gcaattgggt agaattagtt    5820
gggggaatat ttatgagttg ctgtgtttgt tgattagttc catctctttc ccattttaac    5880
tgagaattga ttatatatag ctctaagtat ataggtattt aaacaacccc acaagcggct    5940
gtatcagtaa catttattaa ttccactata gtgagggagg atttccattc taaataccctt    6000 attttgaggg atttataaaa cttagttgta aaagagaaag cccacatagt gggaataaat    6060
tgcttcagcc attttagta tttgagagca ctagggaaga tgtttagtag ctgtgtggat    6120
gccttttttc acccctgtc tattgaatgc tgcatccatt cacgaagtta aatgttacat    6180
gcagttagtc cttaatgtgg actggatctg tacttttgtt ttggattaaa acatttaaag    6240 attttttgaag tgcagctact ccccacgtgc atttgataca cataaaagtc atactgtgtg    6300
tgcacaaaga gtacatggat tttccagcat attgctttaa aaaattatat aaactgttaa    6360
aatattaaca cctcaggcta cctgctgtat tctgtcccat tgacccctgg aattggattt    6420
actgcaagtg attgataatt caattatgtg gcttttcccc tttaatcttg ccatttaaat    6480
tacagtagaa agacaaaatc aagtaaaata aagtgttaga taatagaaag agtgttaaga    6540
ccagcccact tttctcatgt ttatgttctt tcatttggac caagaatctc cgcatggagg    6600
ttgatttgcc actggggact ttggctaaga ctattaggtt tgctttcaac tagatgttcc    6660
tgagacaagc agagggacac tgcaattccc cttccatgcc tgctgttctc ccccatgtaa    6720
gtcttctttg aaattaacgg atgtgtctcc tttggaacag ccccataaca aaagagaact    6780
actgatctga gcataggaaa gtagaggctc taccactttt cagttgaaaa agcaagactt    6840
tctctgtgtt tctgaaacaa ggcataatgt tgtcacagaa tcagagatcc agtctcactt    6900
ttccacaaat ctccaaatct ccagtcttat cttgtgtgct ctaatggttt ggttcaatcc    6960
cttcccaact cttgttttca aagcatgggg cctgagtgtt ctccactcct cctaagaaag    7020
gagcttgggt ggaagggacc atgctgacct cctccatcag agggctcttc cagtagtatt    7080
ctcggatgca acctccattt ctcagttacc attatttcct gtatcagctt tgtccttcct    7140
ggagggatgc acagtgatcc ggcccaccac tgttgttgtc ttgtgcttct gctctttcct    7200
atggtttcag gttattttct gggttttcccc tattcttctt ttatttcttt ttttttttat    7260
atttgctttc ctttctactg cttttagatt tgcaggagat gcaagtttca gctcaatgtt    7320
tggcttctct caatatggaa atttcagaag gacagaggag aggagggagg aagaagaaag    7380
tatactcctc cagaatttca gtgatctgtt gtggcagtcc agtggaagga aggtcttttg    7440
aggtcactta gaagcatctt tttgggacat ccttttggga tctctgtagg ctaggcatct    7500
catatcttga gactcaccccc cagcctccaa gcctctctcc atttctctaa cctatgcatt    7560
```

```
ttagagcgag aggaccgcct cactagtgtc accatcctgc cttttctaaa acatgcaggc    7620
tcacacattc tactcctgct taatgtctgt gttaaacgtt ttctaaccat ttttgtttta    7680
tttttctgaa aaagttaacc cctcccaact cctcacacat tggctcttcc tcttgagcca    7740
caaagttttg attcttgcga tgtatgtgcc ttattttatg ttaatcttgt caatgagagg    7800
gaccagttgg tgttgcccaa tcagcactcc aaggctgtgt gtgcaccagc cagagagcgc    7860
acggtggtag cagagtcgag gctgtcttgt atcctggttt catgtgttgt tttgaactga    7920
taggaggatg ttctcttctg acaagttacc cttgtgtatc ctgcagacat gtaaaataaa    7980
atacaagttc attttttca ccttttttag attttttaa aaaataaaat gtgtaatcct    8040 tttttaaaa gaaacacatg taaatacatt taagtattgt aggcatagcg ttcagatgtg    8100
actggcccag gcgttcctcg gacaagcctg cattccccgt gatcacgccc acctcaagcc    8160
caggggctgc agcccagcca cagatgaact ctacctttgc tttcagaacc acttagtcct    8220
tttgtaacaa agaaaaaaaa atgtttctta caatgtcaat aaaaaattct ttgtatggaa    8280
a                                                                   8281
```